US010700288B2

(12) United States Patent
Suzuki et al.

(10) Patent No.: US 10,700,288 B2
(45) Date of Patent: Jun. 30, 2020

(54) LIGHT-EMITTING ELEMENT, LIGHT-EMITTING DEVICE, ELECTRONIC DEVICE, LIGHTING DEVICE, AND LIGHTING SYSTEM

(71) Applicant: Semiconductor Energy Laboratory Co., Ltd., Kanagawa-ken (JP)

(72) Inventors: Kunihiko Suzuki, Kanagawa (JP); Satoshi Seo, Kanagawa (JP); Harue Osaka, Kanagawa (JP); Tsunenori Suzuki, Kanagawa (JP); Naoaki Hashimoto, Kanagawa (JP); Kyoko Takeda, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 495 days.

(21) Appl. No.: 15/215,117

(22) Filed: Jul. 20, 2016

(65) Prior Publication Data

US 2017/0025621 A1 Jan. 26, 2017

(30) Foreign Application Priority Data

Jul. 24, 2015 (JP) .................................. 2015-146604
Jan. 15, 2016 (JP) .................................. 2016-006140

(51) Int. Cl.
*H01L 51/00* (2006.01)
*C07D 209/86* (2006.01)
(Continued)

(52) U.S. Cl.
CPC ........ *H01L 51/0072* (2013.01); *C07D 209/86* (2013.01); *C09K 11/025* (2013.01);
(Continued)

(58) Field of Classification Search
None
See application file for complete search history.

(56) References Cited

U.S. PATENT DOCUMENTS 7,175,922 B2    2/2007 Jarikov et al.
7,183,010 B2    2/2007 Jarikov
(Continued)

FOREIGN PATENT DOCUMENTS

EP    1 202 608 A2    5/2002
JP    2007137829 A *    6/2007
(Continued)

OTHER PUBLICATIONS

Machine English translation of Kido et al. (JP 2007-137829 A). Sep. 30, 2018.*

(Continued)

*Primary Examiner* — Jay Yang
(74) *Attorney, Agent, or Firm* — Husch Blackwell LLP

(57) ABSTRACT

A light-emitting element that contains a fluorescent compound, which has high efficiency is provided. A light-emitting element in which the proportion of delayed fluorescence to the total light emitted from the light-emitting element is higher than that in a conventional light-emitting element is provided. Emission efficiency of the light-emitting element containing a fluorescent compound can be improved by increasing the probability of TTA caused by an organic compound in an EL layer, converting energy of triplet excitons, which does not contribute to light emission, into energy of singlet excitons, and making the fluorescent compound emit light by energy transfer of the singlet excitons.

24 Claims, 36 Drawing Sheets

(51) Int. Cl.
*C09K 11/02* (2006.01)
*H01L 51/50* (2006.01)
(52) U.S. Cl.
CPC ...... *H01L 51/0052* (2013.01); *H01L 51/5012* (2013.01); *H01L 51/5056* (2013.01); *H01L 51/5072* (2013.01)

(56) References Cited

U.S. PATENT DOCUMENTS

| | | | |
|---|---|---|---|
| 7,332,857 | B2 | 2/2008 | Seo et al. |
| 7,597,967 | B2 | 10/2009 | Kondakova et al. |
| 7,993,760 | B2 | 8/2011 | Komori et al. |
| 8,034,465 | B2 | 10/2011 | Liao et al. |
| 8,274,214 | B2 | 9/2012 | Ikeda et al. |
| 8,853,680 | B2 | 10/2014 | Yamazaki et al. |
| 8,963,127 | B2 | 2/2015 | Pieh et al. |
| 8,981,355 | B2 | 3/2015 | Seo |
| 8,993,129 | B2 | 3/2015 | Endo et al. |
| 8,994,263 | B2 | 3/2015 | Shitagaki et al. |
| 9,054,317 | B2 | 6/2015 | Monkman et al. |
| 9,159,942 | B2 | 10/2015 | Seo et al. |
| 9,175,213 | B2 | 11/2015 | Seo et al. |
| 9,356,250 | B2 | 5/2016 | Ohsawa et al. |
| 9,362,517 | B2 | 6/2016 | Ohsawa et al. |
| 9,368,742 | B2 | 6/2016 | Kawata et al. |
| 9,444,063 | B2 | 9/2016 | Nonaka et al. |
| 9,604,928 | B2 | 3/2017 | Shitagaki et al. |
| 2003/0175553 | A1 | 9/2003 | Thompson et al. |
| 2005/0048310 | A1 | 3/2005 | Cocchi et al. |
| 2005/0221116 | A1 | 10/2005 | Cocchi et al. |
| 2006/0134464 | A1 | 6/2006 | Nariyuki |
| 2007/0090756 | A1 | 4/2007 | Okada et al. |
| 2012/0061651 | A1* | 3/2012 | Osaka ................. C07D 333/76 257/40 |
| 2012/0217487 | A1 | 8/2012 | Yamazaki et al. |
| 2013/0009909 | A1* | 1/2013 | Yamazaki ............... G06F 3/044 345/174 |
| 2014/0066633 | A1* | 3/2014 | Osaka .................. C07D 209/86 548/445 |
| 2015/0069352 | A1 | 3/2015 | Kim et al. |
| 2015/0333283 | A1 | 11/2015 | Ishisone et al. |
| 2015/0349284 | A1 | 12/2015 | Seo et al. |
| 2016/0043146 | A1 | 2/2016 | Uesaka et al. |
| 2016/0064684 | A1 | 3/2016 | Seo et al. |
| 2016/0093823 | A1 | 3/2016 | Seo et al. |
| 2016/0118625 | A1 | 4/2016 | Uesaka et al. |
| 2016/0126463 | A1 | 5/2016 | Kadoma et al. |
| 2016/0248032 | A1 | 8/2016 | Seo et al. |

FOREIGN PATENT DOCUMENTS

| | | | |
|---|---|---|---|
| JP | 2008-288344 | A | 11/2008 |
| KR | 1020110006129 | * | 1/2011 |

OTHER PUBLICATIONS

Machine English translation of Hong et al. (KR 10-2011-0006129). Sep. 30, 2018.*
Suzuki, T. et al., "Highly Efficient Long-Life Blue Fluorescent Organic Light-Emitting Diode Exhibiting Triplet-Triplet Annihilation Effects Enhanced by a Novel Hole-Transporting Material," Japanese Journal of Applied Physics, 2014, vol. 53, pp. 052102-1-052102-6.
Yersin, H. et al., *Highly Efficient OLEDs with Phosphorescent Materials*, 2008, pp. 1-97,283-309, Wiley-VCH Verlag GmbH & Co.
Tokito,S. et al., "Improvement in Performance by Doping," Organic EL Display, Aug. 20, 2004, pp. 67-99, Ohmsha.
Jeon, W.S. et al., "Ideal Host and Guest System in Phosphorescent OLEDs," Organic Electronics, 2009, vol. 10, pp. 240-246, Elsevier.
Su, S-J et al., "RGB Phosphorescent Organic Light-Emitting Diodes by Using Host Materials with Heterocyclic Cores:Effect of Nitrogen Atom Orientations," Chemistry of Materials, 2011, vol. 23, No. 2, pp. 274-284.
Rausch, A.F. et al., "Matrix Effects on the Triplet State of the OLED Emitter Ir(4,6-dFppy)2(pic)(Flrpic):Investigations by High-Resolution Optical Spectroscopy," Inorganic Chemistry, 2009, vol. 48, No. 5, pp. 1928-1937.
Gong, X. et al., "Phosphorescence from Iridium Complexes Doped into Polymer Blends," Journal of Applied Physics, Feb. 1, 2004, vol. 95, No. 3, pp. 948-953.
Zhao, Q. et al., "Synthesis and Photophysical, Electrochemical, and Electrophosphorescent Properties of a Series of Iridium(III) Complexes Based on Quinoline Derivatives and Different β-Diketonate Ligands," Organometallics, Jun. 14, 2006, vol. 25, No. 15, pp. 3631-3638.
Hino, Y. et al., "Red Phosphorescent Organic Light-Emitting Diodes Using Mixture System of Small-Molecule and Polymer Host," Japanese Journal of Applied Physics, Apr. 21, 2005, vol. 44, No. 4B, pp. 2790-2794.
Tsuboyama, A. et al., "Homoleptic Cyclometalated Iridium Complexes with Highly Efficient Red Phosphorescence and Application to Organic Light-Emitting Diode," Journal of the American Chemical Society, 2003, vol. 125, No. 42, pp. 12971-12979.
Kondakova, M.E. et al., "High-Efficiency, Low-Voltage Phosphorescent Organic Light-Emitting Diode Devices with Mixed Host," Journal of Applied Physics, Nov. 4, 2008, vol. 104, pp. 094501-1-094501-17.
Chen, F-C. et al., "Triplet Exciton Confinement in Phosphorescent Polymer Light-Emitting Diodes," Applied Physics Letters, Feb. 17, 2003, vol. 82, No. 7, pp. 1006-1008.
Lee, J.Y. et al., "Stabilizing the Efficiency of Phosphorescent Organic Light-Emitting Diodes," SPIE Newsroom, Apr. 21, 2008, pp. 1-3.
Tokito, S. et al., "Confinement of Triplet Energy on Phosphorescent Molecules for Highly-Efficient Organic Blue-Light-Emitting Devices," Applied Physics Letters, Jul. 21, 2003, vol. 83, No. 3, pp. 569-571.
Endo, A. et al., "Efficient Up-Conversion of Triplet Excitons Into a Singlet State and Its Application for Organic Light Emitting Diodes," Applied Physics Letters, Feb. 24, 2011, vol. 98, No. 8, pp. 083302-1-083302-3.
Itano, K. et al., "Exciplex Formation at the Organic Solid-State Interface: Yellow Emission in Organic Light-Emitting Diodes Using Green-Flourescent tris(8-quinolinolato)aluminum and Hole-Transporting Molecular Materials with Low Ionization Potentials," Applied Physics Letters, Feb. 9, 1998, vol. 72, No. 6, pp. 636-638.
Park, Y-S. et al., "Efficient Triplet Harvesting by Fluorescent Molecules Through Exciplexes for High Efficiency Organic Light-Emitting Diodes," Applied Physics Letters, Apr. 18, 2013, vol. 102, No. 15, pp. 153306-1-153306-5.

* cited by examiner

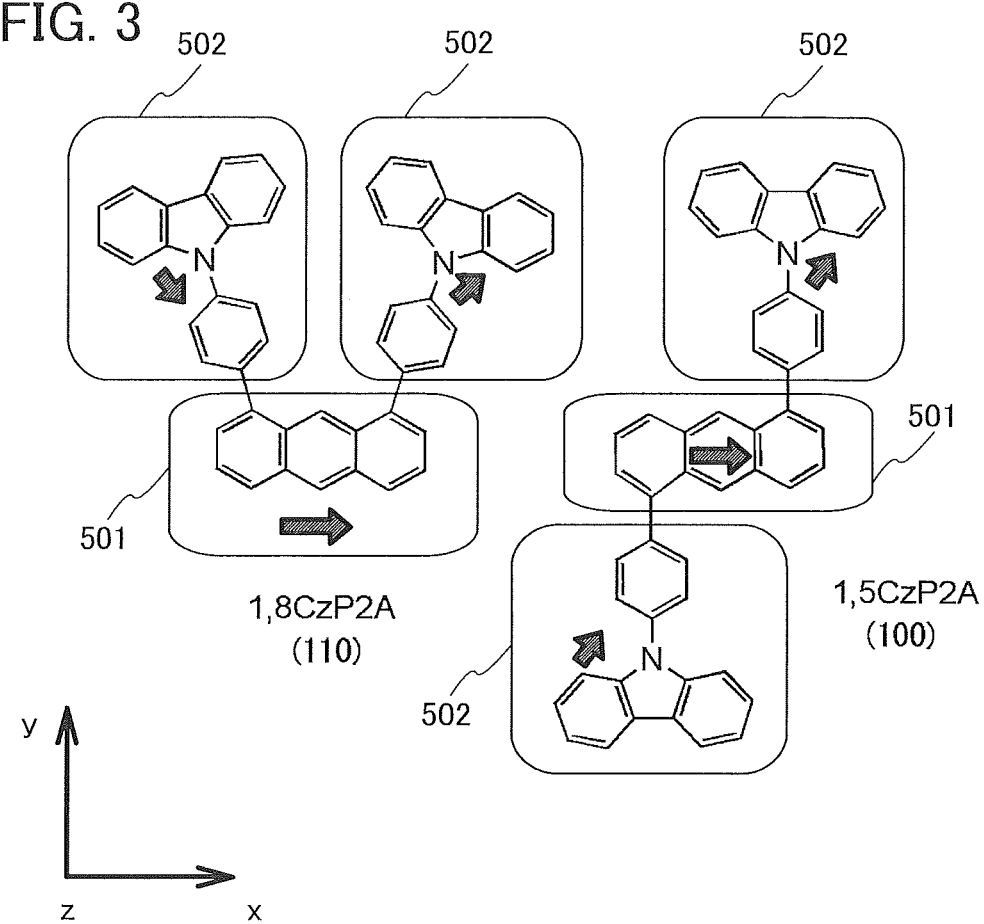

FIG. 36A
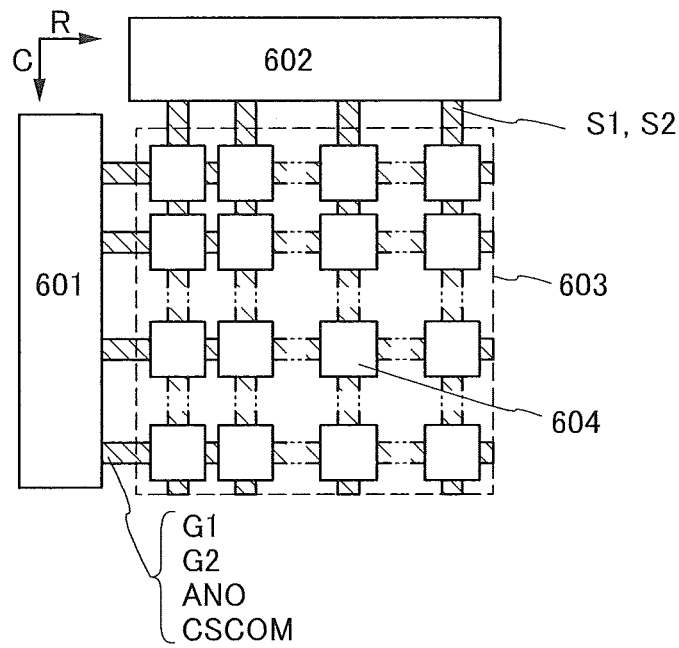
FIG. 36B1
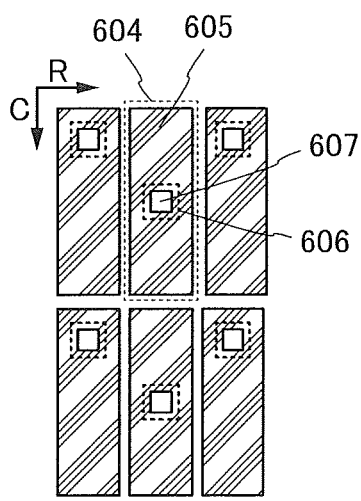
FIG. 36B2
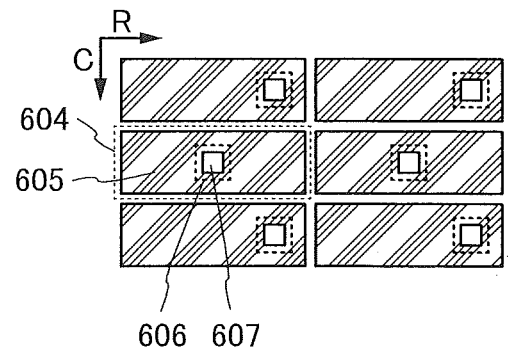

LIGHT-EMITTING ELEMENT, LIGHT-EMITTING DEVICE, ELECTRONIC DEVICE, LIGHTING DEVICE, AND LIGHTING SYSTEM

BACKGROUND OF THE INVENTION

1. Field of the Invention

One embodiment of the present invention relates to a light-emitting element, a light-emitting device, an electronic device, and a lighting device. In addition, one embodiment of the present invention relates to a lighting system. Note that one embodiment of the present invention is not limited to the above technical field. The technical field of one embodiment of the invention disclosed in this specification and the like relates to an object, a method, or a manufacturing method. In addition, one embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting device, a power storage device, a storage device, a method for driving any of them, and a method for manufacturing any of them.

2. Description of the Related Art

In recent years, research and development of light-emitting elements using electroluminescence (EL) have been actively conducted. In a basic structure of such a light-emitting element, a layer containing a light-emitting substance (an EL layer) is interposed between a pair of electrodes. By applying a voltage between the pair of electrodes of this element, light emission from the light-emitting substance can be obtained.

Since the above light-emitting element is a self-luminous type, a display device using this light-emitting element has advantages such as high visibility, no necessity of a backlight, and low power consumption. Further, such a light-emitting element also has advantages in that the element can be formed to be thin and lightweight, and that response time is high.

It is said that the light emission mechanism of a light-emitting element is as follows: when a voltage is applied between a pair of electrodes with an EL layer including a light-emitting substance provided therebetween, electrons injected from a cathode and holes injected from an anode recombine in the light emission center of the EL layer to form molecular excitons, and energy is released and light is emitted when the molecular excitons relax to the ground state.

The excited states of an organic compound in which molecular excitons are formed include a singlet excited state ($S^*$) and a triplet excited state ($T^*$), and light emission from the singlet excited state is referred to as fluorescence, and light emission from the triplet excited state is referred to as phosphorescence. The statistical generation ratio thereof in the light-emitting element is considered to be $S^*:T^*=1:3$. In other words, a light-emitting element containing a compound emitting phosphorescence has higher emission efficiency than a light-emitting element containing a compound emitting fluorescence. Therefore, light-emitting elements containing phosphorescent compounds capable of converting a triplet excited state into light emission has been actively developed in recent years.

Among light-emitting elements containing phosphorescent compounds, in particular, a light-emitting element that emits blue light has not yet been put into practical use because it is difficult to develop a stable compound having a high triplet excited energy level. For this reason, the development of a light-emitting element containing a more stable fluorescent compound has been conducted and high efficiency of a light-emitting element containing a fluorescent compound (fluorescent light-emitting element) has been required.

In the light-emitting element containing a fluorescent compound, triplet-triplet annihilation (TTA) is known as a light emission mechanism capable of converting part of a triplet excited state into light emission. The term TTA refers to a process in which, when two triplet excitons approach each other, excited energy and spin angular momentum are exchanged and transferred to form singlet excitons.

As a compound in which TTA occurs, a compound including an anthracene skeleton is known. Non-Patent Document 1 discloses that the use of a compound including an anthracene skeleton as a host material achieves high external quantum efficiency in a light-emitting element that emits blue light. It also discloses that the proportion of the delayed fluorescence due to TTA to the total light emitted from the light-emitting element using a compound including an anthracene skeleton is approximately 10%.

PATENT DOCUMENT

Non-Patent Document

[Non-Patent Document 1]
Tsunenori Suzuki et al., Japanese Journal of Applied Physics, Vol. 53, 052102 (2014)

SUMMARY OF THE INVENTION

One embodiment of the present invention is to provide a light-emitting element which contains a fluorescent compound and has high efficiency. Another embodiment of the present invention is to provide a light-emitting element in which the proportion of delayed fluorescence to the total light emitted from the light-emitting element is higher than that in a conventional light-emitting element. Another embodiment of the present invention is to provide a novel light-emitting element. Another embodiment of the present invention is to provide a novel light-emitting device. Another embodiment of the present invention is to provide a novel light-emitting device, a novel electronic device, or a novel lighting device. Another embodiment of the present invention is to provide a lighting system in which energy saving of a light-emitting element that is a light source is achieved. Note that the description of the object does not disturb the existence of other objects. In one embodiment of the present invention, there is no need to achieve all the objects. Other objects will be apparent from and can be derived from the description of the specification, the drawings, the claims, and the like.

According to one embodiment of the present invention, emission efficiency of a light-emitting element containing a fluorescent compound can be improved by increasing the probability of TTA caused by an organic compound in an EL layer, converting energy of triplet excitons, which does not contribute to light emission, into energy of singlet excitons, and making the fluorescent compound emit light by energy transfer of the singlet excitons.

As one of methods for efficiently converting the energy of triplet excitons into the energy of singlet excitons, energy transfer and intersystem crossing which are caused by the Förster mechanism are used. The Förster mechanism is a mechanism in which energy is transferred by resonance, which occurs more easily when the following conditions are satisfied: organic compounds (host materials) containing triplet excitons approach each other with an intermolecular distance of 1 nm to 10 nm, the oscillator strength for transition from the lowest triplet excited level (referred as a $T_1$ level) of the organic compound (host material) to one of levels of triplet excited states which are higher than the $T_1$ level of the organic compound (referred as $T_n$ levels) is high (energy absorption in transition is high), and the like.

One embodiment of the present invention is to provide a light-emitting element in which energy transfer by the Förster mechanism is likely to occur so that the probability of TTA in an EL layer of a light-emitting element is increased.

One embodiment of the present invention is a light-emitting element including an EL layer between an anode and a cathode. The EL layer includes a light-emitting layer. The light-emitting layer comprises a first organic compound. A difference between the $T_1$ level of the first organic compound and one or more of $T_n$ levels of the first organic compound is less than the sum of the $T_1$ level and 0.6 eV. Note that the levels of triplet excited states which are higher than the $T_1$ level are referred to as $T_n$ levels in this invention. That is, one or more of the $T_n$ levels of the first organic compound preferably have an energy level close to twice the $T_1$ level of the first organic compound, because energy transfer from the $T_1$ level to the $T_n$ levels is facilitated.

In the above structure, an energy difference between any one of the $T_n$ levels of the first organic compound and any one of levels of singlet excited states of the first organic compound is 1 eV or less. Note that the levels of the singlet excited states of the first organic compound includes an $S_1$ level (the lowest singlet excited level) and $S_n$ levels (levels that are higher than the $S_1$ level). This case is also preferable because intersystem crossing easily occurs as the energy level of any one of the $T_n$ levels of the first organic compound is closer to that of any one of the $S_1$ level and the $S_n$ levels of the first organic compound.

Thus, in the above structure, an energy difference between any one of the $T_n$ levels of the first organic compound and any one of the $S_1$ level and the $S_n$ levels of the first organic compound is 1 eV or less.

In each of the above structures, an oscillator strength for excitation from the $T_1$ level of the first organic compound to one of the levels of the triplet excited states higher than the $T_1$ level of the first organic compound is 0.0015 or more.

In each of the above structures, the first organic compound is an organic compound (host material) in which TTA can be efficiently caused and triplet excitons, which do not contribute to light emission, are converted into singlet excitons. Thus, the first organic compound preferably includes a tetracene skeleton or an anthracene skeleton.

In each of the above structures, the first organic compound has Structural Formula (100) or Structural Formula (110).

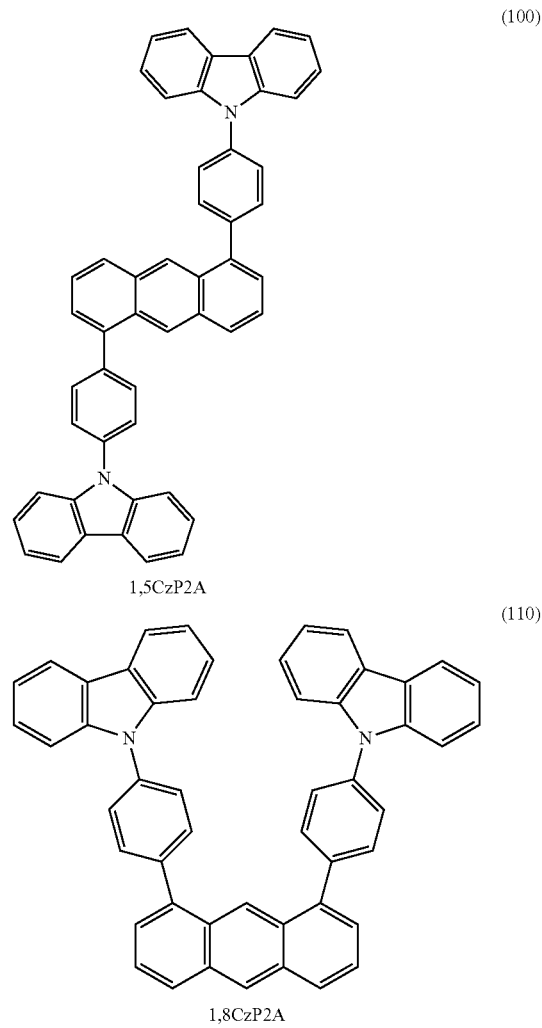

1,5CzP2A (100)

1,8CzP2A (110)

The above-described first organic compound is an organic compound (host material) in which TTA can be efficiently caused, triplet excitons, which does not contribute to light emission, can be efficiently converted into singlet excitons, and the proportion of delayed fluorescence to the total light emitted from the organic compound is high because the triplet exciton has long excitation lifetime.

Thus, in the light-emitting element which includes the first organic compound in the light-emitting layer and which has the above structure, the light-emitting element exhibits delayed fluorescence, and emission intensity of the delayed fluorescence component to the emission intensity of the total light emitted from the light-emitting element is at least 5% or more, preferably 10% or more, further preferably 15% or more for obtaining higher efficiency. Note that in the case where the energy of triplet excitons is converted into the energy of singlet excitons through TTA, the proportion of delayed fluorescence due to TTA to the total light emitted from the light-emitting element can be increased because the proportion of singlet excitons having a light-emitting property is increased. Note that in the case where a second organic compound that is a guest material is included in the light-emitting layer, because light emission may occur due to direct recombination of carriers in the guest material without the host material, the proportion of delayed fluorescence to the total light emission may be decreased compared to the case of an element structure which is the same as that of the light-emitting element except for not including the guest material.

In the above structures, the light-emitting layer comprises the first organic compound and the second organic compound, and an $S_1$ level of the first organic compound is higher than an $S_1$ level of the second organic compound. Moreover, light emission from the light-emitting element is derived from the second organic compound.

In the above structure, the second organic compound includes a pyrene skeleton.

In each of the above structures, a $T_1$ level of the second organic compound is higher than the $T_1$ level of the first organic compound.

In each of the above structures, the EL layer includes a hole-transport layer and a light-emitting layer. The hole-transport layer in contact with the light-emitting layer is located between the anode and the light-emitting layer. The hole-transport layer comprises a third organic compound, and a $T_1$ level of the third organic compound is higher than the $T_1$ level of the first organic compound.

In each of the above structures, the EL layer includes an electron-transport layer and a light-emitting layer. The electron-transport layer in contact with the light-emitting layer is located between the cathode and the light-emitting layer. The electron-transport layer comprises a fourth organic compound and a $T_1$ level of the fourth organic compound is higher than the $T_1$ level of the first organic compound.

Another embodiment of the present invention is a light-emitting device including the light-emitting element having any one of the above structures and one of a transistor and a substrate.

Another embodiment of the present invention is an electronic device including the light-emitting device having any one of the above structures and any one of a microphone, a camera, an operation button, an external connection portion, and a speaker.

Another embodiment of the present invention is an electronic device including the light-emitting device having the above-described structure and one of a housing and a touch sensor function.

Another embodiment of the present invention is a lighting device including the light-emitting device having the above-described structure, and any one of a housing, a cover, and a support.

The present invention includes, in its scope, not only a light-emitting device including the light-emitting element but also a lighting device including the light-emitting device. The light-emitting device in this specification refers to an image display device and a light source (e.g., a lighting device). In addition, the light-emitting device includes, in its category, all of a module in which a connector such as a flexible printed circuit (FPC) or a tape carrier package (TCP) is connected to a light-emitting device, a module in which a printed wiring board is provided on the tip of a TCP, and a module in which an integrated circuit (IC) is directly mounted on a light-emitting element by a chip on glass (COG) method.

A lighting system that is another embodiment of the present invention has a structure in which driving of a light-emitting element that is a light source is controlled in accordance with external information obtained from a sensor. Note that as the light-emitting element in the lighting system, the above-described light-emitting element which is one embodiment of the present invention is preferably used.

That is, one embodiment of the present invention is a lighting system including a sensor, a control unit, and a light-emitting element. Information detected by the sensor is input to the control unit. The control unit is configured to drive the light-emitting element electrically connected to the control unit on the basis of the information. The light-emitting element includes an EL layer between an anode and a cathode. The EL layer includes a light-emitting layer. The light-emitting layer includes a first organic compound. A difference between a $T_1$ level of the first organic compound and one or more of $T_n$ levels of the first organic compound is less than the sum of the $T_1$ level and 0.6 eV.

Another embodiment of the present invention is a lighting system including a sensor, a control unit, and a light-emitting element. The control unit includes a communication unit, a CPU, and a memory. The memory includes a program for driving the light-emitting element based on exterior information. The communication unit is configured to send the exterior information acquired by the sensor to the CPU. The CPU is configured to drive the light-emitting element by reading out the program from the memory and executing the program. The light-emitting element includes an EL layer between an anode and a cathode. The EL layer includes a light-emitting layer. The light-emitting layer includes a first organic compound. A difference between a $T_1$ level of the first organic compound and one or more of $T_n$ levels of the first organic compound is less than the sum of the $T_1$ level and 0.6 eV.

According to one embodiment of the present invention, a light-emitting element containing a fluorescent compound, which has high efficiency can be provided. According to one embodiment of the present invention, a light-emitting element in which the proportion of delayed fluorescence to the total light emitted from the light-emitting element is higher than that in a conventional light-emitting element can be provided. According to one embodiment of the present invention, a novel light-emitting element and a novel light-emitting device can be provided. A novel light-emitting device, a novel electronic device, or a novel lighting device can be provided. A lighting system in which energy saving of a light-emitting element that is a light source is achieved can be provided.

BRIEF DESCRIPTION OF THE DRAWINGS

In the accompanying drawings:

FIG. 3 shows the directions of the transition dipole moments and oscillator strengths in molecular structures;

FIGS. 36A, 36B1, and 36B2 show block diagrams of a display device;

DETAILED DESCRIPTION OF THE INVENTION

Hereinafter, embodiments of the present invention will be described with reference to the accompanying drawings. Note that the present invention is not limited to the following description, and modes and details thereof can be variously changed without departing from the spirit and scope of the present invention. Therefore, the present invention should not be construed as being limited to the description in the following embodiments.

Note that the terms "film" and "layer" can be interchanged with each other according to circumstances. For example, in some cases, the term "conductive film" can be used instead of the term "conductive layer," and the term "insulating layer" can be used instead of the term "insulating film".

Embodiment 1

In this embodiment, a mechanism of occurrence of TTA (triplet-triplet annihilation) in an EL layer of a light-emitting element is described.

There are various theories on the detail of the mechanism of TTA, and it is not defined clearly. In one embodiment of the present invention, energy transfer shown in schemes in FIGS. 1A to 1D is assumed to occur in TTA.

Figure 1A:
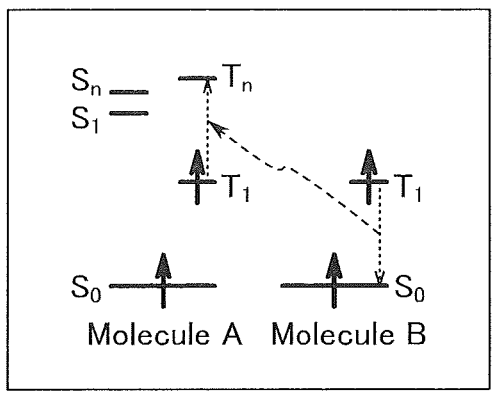
FIGS. 1A to 1D each illustrate a mechanism of TTA.

First, in the case where triplet excitons of two molecules of the same kind (a molecule A and a molecule B) exist adjacently as shown in FIG. 1A, energy released when the molecule B transits from a $T_1$ level to an $S_0$ level is absorbed by the molecule A, and an electron at the $T_1$ level of the molecule A transits to a $T_n$ level. Thus, it is thought that the vicinity of an energy level that is higher than the $T_1$ level of the molecule A by the $T_1$ level of the molecule B is the $T_n$ level to which the molecule A can transit.

Figure 1B:
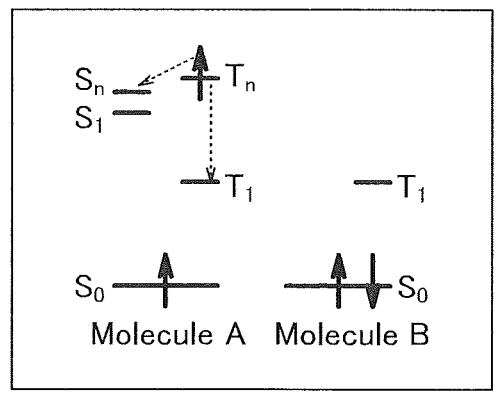
Figure 1C:
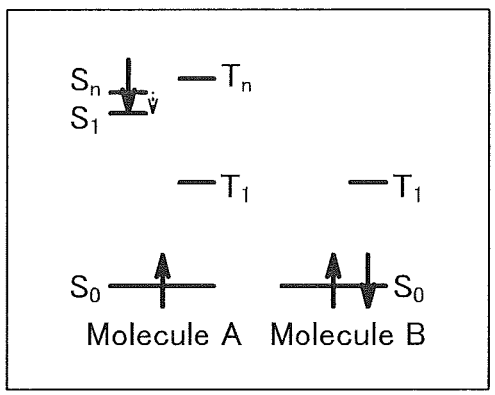

Next, as shown in FIG. 1B, the electron transited to the $T_n$ level of the molecule A undergoes intersystem crossing into an $S_n$ level whose energy level is close to the $T_n$ level with a certain probability. Furthermore, the electron at the $S_n$ level transits to a $S_1$ level by internal transition (FIG. 1C).

Figure 1D:
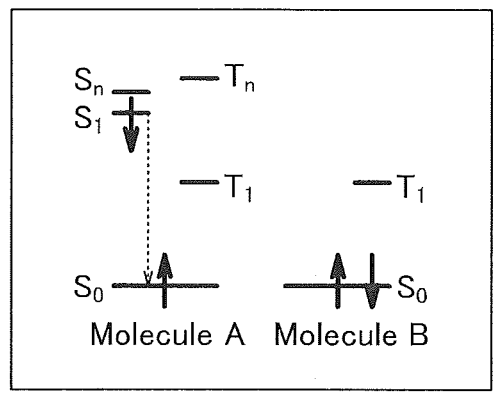

When the electron at the $S_1$ level transits to the $S_0$ level as shown in FIG. 1D, delayed fluorescence is generated.

As described above, using the excitation energy of one of two molecules, the other molecule transits to a higher level; thus, up to half of 75% of $T_1$ excitons can be extracted as emission. Since there is also 25% of $S_1$ excitons generated by current excitation, the total internal quantum efficiency can be 62.5% at the maximum.

Note that in the case where intermolecular energy transfer through TTA described in FIGS. 1A to 1D occurs, an increase in the efficiency of energy transfer from the molecule B to the molecule A in FIG. 1A increase the probability of transition from the $T_1$ level to the $T_n$ level, thereby increasing the number of $S_1$ excitons that are finally generated. As mechanisms of such intermolecular energy transfer, two mechanisms, i.e., the Dexter mechanism (electron exchange interaction) and the Förster mechanism (dipole-dipole interaction) are given. The fact that the energy transfer between triplet excitons ($T_1$-$T_1$) is possible in either of the mechanisms is described below.

In the Dexter mechanism, electron spins of both two molecules are stored before and after energy transfer. Thus, when the electron spins of both two molecules are stored before and after energy transfer, energy transfer by the Dexter mechanism is allowed. Note that energy transfer through TTA has been mainly described using the Dexter mechanism.

Meanwhile, the rate constant $k_{ET}$ of energy transfer in the Förster mechanism is expressed by Formula (1) below.

$$k_{ET} = \frac{9000c^4 \ln 10}{128\pi^5 n^4 N_A \tau_0^6} \frac{\kappa^2}{R^6} \int f_a(\tilde{v}) \varepsilon_b(v) \frac{d\tilde{v}}{\tilde{v}^4} \quad (1)$$

c: The velocity of light, n: refractive index, $N_A$: Avogadro number, $\tau_0$: donor duration, R: intermolecular distance, $K^2$: relative orientation factor of transition dipole moments of A and B, $\tilde{v}$: wave number, f: light intensity per wave number standardized to Area 1, ε: absorption coefficient Note that $\tau_0$ in Formula (1) is the reciprocal number of radiation speed $k_r$. Here, x is expressed as follows.

$$x = \frac{9000c^4 \ln 10}{128\pi^5 n^4 N_A} \frac{K^2}{R^6} \int f_a(\tilde{v})\varepsilon_b(v)\frac{d\tilde{v}}{\tilde{v}^4}$$

Formula (1) can be represented by Formula (1') using x.

$$k_{ET} = xk_r \quad (1')$$

Furthermore, energy transfer efficiency $\phi_{ET}$ by the Förster mechanism is represented by Formula (2) below.

$$\phi_{ET} = \frac{k_{ET}}{k_r + k_{nr} + k_{ET}} \quad (2)$$

$k_r$: radiative rate constant, $k_{nr}$: non-radiative rate constant

Formula (2') can be derived from Formula (2) and Formula (1') as follows.

$$\phi_{ET} = \frac{xk_r}{k_r + k_{nr} + xk_r} \quad (2')$$

$$= \frac{x}{\left(\frac{k_r + k_{nr}}{k_r}\right) + x}$$

$$= \frac{x}{\left(\frac{1}{\phi_p}\right) + x}$$

$\phi_p$: phosphorescence quantum efficiency

In the case where the molecule A and the molecule B are anthracene derivatives, a radiation rate constant ($k_r$) of phosphorescent emission obtained from the anthracene derivatives is $1 \times 10^3$ (s$^{-1}$) to $1 \times 10^4$ (s$^{-1}$) and a non-radiation rate constant ($k_{nr}$) thereof is $1 \times 10^7$ (s$^{-1}$) to $1 \times 10^8$ (s$^{-1}$). Accordingly, the phosphorescence quantum efficiency ($\phi_p$) can be estimated to be $1 \times 10^{-3}$ to $1 \times 10^{-5}$.

Here, when the phosphorescence quantum efficiency ($\phi_p$) is $1 \times 10^{-4}$ and x is 100, the energy transfer efficiency ($\phi_{ET}$) is 1.0%. If x is 1000, the energy transfer efficiency ($\phi_{ET}$) is 9.1%. Note that there is a positive correlation between x and an absorption coefficient; thus, as the absorption coefficient is increased, x is also increased. That is, even in the case where the phosphorescence quantum efficiency ($\phi_p$) of the molecule on a donor side (the molecule B in FIGS. 1A to 1D) is low, if the absorption coefficient of the molecule on an acceptor side (the molecule A in FIGS. 1A to 1D) is high, the energy transfer by the Förster mechanism can occur.

As described above, energy transfer between triplet excitons can partly occur by the Förster mechanism. Thus, here, the energy transfer through TTA by not only the Dexter mechanism but also that by the Förster mechanism are considered.

In the case where the energy transfer by the Förster mechanism is caused, as shown in the following Formula (3), generally, the absorption coefficient of the molecule is high when the oscillator strength (f) of the molecule is large.

$$f = 4.32 \times 10^{-9} \int \varepsilon(\tilde{v}) d\tilde{v} \quad (3)$$

f: oscillator strength, $\varepsilon$: absorption coefficient

Hence, a molecular design is performed using quantum chemical calculations so that the oscillator strength (f) between the triplet excited state ($T_1$) that is the lowest level and the triplet excited state ($T_n$) that is higher than the $T_1$ is increased. However, in the case where there is a plurality of triplet excited states ($T_n$) that is higher than $T_1$, the total of the oscillator strengths in the triplet excited states is considered to be the oscillator strength (f). Note that by the molecular design, it is found that the oscillator strength (f) of the molecule is increased when a compound including an anthracene skeleton is used. Structural formulae of the compounds each including an anthracene skeleton are shown below.

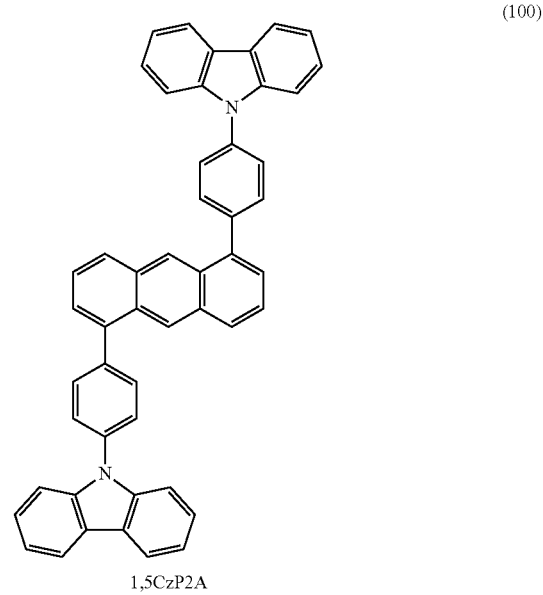 [SMILES: c1cc(-c2ccc(-n3c4ccccc4c4ccccc43)cc2)c2cc3cccc(-c4ccc(-n5c6ccccc6c6ccccc65)cc4)c3cc2c1]

1,5CzP2A

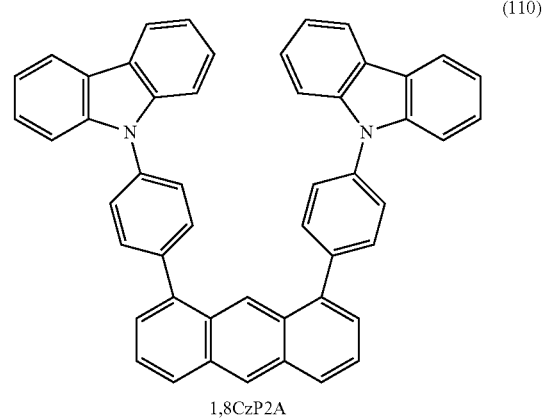

1,8CzP2A

The quantum chemical calculation method of the above compound is as follows. Note that Gaussian 09 is used as the quantum chemistry computational program. A high performance computer (ICE X manufactured by SGI Japan, Ltd.) is used for the calculation.

First, stable structures and electron states in the singlet ground state ($S_0$) and the $T_1$ state are calculated using the density functional theory (DFT). After that, vibration analysis is conducted, and the $T_1$ level is calculated from the energy difference between the stable structures in the $S_0$ state and in the $T_1$ state. As a basis function, 6-311G (d,p) is used. As a functional, B3LYP is used. In the DFT, the total energy of the molecules is represented as the sum of potential energy, electrostatic energy between electrons, electronic kinetic energy, and exchange-correlation energy including all the complicated interactions between electrons. Also in the DFT, an exchange-correlation interaction is approximated by a functional (a function of another function) of one electron potential represented in terms of electron density; thus, electron states can be obtained with high accuracy.

Next, a time-dependent density functional theory (TD-DFT) is used to calculate the transition dipole moment and the oscillator strength (f) which relate to the transition from the $T_1$ level to the $T_n$ level. As a basis function, 6-311G(d,p) is used, and as a functional, CAM-B3LYP is used. In the calculation using TD-DFT, stable structures and electron states in the $T_1$ state obtained from the calculation using CAM-B3LYP as a functional of DFT are used.

Note that a $T_n$ state in TD-DFT indicates a triplet excited state at an energy level lower than a value obtained by adding 0.6 eV to excitation energy corresponding to twice the $T_1$ level by the calculation using TD-DFT. However, even if an excited state satisfying the above condition is included in a portion other than an anthracene skeleton in the compound including the anthracene skeleton, it is excluded from the $T_n$ state because of being not involved in triplet excitation of the entire compound.

From the calculation using TD-DFT, the $T_1$ level of 1,5CzP2A is 1.67 eV and the $T_1$ level of 1,8CzP2A is 1.66 eV. From the calculation using TD-DFT, it is found that there are two triplet excited states corresponding to the $T_n$ levels where excitation energy from the $T_1$ level is less than a value obtained by adding 0.6 eV to the $T_1$ level in each of 1,5CzP2A and 1,8CzP2A. Note that excitation energies from the $T_1$ level to the $T_n$ level in 1,5CzP2A are 1.80 eV and 2.07 eV, and excitation energies from the $T_1$ level to the $T_n$ level in 1.8CzP2A was 1.81 eV and 2.06 eV.

Figure 2:
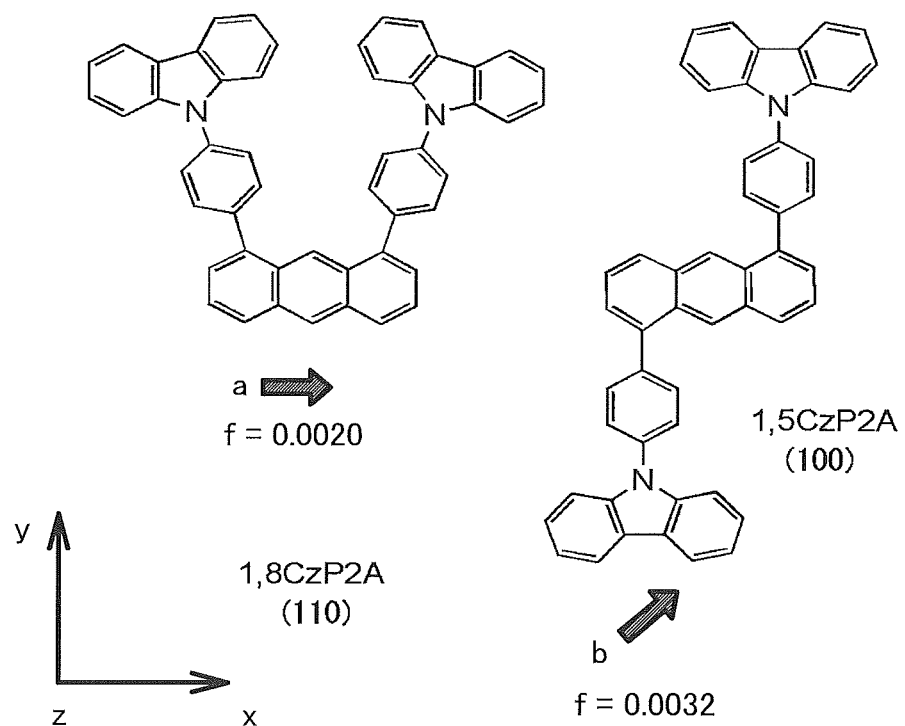
FIG. 2 shows the directions of transition dipole moments and oscillator strengths in molecular structures.

FIG. 2 shows the directions of the transition dipole moment between the $T_1$ level to the $T_n$ level and the oscillator strengths (f) of each of 1,5CzP2A and 1,8CzP2A, obtained from the calculation using TD-DFT. Note that in the molecular arrangement of the molecules in FIG. 2, the major axis of the anthracene skeleton is aligned with the x-axis and the minor axis is aligned with the y-axis.

As shown in FIG. 2, the transition dipole moment of 1,8CzP2A is formed mainly using components in the X-axis direction (an arrow "a" in FIG. 2); the transition dipole moment of 1,5CzP2A is formed using components in the X-axis direction and Y-axis direction (an arrow "b" in FIG. 2). Note that the oscillator strength (f) of 1,8CzP2A is calculated to be 0.0020, and the oscillator strength (f) of 1,5CzP2A is calculated to be 0.0032. The results reveals that the oscillator strength (f) of 1,5CzP2A is larger than that of 1,8CzP2A, and the transition between the $T_1$ level and the $T_n$ level more easily occurs in 1,5CzP2A than in 1,8CzP2A. That is, 1,5CzP2A has a higher probability of TTA caused by energy transfer by the Förster mechanism than 1,8CzP2A.

The magnitude of the transition dipole moment and the oscillator strength (f) have a relation shown in Formulae (4) in which the oscillator strength (f) is proportional to the square of the magnitude of the transition dipole moment.

$$f = \frac{|\mu_{mn}|^2}{|\mu_0|^2}$$

$$|\mu_0|^2 = \frac{3he^2}{8\pi m v}$$

(4)

f: oscillator strength, $\mu_{mn}$: transition dipole moment, $\mu_0$: oscillation electric dipole moment, h: Planck constant, e: quantum of electricity, m: mass of electrons, v: wave number In each of 1,5CzP2A and 1,8CzP2A, the compound is divided into an anthracene skeleton 501 and carbazole skeletons 502 as units (skeletons) constituting the compound, and the transition dipole moment in the transition from the $T_1$ level to the $T_n$ level in each of the units is analyzed. Here, only the transition between the main molecular orbits of the transition with the largest oscillator strength among the transitions from the $T_1$ level to the $T_n$ level, is analyzed. FIG. 3 shows the results.

From the results in FIG. 3, in 1,8CzP2A, the components of the two carbazole skeletons 502 in the y-axis direction of the transition dipole moment are in the direction opposite to each other, thereby weakening the components in the y-axis direction for each other. In 1,5CzP2A, the components of the two carbazole skeletons 502 in the y-axis direction of the transition dipole moment are in the same direction, thereby strengthening the components the y-axis direction for each other. As a result, in the entire 1,5CzP2A, the magnitude of the transition dipole moment in the y-axis direction derived from the carbazole skeletons 502 is large. Thus, as shown in the above Formulae (4), it is found that the oscillator strength (f) of 1,5CzP2A having a larger transition dipole moment is larger than that of 1,8CzP2A. That is, the following can be said, also in view of the molecular structure, that the oscillator strength (f) of 1,5CzP2A is larger than that of 1,8CzP2A, the transition between the $T_1$ level and the $T_n$ level more easily occurs in 1,5CzP2A than in 1,8CzP2A, and thus 1,5CzP2A has a higher probability of TTA caused by energy transfer by the Förster mechanism than 1,8CzP2A.

Note that the structure described in this embodiment can be combined as appropriate with any of the structures described in the other embodiments.

Embodiment 2

In this embodiment, an organic compound of one embodiment of the present invention will be described. The organic compound described in this embodiment is an organic compound in which the probability of TTA caused by energy transfer by the Förster mechanism can be increased, as in 1,5CzP2A and 1,8CzP2A described as examples in Embodiment 1.

The organic compound described in this embodiment has a feature in that a carbazole skeleton is bonded to an anthracene skeleton directly or through an arylene group. The organic compound described in this embodiment is an organic compound having a structure represented by General Formula (G1).

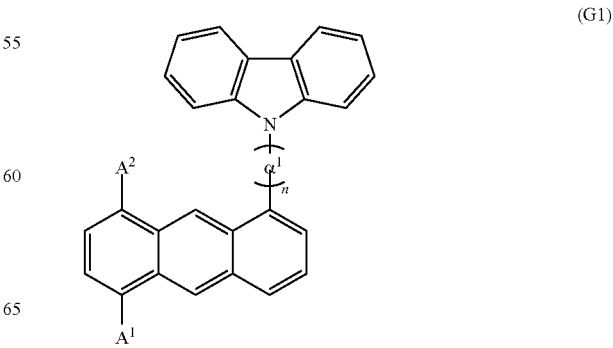

(G1)

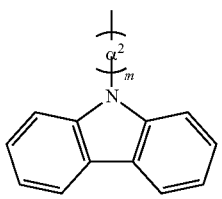

(G1-1)

Note that either of $A^1$ and $A^2$ in General Formula (G1) is a substituent represented by General Formula (G1-1), and the other is hydrogen or another substituent. That is, $\alpha^2$ is bonded to the 5-position or 8-position of the anthracene skeleton in General Formula (G1). In addition, $\alpha^1$ and $\alpha^2$ individually represent a substituted or unsubstituted phenylene group. Furthermore, n and m individually represent 1 or 2. Furthermore, General Formula (G1) may include one or more substituents. When General Formula (G1) includes the one or more substituents and either of $A^1$ and $A^2$ is the another substituent, they independently represent an alkyl group having 1 to 6 carbon atoms, a cycloalkyl group having 1 to 6 carbon atoms, an alkylphenyl group, or a phenyl group.

Note that as the substitution site of General Formula (G1-1), $A^1$ is preferred to $A^2$ in General Formula (G1) because the total of the oscillator strengths for excitation from the $T_1$ level to the $T_n$ level tends to be larger.

Furthermore, as the substitution site of General Formula (G1-1), $A^1$ is preferred to $A^2$ because the two substituents each including the carbazole skeleton are bonded to a 1-position and a 5-position of the anthracene skeleton, and steric repulsion of the two substituents each including the carbazole skeleton is prevented. Similarly, when General Formula (G1) has other substituents, it is preferable that the substituents be provided so as not to be adjacent (e.g., at the 1- and 2-positions, the 2- and 3-positions, and the 1- and 9-positions) to each other at the same time because the steric repulsion can be prevented.

Note that in General Formulae (G1) and (G1-1), examples of phenylene groups represented by $\alpha^1$ and $\alpha^2$ include a para-phenylene group, a meta-phenylene group, and an orthophenylene group.

Specific examples of the phenylene groups represented by $\alpha^1$ and $\alpha^2$ in General Formulae (G1) and (G1-1) are represented by Structural Formulae (α-1) to (α-5).

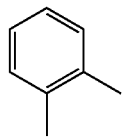

(α-3)

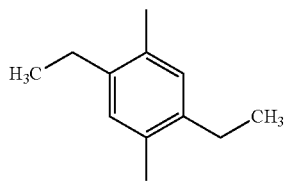

(α-4)

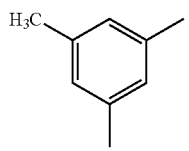

(α-5)

In the phenylene groups represented by $\alpha^1$ and $\alpha^2$ in General Formulae (G1) and (G1-1), the substitution sites of the carbazole skeleton and the anthracene skeleton can be any positions of a para-position, a meta-position, and an ortho-position. When the phenylene group has the substituents at the para-position, a high carrier-transport property is obtained, which is preferable. When the phenylene group has the substituents at the meta-position, a bulky structure is obtained and thus evaporation temperature can be low, which is preferable.

In the case where the phenylene groups represented by $\alpha^1$ and $\alpha^2$ in General Formulae (G1) and (G1-1) further have substituents, examples of the substituents include an alkyl group having 1 to 6 carbon atoms and a cycloalkyl group having 1 to 6 carbon atoms. Specific examples include a methyl group, an ethyl group, a propyl group, an isopropyl group, a butyl group, a tert-butyl group, a pentyl group, an isopentyl group, a hexyl group, an isohexyl group, and a cyclohexyl group.

Furthermore, specific examples of the substituents of the phenylene groups represented by $\alpha^1$ and $\alpha^2$ in General Formulae (G1) and (G1-1) are represented by Structural Formulae (R-1) to (R-11).

(α-1)

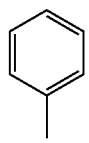

(R-1)

(α-2)

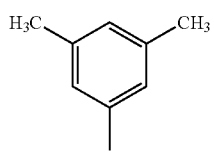

(R-2)

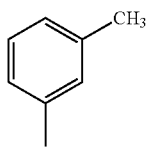 (R-3)

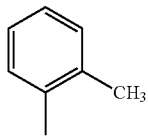 (R-4)

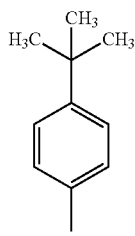 (R-5)

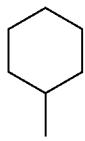 (R-6)

 (R-7)

 (R-8)

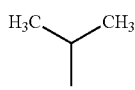 (R-9)

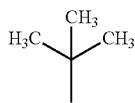 (R-10)

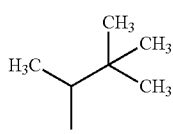 (R-11)

In the case where the phenylene groups represented by $\alpha^1$ and $\alpha^2$ in General Formulae (G1) and (G1-1) have the substituents, improvement in solubility and improvement in thermophysical property can be expected, which is preferable. Meanwhile, in the case where the phenylene groups represented by $\alpha^1$ and $\alpha^2$ in the General Formulae (G1) and (G1-1) do not have the substituents, synthesis is performed easily, which is preferable.

A structure of another organic compound is represented by General Formula (G2).

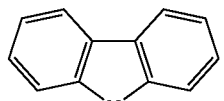 (G2)

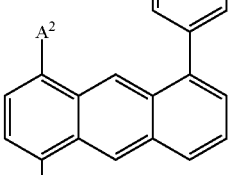

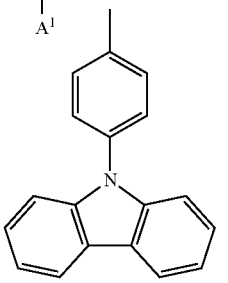

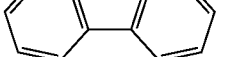 (G2-1)

Note that either of $A^1$ and $A^2$ in General Formula (G2) is a substituent represented by General Formula (G2-1), and the other is hydrogen or another substituent. Furthermore, General Formula (G2) may include one or more substituents. When General Formula (G2) includes the one or more substituents and either of $A^1$ and $A^2$ is the another substituent, they independently represent an alkyl group having 1 to 6 carbon atoms, a cycloalkyl group having 1 to 6 carbon atoms, an alkylphenyl group, or a phenyl group.

Specific examples of the structural formulae of the above-described organic compound are shown below. Note that the present invention is not limited to these examples.

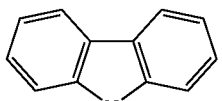 (100)

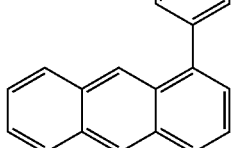

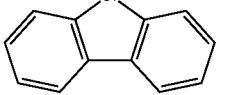

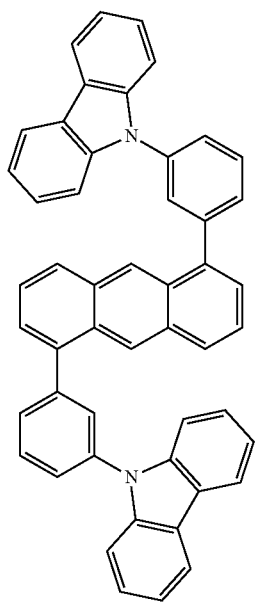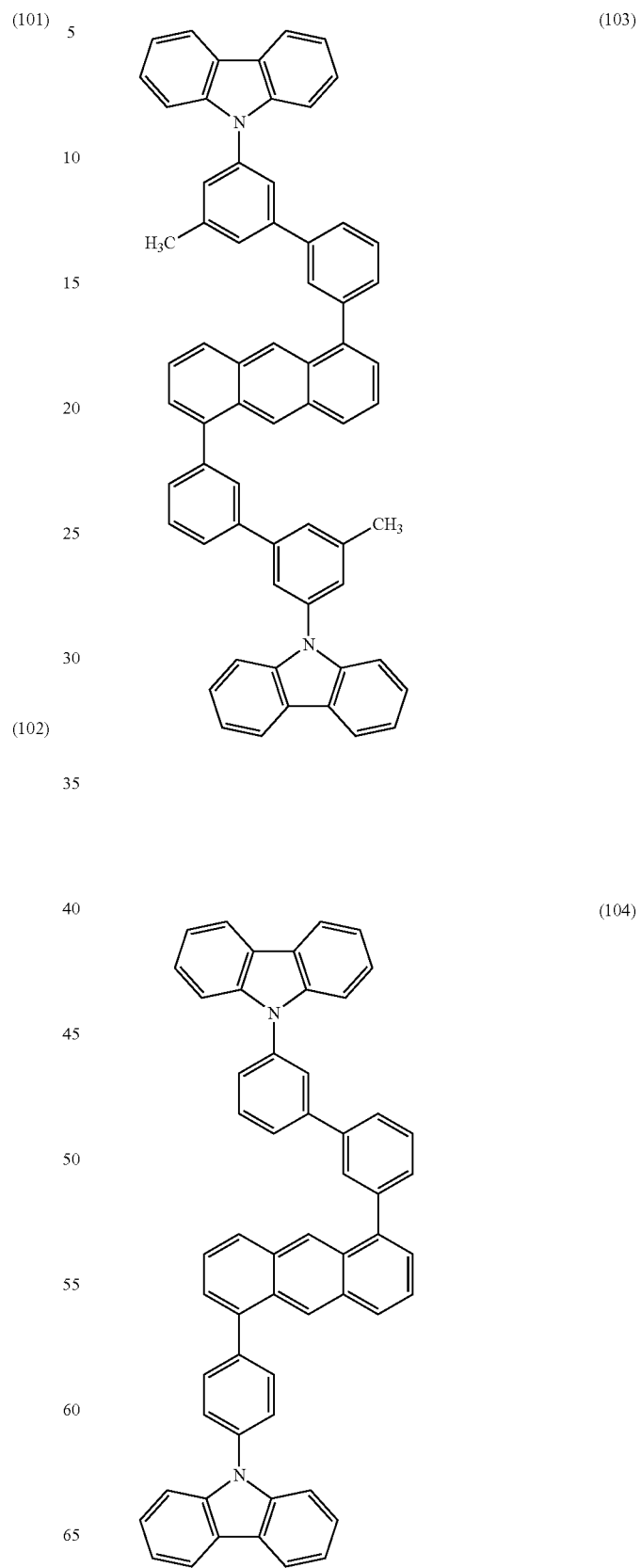

(105)
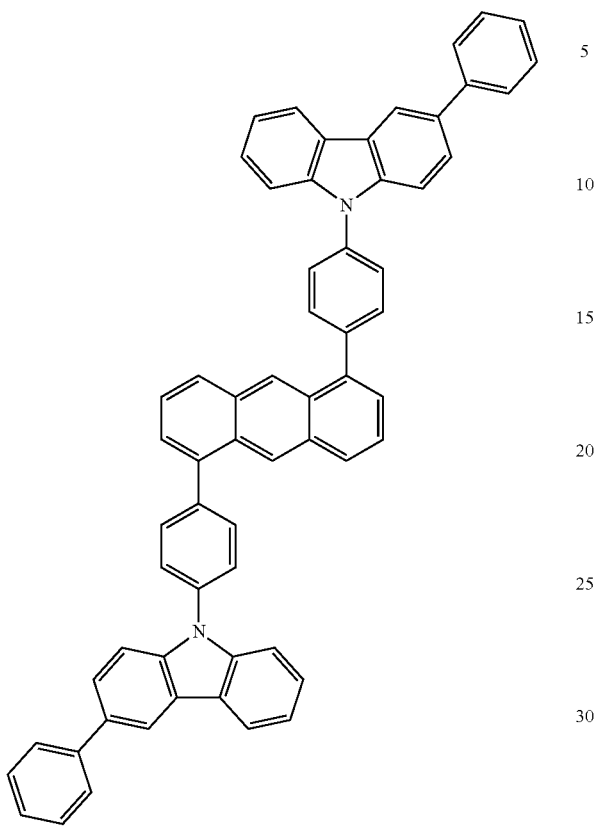
(106)
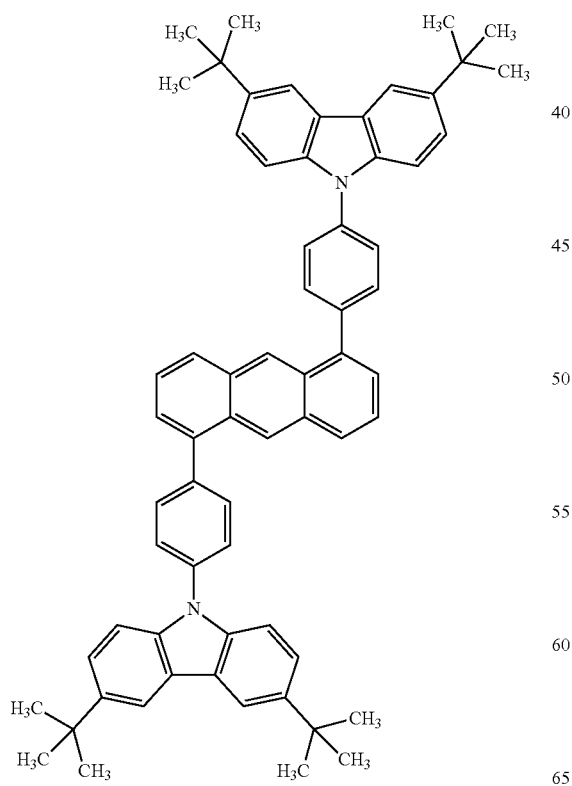
(107)
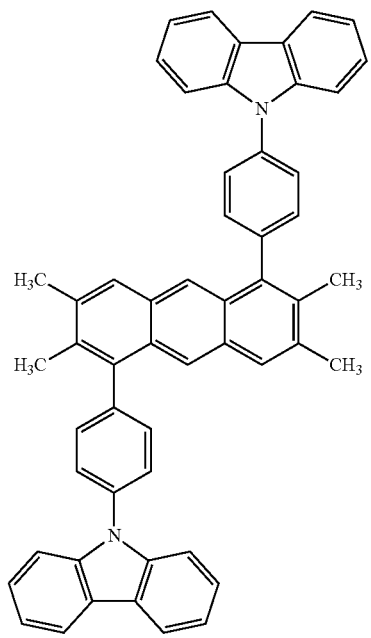
(108)
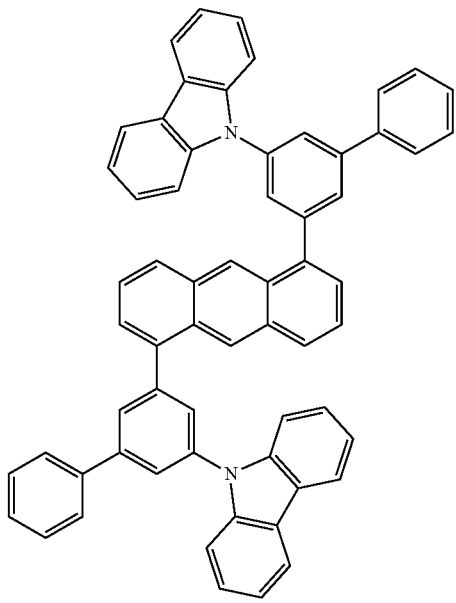

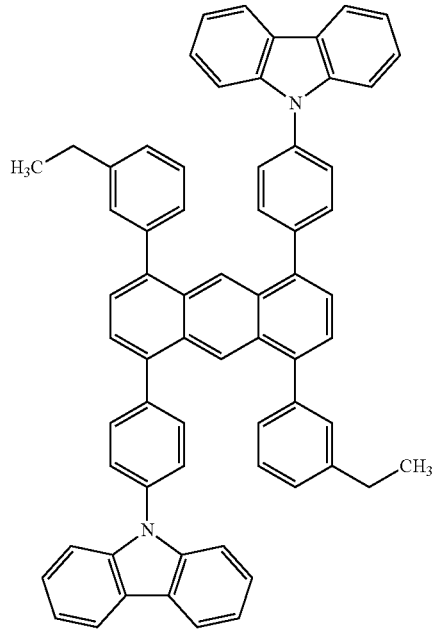
(109)
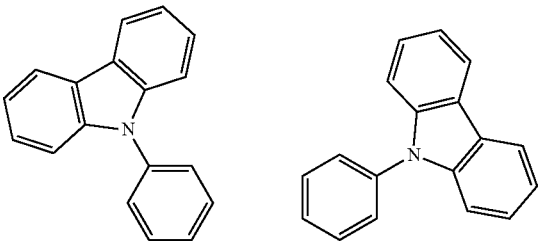
(112)
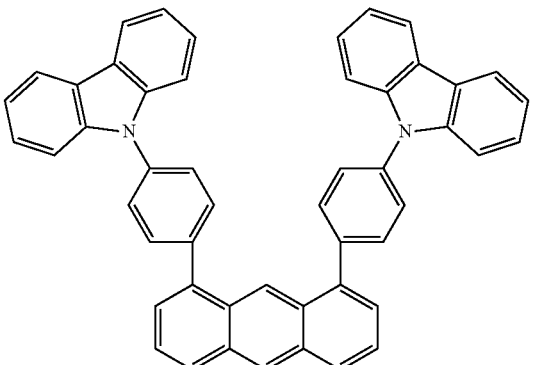
(113)
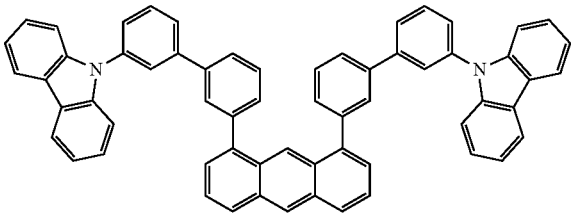
(114)
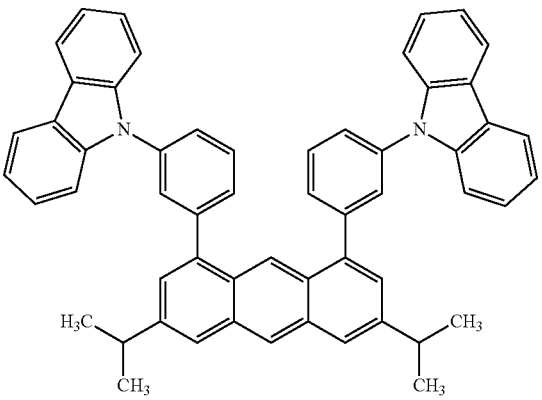
(115)
Examples of a method for synthesizing the organic compound represented by General Formula (G1) and General Formula (G1-1) are described referring to Synthesis Schemes (F1-1) and (F1-2). That is, by application of coupling reactions shown in Synthesis Schemes (F1-1) and (F1-2), the organic compound represented by General Formula (G1) and General Formula (G1-1) can be synthesized. As in the above case, either of $A^1$ and $A^2$ in General Formula (G1) is the substituent represented by General Formula (G1-1), and the other is hydrogen or another substituent.

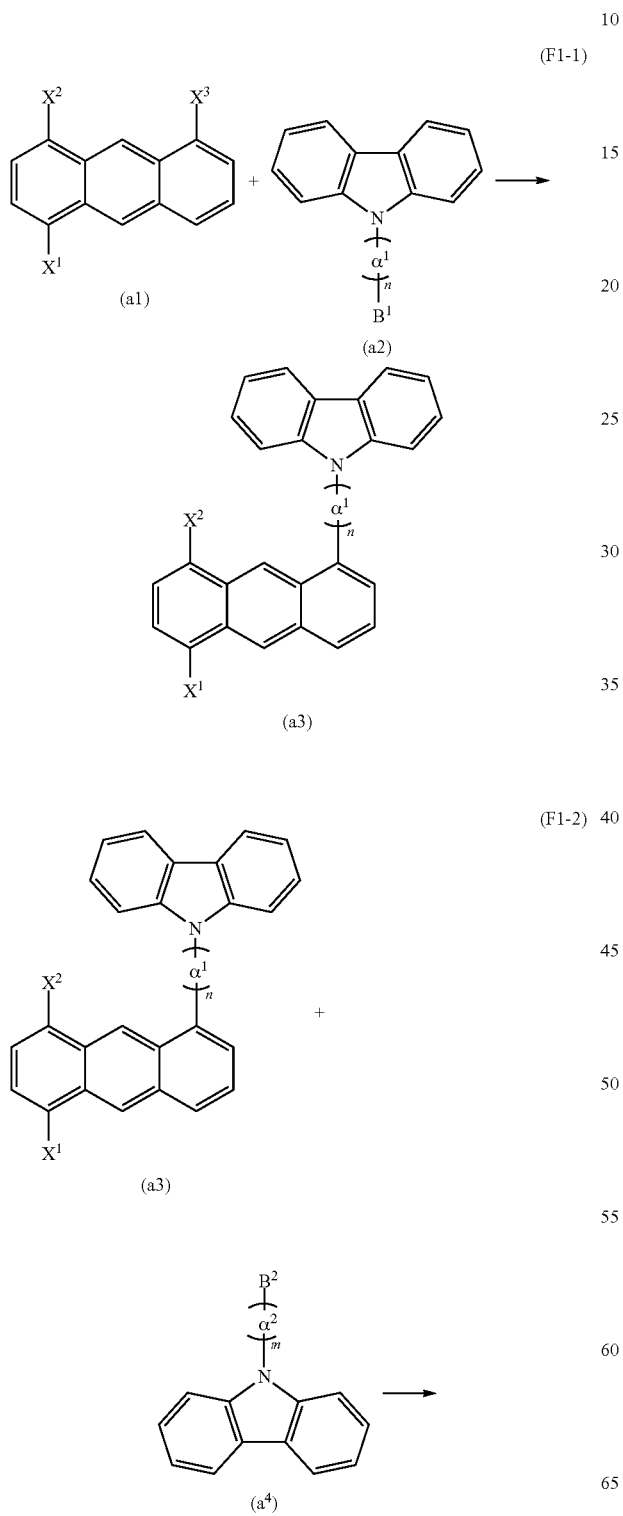

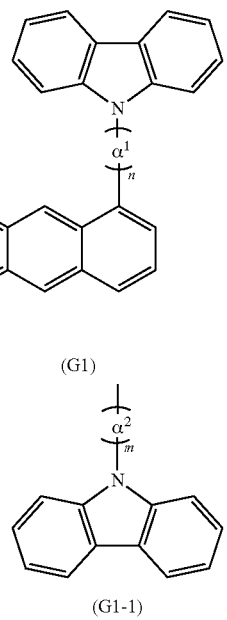

In Synthesis Schemes (F1-1) and (F1-2), either of $X^1$ and $X^2$ and $X^3$ represent halogen. Specifically, iodine, bromine, and chlorine have higher reactivity in this order and are preferred in this order. $B^1$ and $B^2$ each represent a boron compound; specifically, represent boronic acid or alkoxy boron. Note that an aryl aluminum compound, an aryl zirconium compound, an aryl zinc compound, an aryl tin compound, or the like may also be used. In addition, $\alpha^1$ and $\alpha^2$ individually represent a substituted or unsubstituted phenylene group. Note that n and m individually represent 1 or 2.

There are a variety of reaction conditions for the coupling reactions in Synthesis Schemes (F1-1) and (F1-2). As an example, a synthesis method using a metal catalyst in the presence of a base, such as a Suzuki-Miyaura reaction, can be employed. In the above synthesis method, the synthesis is carried out in two steps of a synthesis step represented by Synthesis Scheme (F1-1) and a synthesis step represented by Synthesis Scheme (F1-2). However, in the case where $\alpha^1$ in a compound (a2) and $\alpha^2$ in a compound (a4) are the same and n in the compound (a2) and m in the compound (a4) are the same, two or more equivalents of the compound (a2) may be added to the compound (a1), in which case the organic compound can be easily synthesized in one step.

Although the example of a method for synthesizing the organic compound is described above, the present invention is not limited thereto and any other synthesis method may be employed.

The above-described organic compound can be used alone or in combination with a light-emitting substance (guest), another organic compound, or the like in a light-emitting element.

In addition, the above-described organic compound can be used in an organic thin film solar cell. More specifically, the organic compound can be used in a carrier-transport layer or a carrier-injection layer since the organic compound has a carrier-transport property. In addition, a mixed layer of the organic compound and an acceptor substance can be used as a charge generation layer. The organic compound can be photoexcited and hence can be used for a power generation layer.

In Embodiment 2, one embodiment of the present invention has been described. Other embodiments of the present invention are described in Embodiments 3 to 12 as follows. Note that one embodiment of the present invention is not limited to the above examples. That is, since various embodiments of the present invention are disclosed in this embodiment and other embodiments, one embodiment of the present invention is not limited to a specific embodiment.

Embodiment 3

In Embodiment 3, a light-emitting element of the present invention will be described with reference to FIGS. 4A and 4B.

In the light-emitting element described in this embodiment, an EL layer 102 including a light-emitting layer 113 is provided between a pair of electrodes (a first electrode (anode) 101 and a second electrode (cathode) 103). The EL layer 102 includes, in addition to the light-emitting layer 113, a hole-injection layer 111, a hole-transport layer 112, an electron-transport layer 114, an electron-injection layer 115, and the like.

When a voltage is applied to the light-emitting element, holes injected from the first electrode 101 side and electrons injected from the second electrode 103 side recombine in the light-emitting layer 113; with energy generated by the recombination, a light-emitting substance such as an organometallic complex that is contained in the light-emitting layer 113 emits light.

The hole-injection layer 111 in the EL layer 102 can inject holes into the hole-transport layer 112 or the light-emitting layer 113 and can be formed of, for example, a substance having a high hole-transport property and a substance having an acceptor property, in which case electrons are extracted from the substance having a high hole-transport property by the substance having an acceptor property to generate holes. Thus, holes are injected from the hole-injection layer 111 into the light-emitting layer 113 through the hole-transport layer 112. For the hole-injection layer 111, a substance having a high hole-injection property can also be used. For example, molybdenum oxide, vanadium oxide, ruthenium oxide, tungsten oxide, manganese oxide, or the like can be used. Alternatively, the hole-injection layer 111 can be formed using a phthalocyanine-based compound such as phthalocyanine (abbreviation: $H_2Pc$) and copper phthalocyanine (CuPc), an aromatic amine compound such as 4,4'-bis[N-(4-diphenylaminophenyl)-N-phenylamino]biphenyl (abbreviation: DPAB) and N,N'-bis{4-[bis(3-methylphenyl)amino]phenyl}-N,N'-diphenyl-(1,1'-biphenyl)-4,4'-diamine (abbreviation: DNTPD), or a high molecular compound such as poly(3,4-ethylenedioxythiophene)/poly(styrenesulfonic acid) (abbreviation: PEDOT/PSS).

A preferred specific example in which the light-emitting element described in this embodiment is fabricated is described below.

For the first electrode (anode) 101 and the second electrode (cathode) 103, a metal, an alloy, an electrically conductive compound, a mixture thereof, and the like can be used. Specific examples are indium oxide-tin oxide (indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti). In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), and an alloy containing such an element (MgAg or AlLi); a rare earth metal such as europium (Eu) or ytterbium (Yb) and an alloy containing such an element; a graphene compound such as graphene or graphene oxide; and the like can be used. The first electrode (anode) 101 and the second electrode (cathode) 103 can be formed by, for example, a sputtering method or an evaporation method (including a vacuum evaporation method).

As the substance having a high hole-transport property which is used for the hole-injection layer 111 and the hole-transport layer 112, any of a variety of organic compounds such as aromatic amine compounds, carbazole derivatives, aromatic hydrocarbons, and high molecular compounds (e.g., oligomers, dendrimers, or polymers) can be used. The organic compound used for the composite material is preferably an organic compound having a high hole-transport property. Specifically, a substance having a hole mobility of $1 \times 10^{-6}$ $cm^2/Vs$ or more is preferably used. The layer formed using the substance having a high hole-transport property is not limited to a single layer and may be formed by stacking two or more layers. Organic compounds that can be used as the substance having a hole-transport property are specifically given below.

The substance used for the hole-transport layer 112 preferably has higher $S_1$ and $T_1$ levels than the light-emitting layer 113 that is adjacent to the hole-transport layer 112 because diffusion of excitation energy to the hole-transport layer 112 can be suppressed. Furthermore, the substance used for the hole-transport layer 112 preferably has a higher LUMO level (a larger value) than the light-emitting layer 113 that is adjacent to the hole-transport layer 112 because passage of electrons through the light-emitting layer 113 to the hole-transport layer 112 can be suppressed. Furthermore, a HOMO level of the substance used for the hole-transport layer 112 is preferably deeper (a smaller value) than or substantially equal to the HOMO level of the light-emitting layer 113 that is adjacent to the hole-transport layer 112 because easier hole-injection into the light-emitting layer 113 can be achieved. Organic compounds that can be used as the substance having a hole-transport property are specifically given below.

Examples of the aromatic amine compounds are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), DNTPD, 1,3,5-tris[N-(4-diphenylaminophenyl)-N-phenylamino]benzene (abbreviation: DPA3B), 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris(carbazol-9-yl)triphenylamine (abbreviation: TCTA), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB), and the like.

Specific examples of carbazole derivatives are 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like. Other examples are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene, and the like.

Examples of aromatic hydrocarbons are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthypanthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Besides, pentacene, coronene, or the like can also be used. The aromatic hydrocarbon which has a hole mobility of $1 \times 10^{-6}$ cm$^2$/Vs or more and which has 14 to 42 carbon atoms is particularly preferable. The aromatic hydrocarbons may have a vinyl skeleton. Examples of the aromatic hydrocarbon having a vinyl group are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

A high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can also be used.

Examples of the substance having an acceptor property which is used for the hole-injection layer 111 and the hole-transport layer 112 are compounds having an electron-withdrawing group (a halogen group or a cyano group) such as 7,7,8,8-tetracyano-2,3,5,6-tetrafluoroquinodimethane (abbreviation: F$_4$-TCNQ), chloranil, and 2,3,6,7,10,11-hexacyano-1,4,5,8,9,12-hexaazatriphenylene (HAT-CN). In particular, a compound in which electron-withdrawing groups are bonded to a condensed aromatic ring having a plurality of heteroatoms, like HAT-CN, is thermally stable and preferable. Oxides of metals belonging to Groups 4 to 8 of the periodic table can be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in the air, has a low hygroscopic property, and is easy to handle.

The light-emitting layer 113 is a layer containing a light-emitting substance (guest material). Examples of the light-emitting substance include a light-emitting substances that convert singlet excitation energy into luminescence and light-emitting substances that convert triplet excitation energy into luminescence. In the case of a structure in which triplet excitons are converted into singlet excitons by TTA so that emission efficiency of the singlet excitons is improved as described in Embodiment 1, a light-emitting substance that converts singlet excitation energy into luminescence is preferably used. As an example of the light-emitting substance that converts singlet excitation energy into luminescence, a substance that emits fluorescence (fluorescent compound) can be given.

Examples of the substance that emits fluorescence are N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N'''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-α]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and the like.

In the case where the light-emitting substance that converts triplet excitation energy into luminescence is used in the light-emitting layer 113, it is preferable that an organic compound (a host material) used with a light-emitting substance (referred to as a dopant or a guest material) have a higher probability of TTA. Specifically, an organic compound where the total of oscillator strengths (f) for transitions from the $T_1$ level of the organic compound to some $T_n$ levels which are each higher than the $T_1$ level by less than 0.6 eV is 0.0015 or more, preferably 0.0020 or more is preferably used. That is, an organic compound in which the transition between the $T_1$ level and the $T_n$ level easily occurs, and which has a higher probability of TTA caused by energy transfer by the Förster mechanism, is preferably used. As an example of the organic compound which has a higher probability of TTA, the organic compound described in Embodiment 2 can be used.

In the case where the light-emitting substance that converts triplet excitation energy into luminescence is used in the light-emitting element 113, it seems that when the organic compound (the host material) used with the light-emitting substance (the dopant) is designed such that the $T_1$ level of the organic compound (the host material) is the lowest, the triplet excitation energy is collected at the host material and thus the probability of TTA is increased.

Furthermore, in the light-emitting layer 113 of the light-emitting element in this embodiment, not only a structure in which a substance that emits fluorescence (a fluorescence compound) is used for a light-emitting substance by utilizing TTA, but also a structure in which a light-emitting substance that converts triplet excitation energy into luminescence can be used together with the substance that emits fluorescence (a fluorescence compound). Examples of the light-emitting substance that converts triplet excitation energy into luminescence include a substance which emits phosphorescence (a phosphorescent compound) and a thermally activated delayed fluorescent (TADF) material which emits thermally activated delayed fluorescence. Note that "delayed fluorescence" exhibited by the TADF material refers to light emission having the same spectrum as normal fluorescence and an extremely long lifetime. The lifetime is $1\times10^{-6}$ seconds or longer, preferably $1\times10^{-3}$ seconds or longer.

Examples of the substance that emits phosphorescence are bis {2-[3',5'-bis(trifluoromethyl)phenyl]pyridinato-N, $C^{2'}$}iridium(III) picolinate (abbreviation: [Ir(CF$_3$ppy)$_2$(pic)], bis[2-(4',6'-difluorophenyl)pyridinato-N,$C^{2'}$]iridium (III) acetylacetonate (abbreviation: FIracac), tris(2-phenylpyridinato)iridium(III) (abbreviation: [Ir(ppy)$_3$]), bis (2-phenylpyridinato)iridium(III) acetylacetonate (abbreviation: [Ir(ppy)$_2$(acac)]), tris(acetylacetonato) (monophenanthroline)terbium(III) (abbreviation: [Tb(acac)$_3$(Phen)]), bis(benzo[h]quinolinato)iridium(III) acetylacetonate (abbreviation: [Ir(bzq)$_2$(acac)]), bis(2,4-diphenyl-1,3-oxazolato-N,$C^{2'}$)iridium(III) acetylacetonate (abbreviation: [Ir(dpo)$_2$(acac)]), bis{2-[4'-(perfluorophenyl) phenyl]pyridinato-N,$C^{2'}$}iridium(III) acetylacetonate (abbreviation: [Ir(p-PF-ph)$_2$(acac)]), bis(2-phenylbenzothiazolato-N,$C^{2'}$)iridium(III) acetylacetonate (abbreviation: [Ir(bt) $_2$(acac)]), bis[2-(2'-benzo[4,5-α]thienyl)pyridinato-N,$C^{3'}$] iridium(III) acetylacetonate (abbreviation: [Ir(btp)$_2$(acac)]), bis(1-phenylisoquinolinato-N,$C^{2'}$)iridium(III) acetylacetonate (abbreviation: [Ir(piq)$_2$(acac)]), (acetylacetonato)bis[2, 3-bis(4-fluorophenyl)quinoxalinato]iridium(III) (abbreviation: [Ir(Fdpq)$_2$(acac)]), (acetylacetonato)bis(3,5-dimethyl-2-phenylpyrazinato)iridium(III) (abbreviation: [Ir(mppr-Me)$_2$(acac)]), (acetylacetonato)bis(5-isopropyl-3-methyl-2-phenylpyrazinato)iridium(III) (abbreviation: [Ir(mppr-iPr)$_2$(acac)]), (acetylacetonato)bis(2,3,5-triphenylpyrazinato) iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)], (acetylacetonato)bis(6-tert-butyl-4-phenylpyrimidinato)iridium(III) (abbreviation: [Ir (tBuppm)$_2$(acac)]), (acetylacetonato)bis(4,6-diphenylpyrimidinato)iridium(III) (abbreviation: [Ir(dppm)$_2$(acac)]), 2,3,7,8,12,13,17,18-octaethyl-21H,23H-porphyrin platinum (II) (abbreviation: PtOEP), tris(1,3-diphenyl-1,3-propanedionato)(monophenanthroline)europium(III) (abbreviation: [Eu(DBM)$_3$(Phen)]), tris[1-(2-thenoyl)-3,3,3-trifluoroacetonato](monophenanthroline)europium(III) (abbreviation: [Eu (TTA)$_3$(Phen)]), and the like.

Examples of the TADF material are fullerene, a derivative thereof, an acridine derivative such as proflavine, eosin, and the like. Other examples are a metal-containing porphyrin, such as a porphyrin containing magnesium (Mg), zinc (Zn), cadmium (Cd), tin (Sn), platinum (Pt), indium (In), or palladium (Pd). Examples of the metal-containing porphyrin are a protoporphyrin-tin fluoride complex (abbreviation: SnF$_2$(Proto IX)), a mesoporphyrin-tin fluoride complex (abbreviation: SnF$_2$(Meso IX)), a hematoporphyrin-tin fluoride complex (abbreviation: SnF$_2$(Hemato IX)), a coproporphyrin tetramethyl ester-tin fluoride complex (abbreviation: SnF$_2$(Copro III-4Me)), an octaethylporphyrin-tin fluoride complex (abbreviation: SnF$_2$(OEP)), an etioporphyrin-tin fluoride complex (abbreviation: SnF$_2$(Etio I)), an octaethylporphyrin-platinum chloride complex (abbreviation: PtCl$_2$OEP), and the like. Alternatively, a heterocyclic compound including a π-electron rich heteroaromatic ring and a π-electron deficient heteroaromatic ring can be used, such as 2-(biphenyl-4-yl)-4,6-bis(12-phenylindolo[2,3-α]carbazol-11-yl)-1,3,5-triazine (abbreviation: PIC-TRZ). Note that a material in which the π-electron rich heteroaromatic ring is directly bonded to the π-electron deficient heteroaromatic ring is particularly preferably used because the donor property of the π-electron rich heteroaromatic ring and the acceptor property of the π-electron deficient heteroaromatic ring are both increased and the energy difference between the S1 level and the T1 level becomes small.

When the light-emitting substance that converts triplet excitation energy into luminescence is used in the light-emitting layer 113, other than a structure in which one kind of organic compound (host material) is used in addition to the light-emitting substance, the following structure may be employed: a structure where two kinds of organic compounds (the two kinds of organic compounds may include the above host material) that can form an excited complex (also called an exciplex) at the time of recombination of carriers (electrons and holes) in the light-emitting layer 113 are contained in addition to the light-emitting substance. In order to form an excited complex efficiently, it is particularly preferable to combine a compound which easily accepts electrons (a material having an electron-transport property) and a compound which easily accepts holes (a material having a hole-transport property). In the case where the combination of a material having an electron-transport property and a material having a hole-transport property is used as a host material which forms an excited complex as described above, the carrier balance between holes and electrons in the light-emitting layer can be easily optimized by adjustment of the mixture ratio of the material having an electron-transport property and the material having a hole-transport property. The optimization of the carrier balance between holes and electrons in the light-emitting layer can prevent a region in which electrons and holes are recombined from existing on one side in the light-emitting layer. By preventing the region in which electrons and holes are recombined from existing to one side, the reliability of the light-emitting element can be improved.

As the material having an electron-transport property that is preferably used to form the above excited complex, a π-electron deficient heteroaromatic compound such as a nitrogen-containing heteroaromatic compound, a metal complex, or the like can be used. Specific examples include a metal complex such as bis(10-hydroxybenzo[h]quinolinato)beryllium(II) (abbreviation: BeBq$_2$), bis(2-methyl-8-quinolinolato) (4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ); a heterocyclic compound having an polyazole skeleton such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-1H-benzimidazole) (abbreviation: TPBI), or 2-[3-(dibenzothiophen-4-yl)phenyl]-1-phenyl-1H-benzimidazole (abbreviation: mDBTBIm-II); a heterocyclic compound having a diazine skeleton such as 2-[3-(dibenzothiophen-4-yl)phenyl]dibenzo[f,h]quinoxaline (abbreviation: 2mDBTP-DBq-II), 2-[3'-(dibenzothiophen-4-yl)biphenyl-3-yl]dibenzo[f,h]quinoxaline (abbreviation: 2mDBTPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II); 6-[3-(dibenzothiophen-4-yl)phenyl]dibenzo[f,h]quinoxaline (abbreviation: 6mDBTPDBq-II), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), or 4,6-bis[3-(9H-carbazol-9-yl)phenyl]pyrimidine (abbreviation: 4,6mCzP2Pm); a heterocyclic compound having a triazine skeleton such as 2-{4-[3-(N-phenyl-9H-carbazol-3-yl)-9H-carbazol-9-yl]phenyl}-4,6-diphenyl-1,3,5-triazine (abbreviation: PCCzPTzn); and a heterocyclic compound having a pyridine skeleton such as 3,5-bis[3-(9H-carbazol-9-yl)phenyl]pyridine (abbreviation: 35DCzPPy) or 1,3,5-tri[3-(3-pyridyl)phenyl]benzene (abbreviation: TmPyPB). Among the above materials, heterocyclic compounds having diazine skeletons and triazine skeletons and heterocyclic compounds having pyridine skeletons have high reliability and are thus preferable. Heterocyclic compounds having diazine (pyrimidine or pyrazine) skeletons and triazine skeletons have an excellent electron-transport property and contribute to a decrease in drive voltage.

As the compound that is preferably used to form the above excited complex, a π-electron rich heteroaromatic compound (e.g., a carbazole derivative or an indole derivative), an aromatic amine compound, or the like can be favorably used. Specific examples are compounds having aromatic amine skeletons, such as 2-[N-(9-phenylcarbazol-3-yl)-N-phenylamino]spiro-9,9'-bifluorene (abbreviation: PCASF), 4,4',4"-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N'-diphenyl-benzene-1,3-diamine (abbreviation: PCA2B), N-(9,9-dimethyl-2-diphenylamino-9H-fluoren-7-yl)diphenylamine (abbreviation: DPNF), N,N',N"-triphenyl-N,N',N"-tris(9-phenylcarbazol-3-yl)benzene-1,3,5-triamine (abbreviation: PCA3B), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), NPB, N,N'-bis(3-methylphenyl)-N,N'-diphenyl-[1,1'-biphenyl]-4,4'-diamine (abbreviation: TPD), 4,4'-bis[N-(4-diphenylaminophenyl)-N-phenylamino]biphenyl (abbreviation: DPAB), BSPB, 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), PCzPCA1, 3-[N-(4-diphenylaminophenyl)-N-phenylamino]-9-phenyl carbazole (abbreviation: PCzDPA1), 3,6-bis[N-(4-diphenylaminophenyl)-N-phenylamino]-9-phenylcarbazole (abbreviation: PCzDPA2), DNTPD, 3,6-bis[N-(4-diphenylaminophenyl)-N-(1-naphthyl)amino]-9-phenylcarbazole (abbreviation: PCzTPN2), PCzPCA2, 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 3-[N-(1-naphthyl)-N-(9-phenylcarbazol-3-yl)amino]-9-phenylcarbazole (abbreviation: PCzPCN1), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), N-(4-biphenyl)-N-(9,9-dimethyl-9H-fluoren-2-yl)-9-phenyl-9H-carbazol-3-amine (abbreviation: PCBiF), and N-(1,1'-biphenyl-4-yl)-N-[4-(9-phenyl-9H-carbazol-3-yl)phenyl]-9,9-dimethyl-9H-fluoren-2-amine (abbreviation: PCBBiF); compounds having carbazole skeletons, such as 1,3-bis(N-carbazolyl)benzene (abbreviation: mCP), CBP, 3,6-bis(3,5-diphenylphenyl)-9-phenylcarbazole (abbreviation: CzTP), and 9-phenyl-9H-3-(9-phenyl-9H-carbazol-3-yl)carbazole (abbreviation: PCCP); compounds having thiophene skeletons, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having furan skeletons, such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compounds having aromatic amine skeletons and the compounds having carbazole skeletons are preferred because these compounds are highly reliable and have an excellent hole-transport property and contribute to a reduction in drive voltage.

Figure 4A:
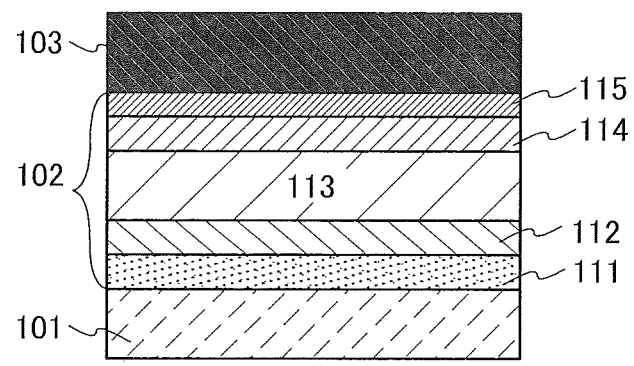
FIGS. 4A and 4B each illustrate a structure of a light-emitting element.
Figure 4B:
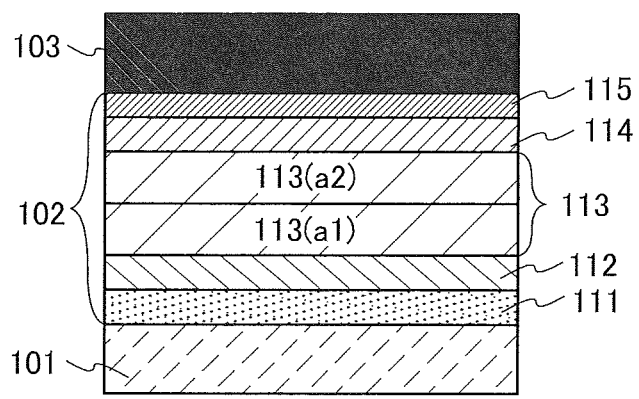

In the light-emitting element, the light-emitting layer 113 does not necessarily have the single-layer structure illustrated in FIG. 4A and may have a stacked-layer structure including two or more layers as illustrated in FIG. 4B. In that case, each layer in the stacked-layer structure emits light. For example, fluorescence utilizing TTA is obtained from a first light-emitting layer 113(a1), and phosphorescence is obtained from a second light-emitting layer 113(a2) stacked over the first light-emitting layer. Note that the stacking order may be reversed. It is preferable that light emission due to energy transfer from an excited complex to a dopant be obtained from the layer that emits phosphorescence. The emission color of one layer and that of the other layer may be the same or different. In the case where the emission colors are different, a structure in which, for example, blue light from one layer and orange, yellow light, or the like from the other layer can be obtained can be formed. Each layer may contain various kinds of dopants.

Note that in the case where the light-emitting layer 113 has a stacked-layer structure, a light-emitting substance converting singlet excitation energy into light emission or a light-emitting substance converting triplet excitation energy into light emission can be used alone or in combination, for example. In that case, the following substances can be used.

The electron-transport layer 114 is a layer containing a substance having a high electron-transport property (also referred to as an electron-transport compound). For the electron-transport layer 114, a metal complex such as tris(8-quinolinolato)aluminum (abbreviation: Alq$_3$), tris(4-methyl-8-quinolinolato)aluminum (abbreviation: Almq$_3$), BeBq$_2$, BAlq, bis[2-(2-hydroxyphenyl)benzoxazolato]zinc (abbreviation: Zn(BOX)$_2$), or bis[2-(2-hydroxyphenyl)benzothiazolato]zinc (abbreviation: Zn(BTZ)$_2$) can be used. Alternatively, a heteroaromatic compound such as PBD, TAZ, 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), or 4,4'-bis(5-methylbenzoxazol-2-yl)stilbene (abbreviation: BzOs) can also be used. A high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can also be used. The substances listed here are mainly ones that have an electron mobility of $1 \times 10^{-6}$ cm$^2$/Vs or more. Note that any substance other than the substances listed here may be used for the electron-transport layer 114 as long as the electron-transport property is higher than the hole-transport property.

The substance used for the electron-transport layer 114 preferably has higher $S_1$ and $T_1$ levels than the light-emitting layer 113 that is adjacent to the electron-transport layer 114 because diffusion of excitation energy to the electron-transport layer 114 can be prevented. Furthermore, the substance used for the electron-transport layer 114 preferably has a deeper HOMO level (a smaller value) than the light-emitting layer 113 adjacent to the electron-transport layer 114 because passage of holes through the light-emitting layer 113 to the electron-transport layer 114 can be suppressed. Furthermore, a LUMO level of the substance used for the electron-transport layer 114 is preferably higher (a larger value) than or substantially equal to the LUMO level of the light-emitting layer 113 that is adjacent to the electron-transport layer 114 because easier electron-injection into the light-emitting layer 113 can be achieved.

The electron-transport layer 114 is not limited to a single layer, but may be a stack of two or more layers each containing any of the substances listed above.

The electron-injection layer 115 is a layer containing a substance having a high electron-injection property. For the electron-injection layer 115, an alkali metal, an alkaline earth metal, or a compound thereof such as lithium fluoride (LiF), cesium fluoride (CsF), calcium fluoride (CaF$_2$), or lithium oxide (LiO$_x$) can be used. A rare earth metal compound like erbium fluoride (ErF$_3$) can also be used. An electride may also be used for the electron-injection layer 115. Examples of the electride include a substance in which electrons are added at high concentration to calcium oxide-aluminum oxide. Any of the substances for forming the electron-transport layer 114, which are given above, can be used.

A composite material in which an organic compound and an electron donor (donor) are mixed may also be used for the electron-injection layer 115. Such a composite material is excellent in an electron-injection property and an electron-transport property because electrons are generated in the organic compound by the electron donor. In this case, the organic compound is preferably a material that is excellent in transporting the generated electrons. Specifically, for example, the substances for forming the electron-transport layer 114 (e.g., a metal complex or a heteroaromatic compound), which are given above, can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, and the like are given. In addition, an alkali metal oxide or an alkaline earth metal oxide is preferable, and lithium oxide, calcium oxide, barium oxide, and the like are given. A Lewis base such as magnesium oxide can also be used. An organic compound such as tetrathiafulvalene (abbreviation: TTF) can also be used.

Note that each of the hole-injection layer 111, the hole-transport layer 112, the light-emitting layer 113, the electron-transport layer 114, and the electron-injection layer 115 can be formed by any one or any combination of the following methods: an evaporation method (including a vacuum evaporation method), a printing method (such as relief printing, intaglio printing, gravure printing, planography printing, and stencil printing), an ink-jet method, a coating method, and the like. Besides the above-mentioned materials, an inorganic compound such as a quantum dot or a high molecular compound (e.g., an oligomer, a dendrimer, or a polymer) may be used for the hole-injection layer 111, the hole-transport layer 112, the light-emitting layer 113, the electron-transport layer 114, and the electron-injection layer 115, which are described above.

In the above light-emitting element, current flows due to a potential difference applied between the first electrode 101 and the second electrode 103 and holes and electrons recombine in the EL layer 102, whereby light is emitted. Then, the emitted light is extracted outside through one or both of the first electrode 101 and the second electrode 103. Therefore, one or both of the first electrode 101 and the second electrode 103 are electrodes having a light-transmitting property.

As described above, in the light-emitting element of this embodiment, the characteristics of the light-emitting element can be improved by the use of the above-described desired structure for a light-emitting layer. Specifically, when TTA is utilized, light efficiency due to singlet excitation energy can be improved, whereby the light-emitting element can have higher efficiency than a conventional fluorescent light-emitting element.

Note that the structure described in this embodiment can be used in combination with any of the structures described in the other embodiments, as appropriate.

Embodiment 4

In this embodiment, a light-emitting element (hereinafter referred to as a tandem light-emitting element) including a plurality of EL layers is described.

Figure 5A:
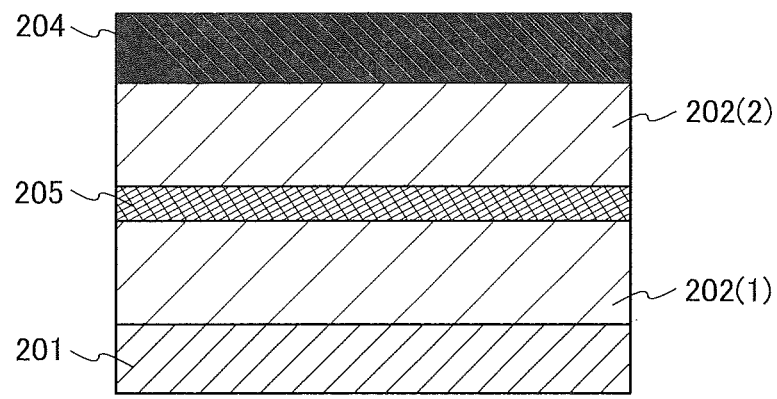
FIGS. 5A and 5B each illustrate a structure of a light-emitting element.

A light-emitting element described in this embodiment is a tandem light-emitting element including, between a pair of electrodes (a first electrode 201 and a second electrode 204), a plurality of EL layers (a first EL layer 202(1) and a second EL layer 202(2)) and a charge-generation layer 205 provided therebetween, as illustrated in FIG. 5A.

In this embodiment, the first electrode 201 functions as an anode, and the second electrode 204 functions as a cathode. Note that the first electrode 201 and the second electrode 204 can have structures similar to those described in Embodiment 3. In addition, either or both of the EL layers (the first EL layer 202(1) and the second EL layer 202(2)) may have structures similar to those described in Embodiment 3. In other words, the structures of the first EL layer 202(1) and the second EL layer 202(2) may be the same as or different from each other. When the structures are the same, Embodiment 3 can be referred to.

The charge-generation layer 205 provided between the plurality of EL layers (the first EL layer 202(1) and the second EL layer 202(2)) has a function of injecting electrons into one of the EL layers and injecting holes into the other of the EL layers when a voltage is applied between the first electrode 201 and the second electrode 204. In this embodiment, when a voltage is applied such that the potential of the first electrode 201 is higher than that of the second electrode 204, the charge-generation layer 205 injects electrons into the first EL layer 202(1) and injects holes into the second EL layer 202(2).

Note that in terms of light extraction efficiency, the charge-generation layer 205 preferably has a property of transmitting visible light (specifically, the charge-generation layer 205 has a visible light transmittance of 40% or more). The charge-generation layer 205 functions even when it has lower conductivity than the first electrode 201 or the second electrode 204.

The charge-generation layer 205 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, the substances having a high hole-transport property which are given in Embodiment 3 as the substances used for the hole-injection layer 111 and the hole-transport layer 112 can be used. For example, an aromatic amine compound such as NPB, TPD, TDATA, MTDATA, or BSPB, or the like can be used. The substances listed here are mainly ones that have a hole mobility of $1\times10^{-6}$ cm$^2$/Vs or more. Note that any organic compound other than the compounds listed here may be used as long as the hole-transport property is higher than the electron-transport property.

As the electron acceptor, 7,7,8,8-tetracyano-2,3,5,6-tetrafluoroquinodimethane (abbreviation: F$_4$-TCNQ), chloranil, and the like can be given. Oxides of metals belonging to Groups 4 to 8 of the periodic table can also be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in the air, has a low hygroscopic property, and is easy to handle.

In the case of the structure in which an electron donor is added to an organic compound having a high electron-transport property, as the organic compound having a high electron-transport property, the substances having a high electron-transport property which are given in Embodiment 3 as the substances used for the electron-transport layer 114 can be used. For example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$, can be used. Alternatively, in addition to such a metal complex, PBD, OXD-7, TAZ, Bphen, BCP, or the like can be used. The substances listed here are mainly ones that have an electron mobility of $1\times10^{-6}$ cm$^2$/Vs or more. Note that any organic compound other than the compounds listed here may be used as long as the electron-transport property is higher than the hole-transport property.

As the electron donor, it is possible to use an alkali metal, an alkaline earth metal, a rare earth metal, metals belonging to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that forming the charge-generation layer 205 by using any of the above materials can suppress a drive voltage increase caused by the stack of the EL layers. The charge-generation layer 205 can be formed by any one or any combination of the following methods: an evaporation method (including a vacuum evaporation method), a printing method (such as relief printing, intaglio printing, gravure printing, planography printing, and stencil printing), an ink-jet method, a coating method, and the like.

Figure 5B:
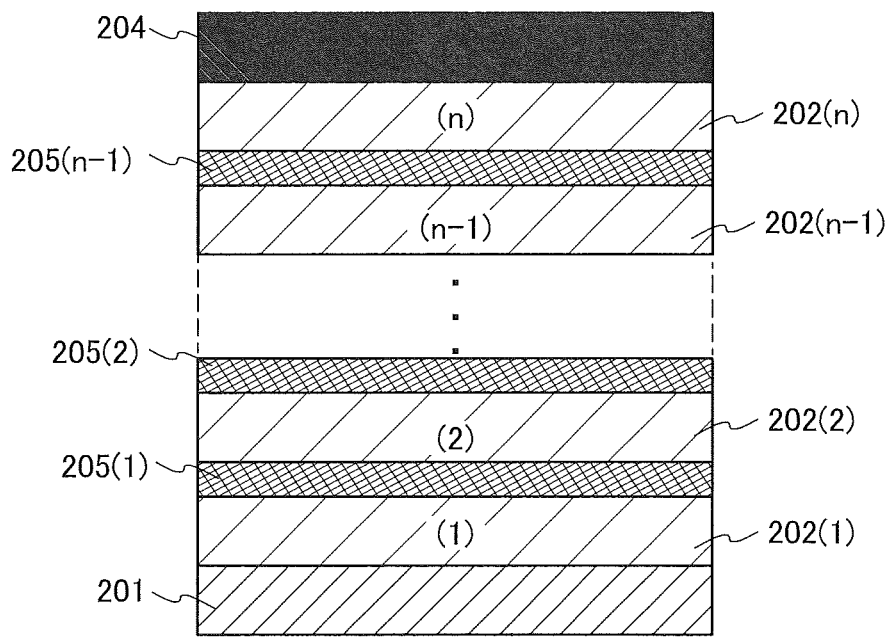

Although the light-emitting element including two EL layers is described in this embodiment, the present invention can be similarly applied to a light-emitting element in which n EL layers (202(1) to 202(n)) (n is three or more) are stacked as illustrated in FIG. 5B. In the case where a plurality of EL layers are included between a pair of electrodes as in the light-emitting element according to this embodiment, by providing charge-generation layers (205(1) to 205(n−1)) between the EL layers, light emission in a high luminance region can be obtained with current density kept low. Since the current density can be kept low, the element can have a long lifetime.

When the EL layers have different emission colors, a desired emission color can be obtained from the whole light-emitting element. For example, in a light-emitting element having two EL layers, when an emission color of the first EL layer and an emission color of the second EL layer are complementary colors, the light-emitting element can emit white light as a whole. Note that "complementary colors" refer to colors that can produce an achromatic color when mixed. In other words, mixing light of complementary colors allows white light emission to be obtained. Specifically, a combination in which blue light emission is obtained from the first EL layer and yellow or orange light emission is obtained from the second EL layer is given as an example. In that case, it is not necessary that both of blue light emission and yellow (or orange) light emission are fluorescence, and the both are not necessarily phosphorescence. For example, a combination in which blue light emission is fluorescence and yellow (or orange) light emission is phosphorescence or a combination in which blue light emission is phosphorescence and yellow (or orange) light emission is fluorescence may be employed.

The same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in the other embodiments.

Embodiment 5

In this embodiment, a light-emitting device will be described.

The light-emitting device may be either a passive matrix light-emitting device or an active matrix light-emitting device. Any of the light-emitting elements described in other embodiments can be used in the light-emitting device described in this embodiment.

In this embodiment, first, an active matrix light-emitting device is described with reference to FIGS. 6A to 6C.

Figure 6A:
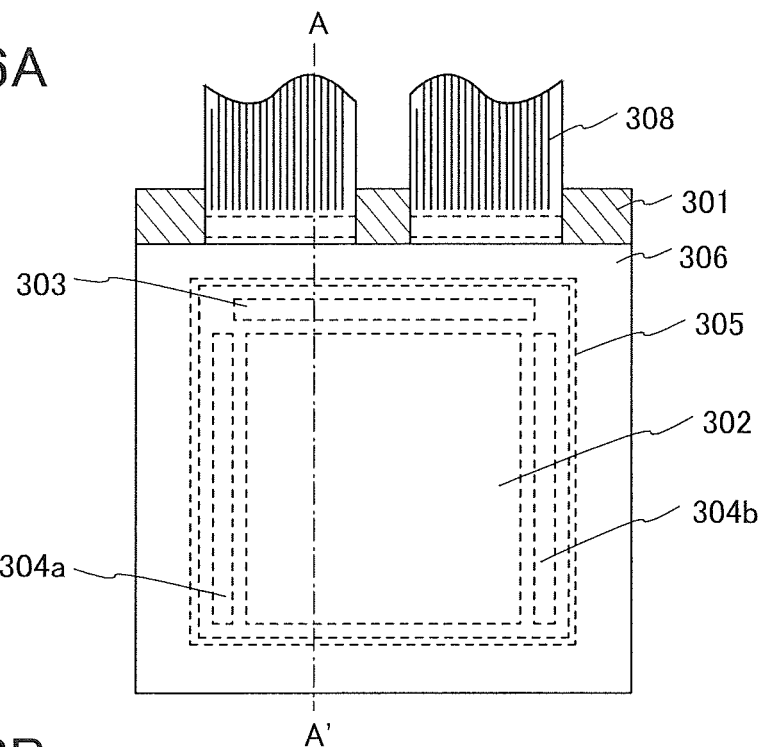
FIGS. 6A to 6C illustrate a light-emitting device.
Figure 6B:
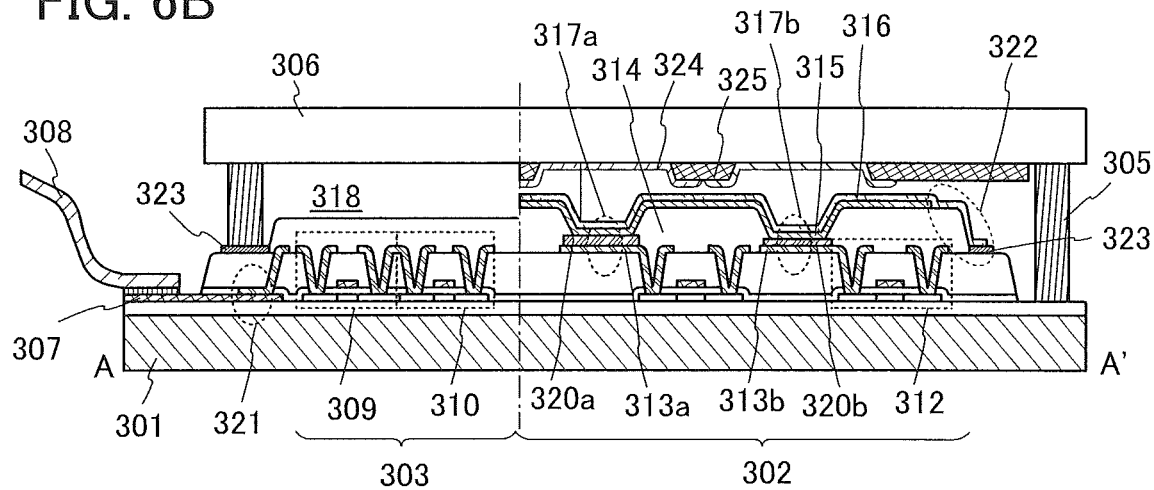

Note that FIG. 6A is a top view illustrating a light-emitting device and FIG. 6B is a cross-sectional view taken along the chain line A-A' in FIG. 6A. The light-emitting device of this embodiment includes a pixel portion 302 provided over an element substrate 301, a driver circuit portion (a source line driver circuit) 303, and driver circuit portions (gate line driver circuits) 304a and 304b. The pixel portion 302, the driver circuit portion 303, and the driver circuit portions 304a and 304b are sealed between the element substrate 301 and a sealing substrate 306 with a sealant 305.

In addition, over the element substrate 301, a lead wiring 307 for connecting an external input terminal, through which a signal (e.g., a video signal, a clock signal, a start signal, or a reset signal) or an potential from the outside is transmitted to the driver circuit portion 303 and the driver circuit portions 304a and 304b, is provided. Here, an example is described in which a flexible printed circuit (FPC) 308 is provided as the external input terminal. Although only the FPC is illustrated here, the FPC may be provided with a printed wiring board (PWB). The light-emitting device in this specification includes, in its category, not only the light-emitting device itself but also the light-emitting device provided with the FPC or the PWB.

Next, a cross-sectional structure is described with reference to FIG. 6B. The driver circuit portions and the pixel portion are formed over the element substrate 301; the driver circuit portion 303 that is the source line driver circuit and the pixel portion 302 are illustrated here.

The driver circuit portion 303 is an example in which FETs 309 and 310 are combined. Note that the driver circuit portion 303 may be formed with a circuit including transistors having the same conductivity type (either n-channel transistors or p-channel transistors) or a CMOS circuit including an n-channel transistor and a p-channel transistor. Although this embodiment shows a driver integrated type in which the driver circuit is formed over the substrate, the driver circuit is not necessarily formed over the substrate, and may be formed outside the substrate.

The pixel portion 302 includes a switching FET (not illustrated) and a current control FET 312, and a wiring of the current control FET 312 (a source electrode or a drain electrode) is electrically connected to a first electrode (anode) (313a or 313b) of a light-emitting element 317a or 317b. Although the pixel portion 302 includes two kinds of FETs (the switching FET and the current control FETs 312) in this embodiment, one embodiment of the present invention is not limited thereto. The pixel portion 302 may include, for example, three or more kinds of FETs and a capacitor in combination.

As the FETs 309, 310, and 312, for example, a staggered transistor or an inverted staggered transistor can be used. Examples of a semiconductor material that can be used for the FETs 309, 310, and 312 are a Group 13 semiconductor, a Group 14 semiconductor (e.g., silicon), a compound semiconductor, an oxide semiconductor, and an organic semiconductor. In addition, there is no particular limitation on the crystallinity of the semiconductor material, and an amorphous semiconductor or a crystalline semiconductor can be used. In particular, an oxide semiconductor is preferably used for the FETs 309, 310, and 312. Examples of the oxide semiconductor are In—Ga oxides, In-M-Zn oxides (M is Al, Ga, Y, Zr, La, Ce, Hf, or Nd), and the like. For example, an oxide semiconductor material that has an energy gap of 2 eV or more, preferably 2.5 eV or more and further preferably 3 eV or more, is used, so that the off-state current of the transistors can be reduced.

In addition, conductive films (320a and 320b) for optical adjustment are stacked over the first electrodes 313a and 313b. For example, as illustrated in FIG. 6B, in the case where the wavelengths of light extracted from the light-emitting elements 317a and 317b are different from each other, the thicknesses of the conductive films 320a and 320b are different from each other. In addition, an insulator 314 is formed to cover end portions of the first electrodes (313a and 313b). In this embodiment, the insulator 314 is formed using a positive photosensitive acrylic resin. The first electrodes (313a and 313b) are used as the anodes in this embodiment.

The insulator 314 preferably has a curved surface with curvature at an upper end portion or a lower end portion thereof. This enables favorable coverage by a film to be formed over the insulator 314. The insulator 314 can be formed using, for example, either a negative photosensitive resin or a positive photosensitive resin. The material for the insulator 314 is not limited to an organic compound and an inorganic compound such as silicon oxide, silicon oxynitride, or silicon nitride can also be used.

An EL layer 315 and a second electrode 316 are stacked over the first electrodes (313a and 313b). In the EL layer 315, at least a light-emitting layer is provided. In the light-emitting elements (317a and 317b) including the first electrodes (313a and 313b), the EL layer 315, and the second electrode 316, an end portion of the EL layer 315 is covered with the second electrode 316. The structure of the EL layer 315 may be the same as or different from the single-layer structure and the stacked layer structure described in Embodiments 2 and 3. Furthermore, the structure may differ between the light-emitting elements.

For the first electrode 313, the EL layer 315, and the second electrode 316, any of the materials given in Embodiment 3 can be used. The first electrodes (313a and 313b) of the light-emitting elements (317a and 317b) are electrically connected to the lead wiring 307 in a region 321, so that an external signal is input through the FPC 308. The second electrode 316 of the light-emitting elements (317a and 317b) is electrically connected to a lead wiring 323 in a region 322, so that an external signal is input through the FPC 308 although it is not illustrated.

Although the cross-sectional view in FIG. 6B illustrates only the two light-emitting elements 317, a plurality of light-emitting elements are arranged in a matrix in the pixel portion 302. Specifically, in the pixel portion 302, light-emitting elements that emit light of two kinds of colors (e.g., B and Y), light-emitting elements that emit light of three kinds of colors (e.g., R, G, and B), light-emitting elements that emit light of four kinds of colors (e.g. R, G, B, and Y) or (R, G, B, and W)), or the like are formed so that a light-emitting device capable of full color display can be obtained. In such cases, full color display may be achieved as follows: materials different according to the emission colors or the like of the light-emitting elements are used to form light-emitting layers (so-called separate coloring formation); alternatively, the plurality of light-emitting elements share one light-emitting layer formed using the same material and further include color filters. Thus, the light-emitting elements that emit light of a plurality of kinds of colors are used in combination, so that effects such as an improvement in color purity and a reduction in power consumption can be achieved. Furthermore, the light-emitting device may have improved emission efficiency and reduced power consumption by combination with quantum dots.

The sealing substrate 306 is attached to the element substrate 301 with the sealant 305, whereby the light-emitting elements 317a and 317b are provided in a space 318 surrounded by the element substrate 301, the sealing substrate 306, and the sealant 305.

The sealing substrate 306 is provided with coloring layers (color filters) 324, and a black layer (black matrix) 325 is provided between adjacent coloring layers. Note that one or both of the adjacent coloring layers (color filters) 324 may be provided so as to partly overlap with the black layer (black matrix) 325. Light emission obtained from the light-emitting elements 317a and 317b is extracted through the coloring layers (color filters) 324.

Note that the space 318 may be filled with an inert gas (such as nitrogen or argon) or the sealant 305. In the case where the sealant is applied for attachment of the substrates, one or more of UV treatment, heat treatment, and the like are preferably performed.

An epoxy-based resin or glass frit is preferably used for the sealant 305. The material preferably allows as little moisture and oxygen as possible to penetrate. As the sealing substrate 306, a glass substrate, a quartz substrate, or a plastic substrate formed of fiber-reinforced plastic (FRP), poly(vinyl fluoride) (PVF), polyester, acrylic, or the like can be used. In the case where glass frit is used as the sealant, the element substrate 301 and the sealing substrate 306 are preferably glass substrates for high adhesion.

Figure 6C:
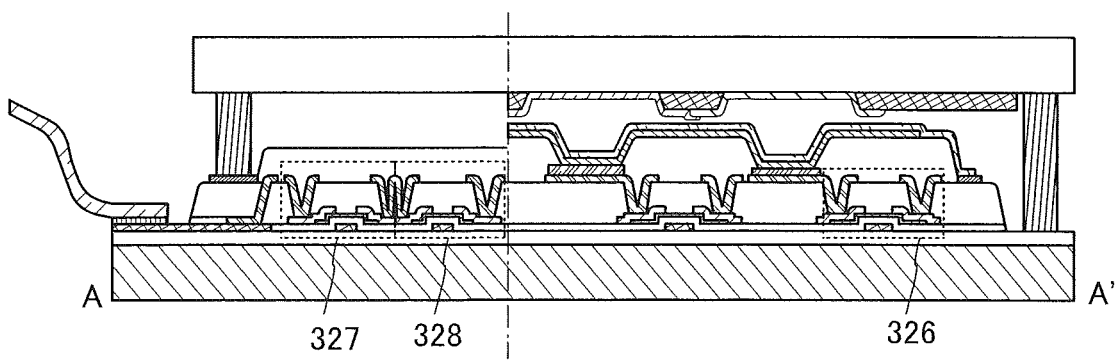

Structures of the FETs electrically connected to the light-emitting elements may be different from those in FIG. 6B in the position of a gate electrode; that is, the structures of FETs 326, 327, and 328 as illustrated in FIG. 6C may be employed. The coloring layer (color filter) 324 with which the sealing substrate 306 is provided may be provided as illustrated in FIG. 6C such that, at a position where the coloring layer (color filter) 324 overlaps with the black layer (black matrix) 325, the coloring layer (color filter) 324 further overlaps with an adjacent coloring layer (color filter) 324.

As described above, an active matrix light-emitting device can be obtained.

Note that the light-emitting device can be a passive matrix light-emitting device as well as the above active matrix light-emitting device.

Figure 7A:
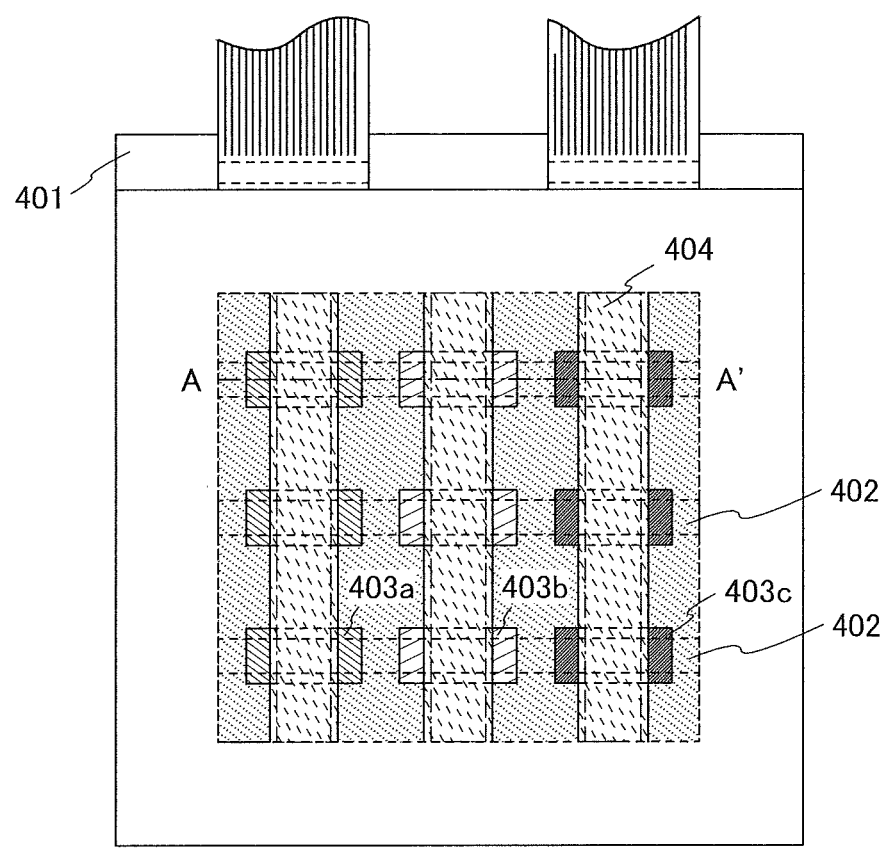
FIGS. 7A and 7B illustrate a light-emitting device.
Figure 7B:
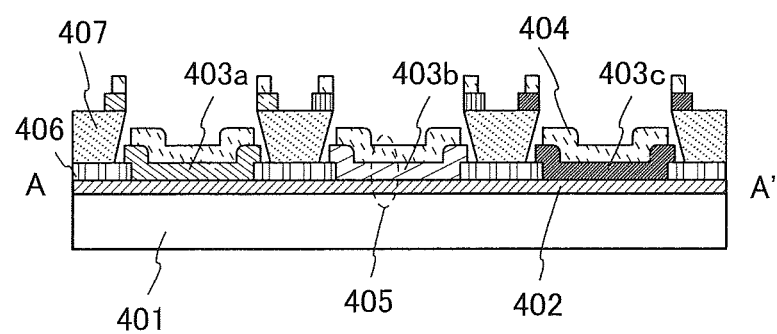

FIGS. 7A and 7B illustrate a passive-matrix light-emitting device. FIG. 7A is a top view of the passive-matrix light-emitting device, and FIG. 7B is a cross-sectional view thereof.

As illustrated in FIGS. 7A and 7B, light-emitting elements 405 including a first electrode 402, EL layers (403a, 403b, and 403c), and second electrodes 404 are formed over a substrate 401. Note that the first electrode 402 has an island-like shape, and a plurality of the first electrodes 402 are formed in one direction (the lateral direction in FIG. 7A) to form a striped pattern. An insulating film 406 is formed over part of the first electrode 402. A partition 407 formed using an insulating material is provided over the insulating film 406. The sidewalls of the partition 407 slope so that the distance between one sidewall and the other sidewall gradually decreases toward the surface of the substrate as illustrated in FIG. 7B.

Since the insulating film 406 has openings in part of the first electrode 402, the EL layers (403a, 403b, and 403c) and second electrodes 404 which are divided as desired can be formed over the first electrode 402. In the example in FIGS. 7A and 7B, a mask such as a metal mask and the partition 407 over the insulating film 406 are employed to form the EL layers (403a, 403b, and 403c) and the second electrodes 404. In this example, the EL layers 403a, 403b, and 403c emit light of different colors (e.g., red, green, blue, yellow, orange, and white).

After the formation of the EL layers (403a, 403b, and 403c), the second electrodes 404 are formed. Thus, the second electrode 404 is formed over the EL layers (403a, 403b, and 403c) without contact with the first electrode 402.

Note that sealing can be performed by a method similar to that used for the active matrix light-emitting device, and description thereof is not made.

As described above, the passive matrix light-emitting device can be obtained.

Note that in this specification and the like, a transistor or a light-emitting element can be formed using any of a variety of substrates, for example. The type of a substrate is not limited to a certain type. As the substrate, a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, a base material film, or the like can be used, for example. As an example of a glass substrate, a barium borosilicate glass substrate, an aluminoborosilicate glass substrate, a soda lime glass substrate, or the like can be given. Examples of the flexible substrate, the attachment film, the base film, and the like are substrates of plastics typified by polyethylene terephthalate (PET), polyethylene naphthalate (PEN), polyether sulfone (PES), and polytetrafluoroethylene (PTFE). Another example is a synthetic resin such as acrylic. Alternatively, polypropylene, polyester, polyvinyl fluoride, polyvinyl chloride, or the like can be used. Alternatively, polyamide, polyimide, aramid, epoxy, an inorganic vapor deposition film, paper, or the like can be used. Specifically, the use of semiconductor substrates, single crystal substrates, SOI substrates, or the like enables the manufacture of small-sized transistors with a small variation in characteristics, size, shape, or the like and with high current supply capability. A circuit using such transistors achieves low power consumption of the circuit or high integration of the circuit.

Alternatively, a flexible substrate may be used as the substrate, and a transistor or a light-emitting element may be provided directly on the flexible substrate. Still alternatively, a separation layer may be provided between the substrate and the transistor or the light-emitting element. The separation layer can be used when part or the whole of a semiconductor device formed over the separation layer is separated from the substrate and transferred onto another substrate. In such a case, the transistor or the light-emitting element can be transferred to a substrate having low heat resistance or a flexible substrate. For the separation layer, a stack including inorganic films, which are a tungsten film and a silicon oxide film, or an organic resin film of polyimide or the like formed over a substrate can be used, for example.

In other words, a transistor or a light-emitting element may be formed using one substrate, and then transferred to another substrate. Examples of a substrate to which a transistor or a light-emitting element is transferred are, in addition to the above-described substrates over which a transistor or a light-emitting element can be formed, a paper substrate, a cellophane substrate, an aramid film substrate, a polyimide film substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, a rubber substrate, and the like. When such a substrate is used, a transistor with excellent characteristics or a transistor with low power consumption can be formed, a device with high durability or high heat resistance can be provided, or a reduction in weight or thickness can be achieved.

Note that the structure described in this embodiment can be combined as appropriate with any of the structures described in the other embodiments.

Embodiment 6

In this embodiment, examples of a variety of electronic devices and an automobile manufactured using a light-emitting device which is one embodiment of the present invention are described.

Examples of the electronic device including the light-emitting device are television devices (also referred to as TV or television receivers), monitors for computers and the like, digital cameras, digital video cameras, digital photo frames, cellular phones (also referred to as portable telephone devices), portable game consoles, portable information terminals, audio playback devices, large game machines such as pachinko machines, and the like. Specific examples of the electronic devices are illustrated in FIGS. 8A, 8B, 8C, 8D, 8D'-1, and 8D'-2, and FIGS. 9A to 9C.

Figure 8A:
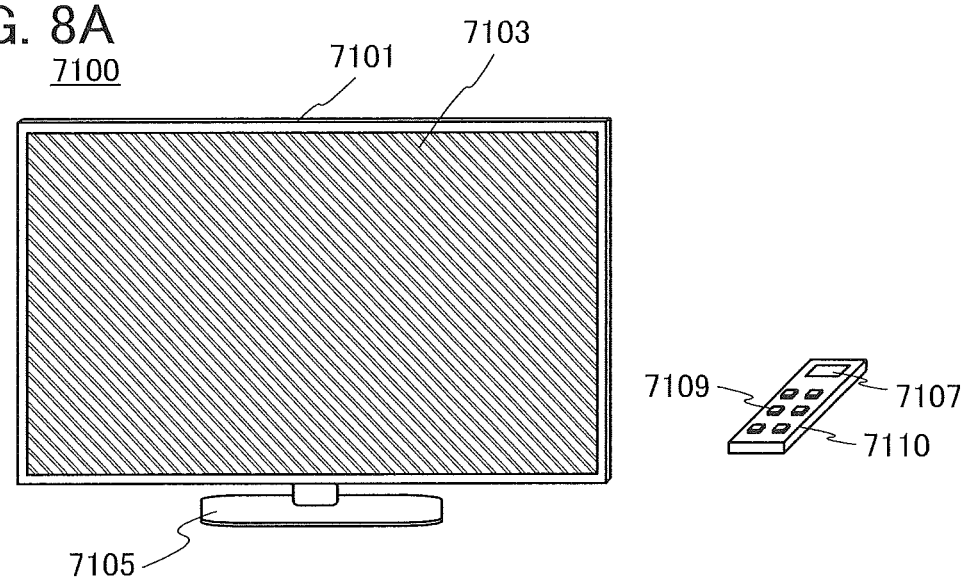
FIGS. 8A, 8B, 8C, 8D, 8D'-1 and 8D'-2 illustrate electronic devices.

FIG. 8A illustrates an example of a television device. In the television device 7100, a display portion 7103 is incorporated in a housing 7101. The display portion 7103 can display images and may be a touch panel (an input/output device) including a touch sensor (an input device). Note that the light-emitting device which is one embodiment of the present invention can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the use of the receiver, general television broadcasts can be received. Moreover, when the television device is connected to a communication network with or without wires via the modem, one-way (from a sender to a receiver) or two-way (between a sender and a receiver or between receivers) information communication can be performed.

Figure 8B:
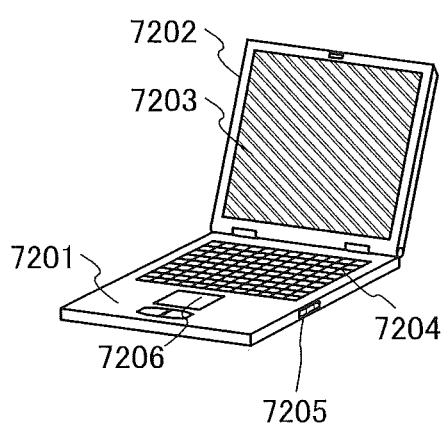

FIG. 8B illustrates a computer, which includes a main body 7201, a housing 7202, a display portion 7203, a keyboard 7204, an external connection port 7205, a pointing device 7206, and the like. Note that this computer can be manufactured using the light-emitting device which is one embodiment of the present invention for the display portion 7203. The display portion 7203 may be a touch panel (an input/output device) including a touch sensor (an input device).

Figure 8C:
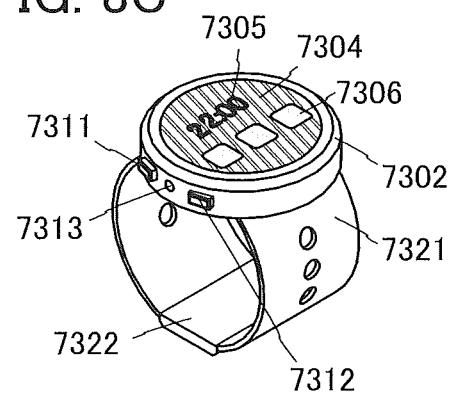

FIG. 8C illustrates a smart watch, which includes a housing 7302, a display portion 7304, operation buttons 7311 and 7312, a connection terminal 7313, a band 7321, a clasp 7322, and the like.

The display portion 7304 mounted in the housing 7302 serving as a bezel includes a non-rectangular display region. The display portion 7304 can display an icon 7305 indicating time, another icon 7306, and the like. The display portion 7304 may be a touch panel (an input/output device) including a touch sensor (an input device).

The smart watch illustrated in FIG. 8C can have a variety of functions, such as a function of displaying a variety of information (e.g., a still image, a moving image, and a text image) on a display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading program or data stored in a recording medium and displaying the program or data on a display portion.

The housing 7302 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like. Note that the smart watch can be manufactured using the light-emitting device for the display portion 7304.

Figure 8D:
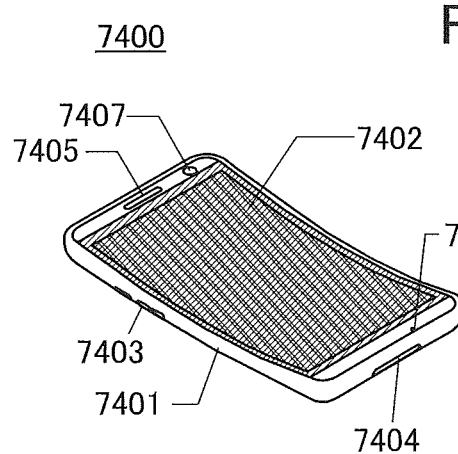
Figure 8D:
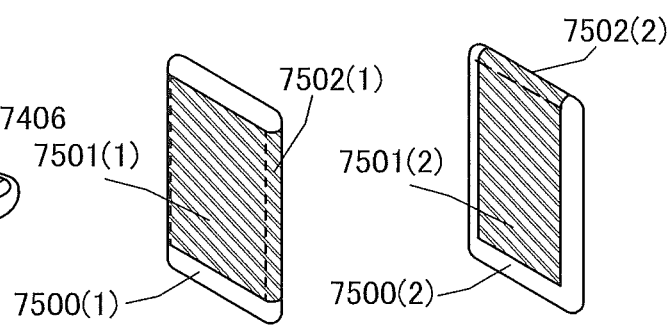

FIGS. 8D, 8D'-1, and 8D'-2 illustrate an example of a cellular phone (e.g., smartphone). A cellular phone 7400 includes a housing 7401 provided with a display portion 7402, a microphone 7406, a speaker 7405, a camera 7407, an external connection portion 7404, an operation button 7403, and the like. In the case where a light-emitting device is manufactured by forming a light-emitting element of one embodiment of the present invention over a flexible substrate, the light-emitting element can be used for the display portion 7402 having a curved surface as illustrated in FIG. 8D.

When the display portion 7402 of the cellular phone 7400 illustrated in FIG. 8D is touched with a finger or the like, data can be input to the cellular phone 7400. In addition, operations such as making a call and composing e-mail can be performed by touch on the display portion 7402 with a finger or the like.

There are mainly three screen modes of the display portion 7402. The first mode is a display mode mainly for displaying an image. The second mode is an input mode mainly for inputting data such as characters. The third mode is a display-and-input mode in which two modes of the display mode and the input mode are combined.

For example, in the case of making a call or creating e-mail, a character input mode mainly for inputting characters is selected for the display portion 7402 so that characters displayed on the screen can be input. In this case, it is preferable to display a keyboard or number buttons on almost the entire screen of the display portion 7402.

When a detection device such as a gyroscope or an acceleration sensor is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are changed by touch on the display portion 7402 or operation with the operation button 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by touch on the display portion 7402 with the palm or the finger, whereby personal authentication can be performed. In addition, by providing a backlight or a sensing light source that emits near-infrared light in the display portion, an image of a finger vein, a palm vein, or the like can be taken.

The light-emitting device can be used for a cellular phone having a structure illustrated in FIG. 8D'-1 or FIG. 8D'-2, which is another structure of the cellular phone (e.g., a smartphone).

Note that in the case of the structure illustrated in FIG. 8D'-1 or FIG. 8D'-2, text data, image data, or the like can be displayed on second screens 7502(1) and 7502(2) of housings 75000) and 7500(2) as well as first screens 7501(1) and 7501(2). Such a structure enables a user to easily see text data, image data, or the like displayed on the second screens 7502(1) and 7502(2) while the cellular phone is placed in user's breast pocket.

Figure 9A:
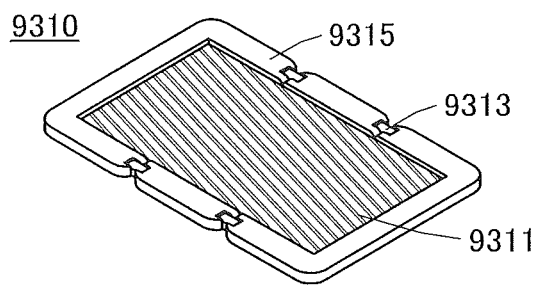
FIGS. 9A to 9C illustrate an electronic device.
Figure 9B:
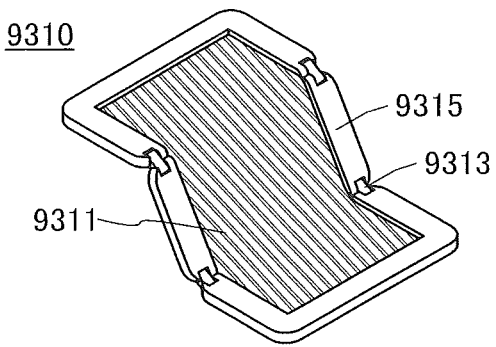
Figure 9C:
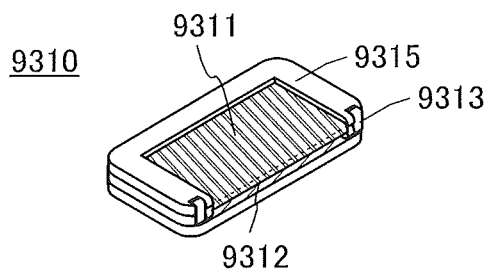

Another electronic device including a light-emitting device is a foldable portable information terminal illustrated in FIGS. 9A to 9C. FIG. 9A illustrates a portable information terminal 9310 which is opened. FIG. 9B illustrates the portable information terminal 9310 which is being opened or being folded. FIG. 9C illustrates the portable information terminal 9310 that is folded. The portable information terminal 9310 is highly portable when folded. The portable information terminal 9310 is highly browsable when opened because of a seamless large display region.

A display portion 9311 is supported by three housings 9315 joined together by hinges 9313. Note that the display portion 9311 may be a touch panel (an input/output device) including a touch sensor (an input device). By bending the display portion 9311 at a connection portion between two housings 9315 with the use of the hinges 9313, the portable information terminal 9310 can be reversibly changed in shape from an opened state to a folded state. A light-emitting device of one embodiment of the present invention can be used for the display portion 9311. A display region 9312 in the display portion 9311 is a display region that is positioned at a side surface of the portable information terminal 9310 that is folded. On the display region 9312, information icons, file shortcuts of frequently used applications or programs, and the like can be displayed, and confirmation of information and start of application can be smoothly performed.

Figure 10A:
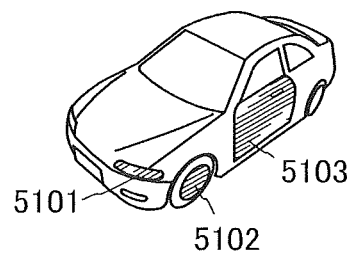
FIGS. 10A and 10B illustrate an automobile.
Figure 10B:
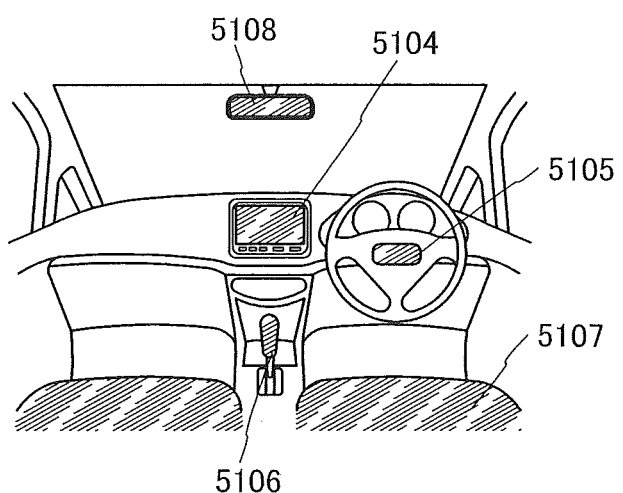

FIGS. 10A and 10B illustrate an automobile including a light-emitting device. The light-emitting device can be incorporated in the automobile, and specifically, can be included in lights 5101 (including lights of the rear part of the car), a wheel 5102 of a tire, part or whole of a door 5103, or the like on the outer side of the automobile which is illustrated in FIG. 10A. The light-emitting device can also be included in a display portion 5104, a steering wheel 5105, a gear lever 5106, a seat 5107, an inner rearview mirror 5108, or the like on the inner side of the automobile which is illustrated in FIG. 10B, or in part of a glass window.

As described above, the electronic devices and automobiles can be obtained using the light-emitting device which is one embodiment of the present invention. Note that the light-emitting device can be used for electronic devices and automobiles in a variety of fields without being limited to the electronic devices described in this embodiment.

Note that the structure described in this embodiment can be combined as appropriate with any of the structures described in the other embodiments.

Embodiment 7

In this embodiment, a structure of a lighting device fabricated using the light-emitting element which is one embodiment of the present invention will be described with reference to FIGS. 11A to 11D.

Figure 11A:
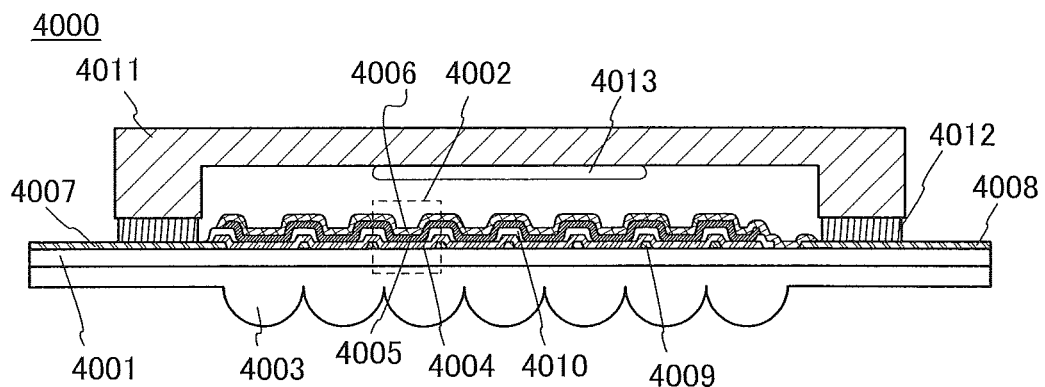
FIGS. 11A to 11D illustrate lighting devices.
Figure 11B:
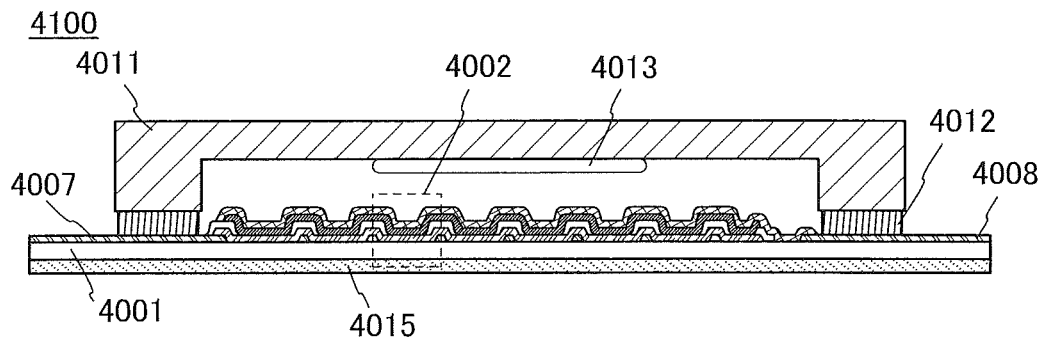
Figure 11C:
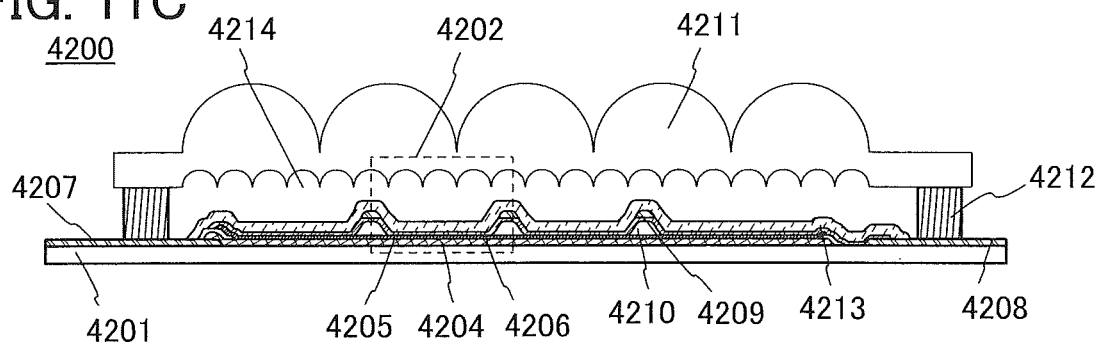
Figure 11D:
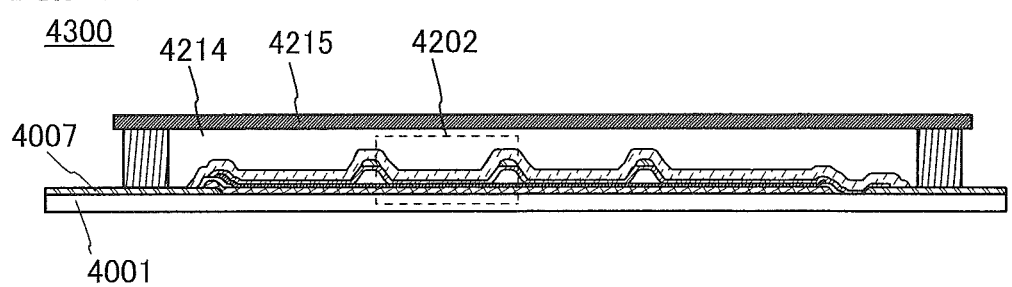

FIGS. 11A to 11D are examples of cross-sectional views of lighting devices. FIGS. 11A and 11B illustrate bottom-emission lighting devices in which light is extracted from the substrate side, and FIGS. 11C and 11D illustrate top-emission lighting devices in which light is extracted from the sealing substrate side.

A lighting device 4000 illustrated in FIG. 11A includes a light-emitting element 4002 over a substrate 4001. In addition, the lighting device 4000 includes a substrate 4003 with unevenness on the outside of the substrate 4001. The light-emitting element 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other by a sealant 4012. A desiccant 4013 is preferably provided between the sealing substrate 4011 and the light-emitting element 4002. The substrate 4003 has the unevenness illustrated in FIG. 11A, whereby the extraction efficiency of light emitted from the light-emitting element 4002 can be increased.

Instead of the substrate 4003, a diffusion plate 4015 may be provided on the outside of the substrate 4001 as in a lighting device 4100 illustrated in FIG. 11B.

A lighting device 4200 illustrated in FIG. 11C includes a light-emitting element 4202 over a substrate 4201. The light-emitting element 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may be provided. An insulating layer 4210 may be provided under the auxiliary wiring 4209.

The substrate 4201 and a sealing substrate 4211 with unevenness are bonded to each other by a sealant 4212. A barrier film 4213 and a planarization film 4214 may be provided between the sealing substrate 4211 and the light-emitting element 4202. The sealing substrate 4211 has the unevenness illustrated in FIG. 11C, whereby the extraction efficiency of light emitted from the light-emitting element 4202 can be increased.

Instead of the sealing substrate 4211, a diffusion plate 4215 may be provided over the light-emitting element 4202 as in a lighting device 4300 illustrated in FIG. 11D.

Note that the structure described in this embodiment can be combined as appropriate with any of the structures described in the other embodiments.

Embodiment 8

In this embodiment, examples of a lighting device which is an application of the light-emitting device of one embodiment of the present invention will be described with reference to FIG. 12.

Figure 12:
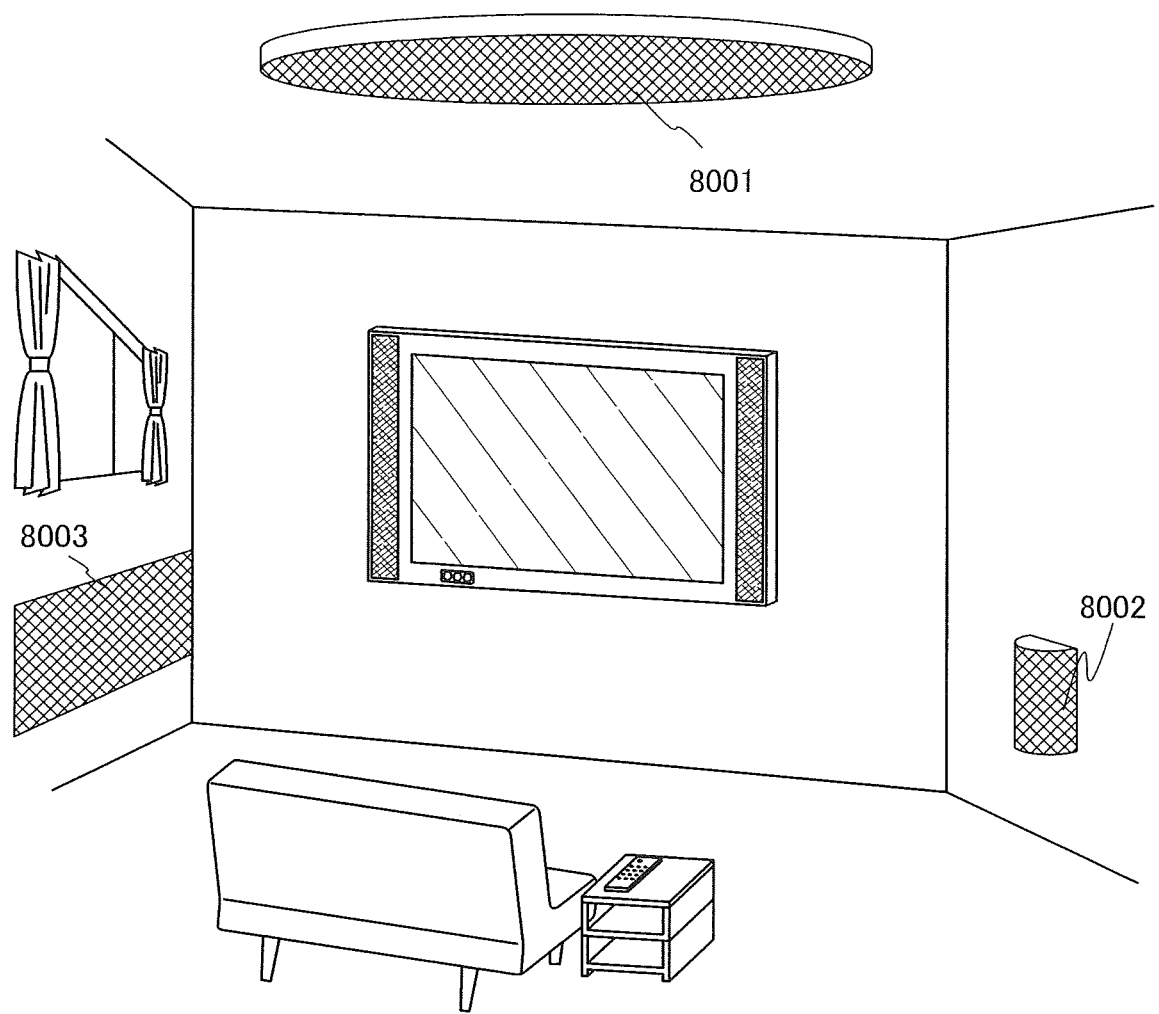
FIG. 12 illustrates lighting devices.

FIG. 12 illustrates an example in which the light-emitting device is used in an indoor lighting device 8001. Since the light-emitting device can have a large area, it can be used for a lighting device having a large area. In addition, with the use of a housing with a curved surface, a lighting device 8002 in which a light-emitting region has a curved surface can also be obtained. A light-emitting element included in the light-emitting device described in this embodiment is in a thin film form, which allows the housing to be designed more freely. Thus, the lighting device can be elaborately designed in a variety of ways. In addition, a wall of the room may be provided with a lighting device 8003.

Besides the above examples, when the light-emitting device is used as part of furniture in a room, a lighting device that functions as the furniture can be obtained.

In this manner, a variety of lighting devices to which the light-emitting device is applied can be obtained.

Note that the structure described in this embodiment can be combined as appropriate with any of the structures described in the other embodiments.

Embodiment 9

In this embodiment, touch panels including a light-emitting element of one embodiment of the present invention or a light-emitting device of one embodiment of the present invention will be described with reference to FIGS. 13A and 13B, FIGS. 14A and 14B, FIGS. 15A and 15B, FIGS. 16A and 16B, and FIG. 17.

Figure 13A:
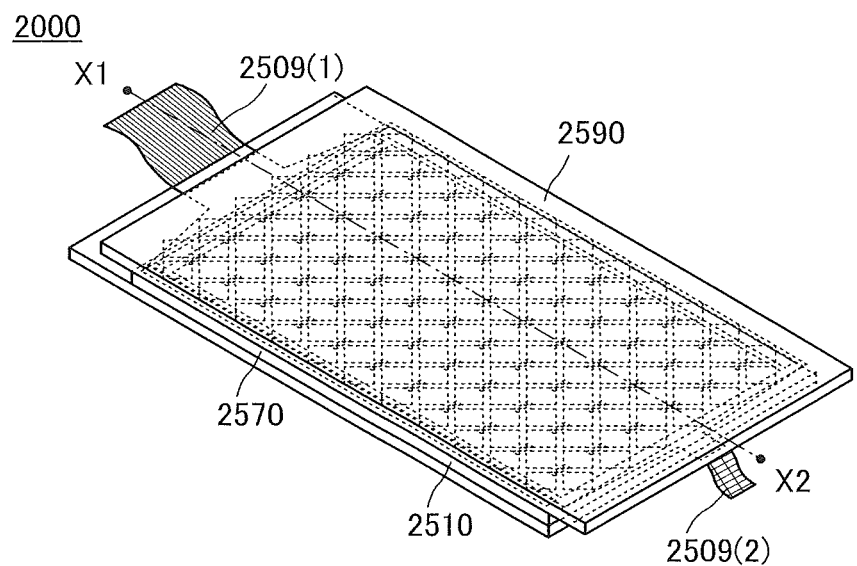
FIGS. 13A and 13B illustrate an example of a touch panel.
Figure 13B:
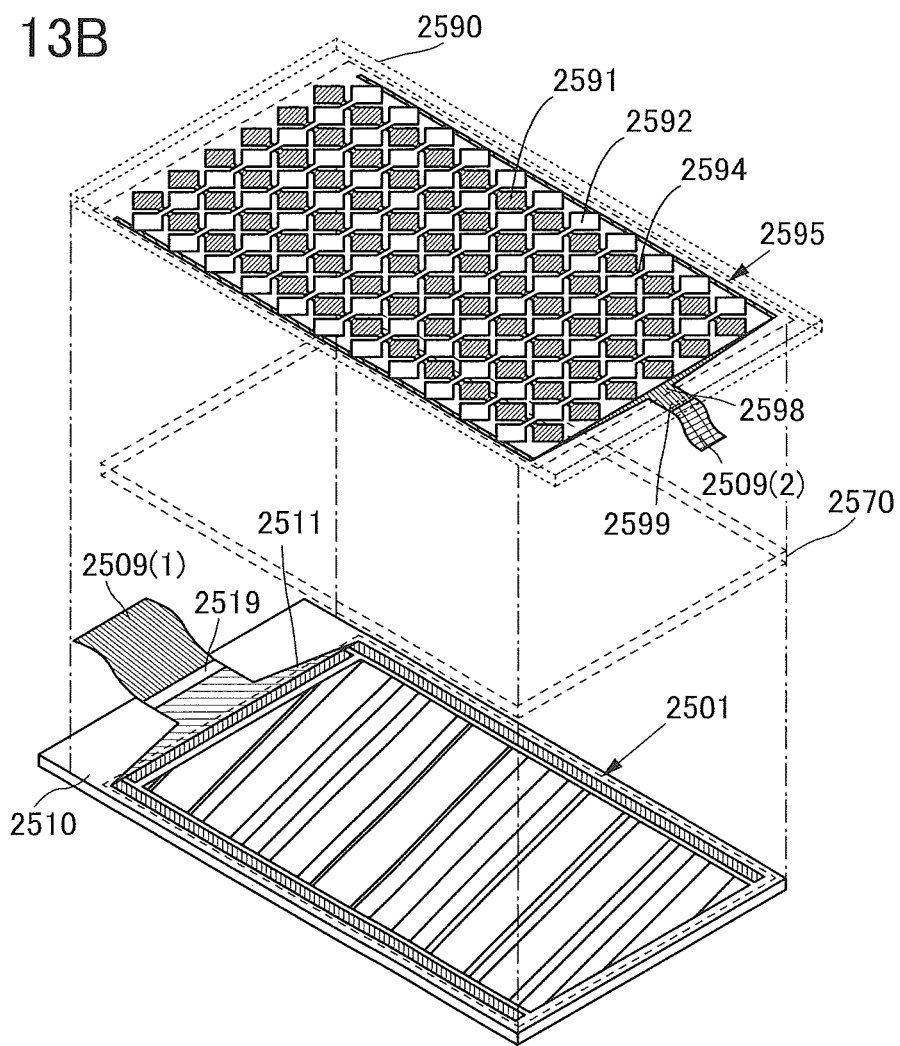

FIGS. 13A and 13B are perspective views of a touch panel 2000. Note that FIGS. 13A and 13B illustrate typical components of the touch panel 2000 for simplicity.

The touch panel 2000 includes a display panel 2501 and a touch sensor 2595 (see FIG. 13B). Furthermore, the touch panel 2000 includes substrates 2510, 2570, and 2590.

The display panel 2501 includes a plurality of pixels over the substrate 2510, and a plurality of wirings 2511 through which signals are supplied to the pixels. The plurality of wirings 2511 are led to a peripheral portion of the substrate 2510, and part of the plurality of wirings 2511 forms a terminal 2519. The terminal 2519 is electrically connected to an FPC 2509(1).

The substrate 2590 includes the touch sensor 2595 and a plurality of wirings 2598 electrically connected to the touch sensor 2595. The plurality of wirings 2598 are led to a peripheral portion of the substrate 2590, and part of the plurality of wirings 2598 forms a terminal 2599. The terminal 2599 is electrically connected to an FPC 2509(2).

Note that in FIG. 13B, electrodes, wirings, and the like of the touch sensor 2595 provided on the back side of the substrate 2590 (the side facing the substrate 2510) are indicated by solid lines for clarity.

As the touch sensor 2595, a capacitive touch sensor can be used, for example. Examples of the capacitive touch sensor are a surface capacitive touch sensor, a projected capacitive touch sensor, and the like.

Examples of the projected capacitive touch sensor are a self-capacitive touch sensor, a mutual capacitive touch sensor, and the like, which differ mainly in the driving method. The use of a mutual capacitive touch sensor is preferable because multiple points can be sensed simultaneously.

First, an example of using a projected capacitive touch sensor is described with reference to FIG. 13B. Note that in the case of a projected capacitive touch sensor, a variety of sensors that can sense the closeness or the contact of a sensing target such as a finger can be used.

The projected capacitive touch sensor 2595 includes electrodes 2591 and 2592. The electrodes 2591 are electrically connected to any of the plurality of wirings 2598, and the electrodes 2592 are electrically connected to any of the other wirings 2598. The electrodes 2592 each have a shape of a plurality of quadrangles arranged in one direction with one corner of a quadrangle connected to one corner of another quadrangle with a wiring 2594 in one direction, as illustrated in FIGS. 13A and 13B. In the same manner, the electrodes 2591 each have a shape of a plurality of quadrangles arranged with one corner of a quadrangle connected to one corner of another quadrangle; however, the direction in which the electrodes 2591 are connected is a direction crossing the direction in which the electrodes 2592 are connected. Note that the direction in which the electrodes 2591 are connected and the direction in which the electrodes 2592 are connected are not necessarily perpendicular to each other, and the electrodes 2591 may be arranged to intersect with the electrodes 2592 at an angle greater than 0° and less than 90°.

The intersecting area of the wiring 2594 and one of the electrodes 2592 is preferably as small as possible. Such a structure allows a reduction in the area of a region where the electrodes are not provided, reducing unevenness in transmittance. As a result, unevenness in the luminance of light from the touch sensor 2595 can be reduced.

Note that the shapes of the electrodes 2591 and the 2592 are not limited to the above-described shapes and can be any of a variety of shapes. For example, the plurality of electrodes 2591 may be provided so that a space between the electrodes 2591 are reduced as much as possible, and the plurality of electrodes 2592 may be provided with an insulating layer sandwiched between the electrodes 2591 and 2592. In that case, it is preferable to provide, between two adjacent electrodes 2592, a dummy electrode which is electrically insulated from these electrodes because the area of a region having a different transmittance can be reduced.

Figure 14A:
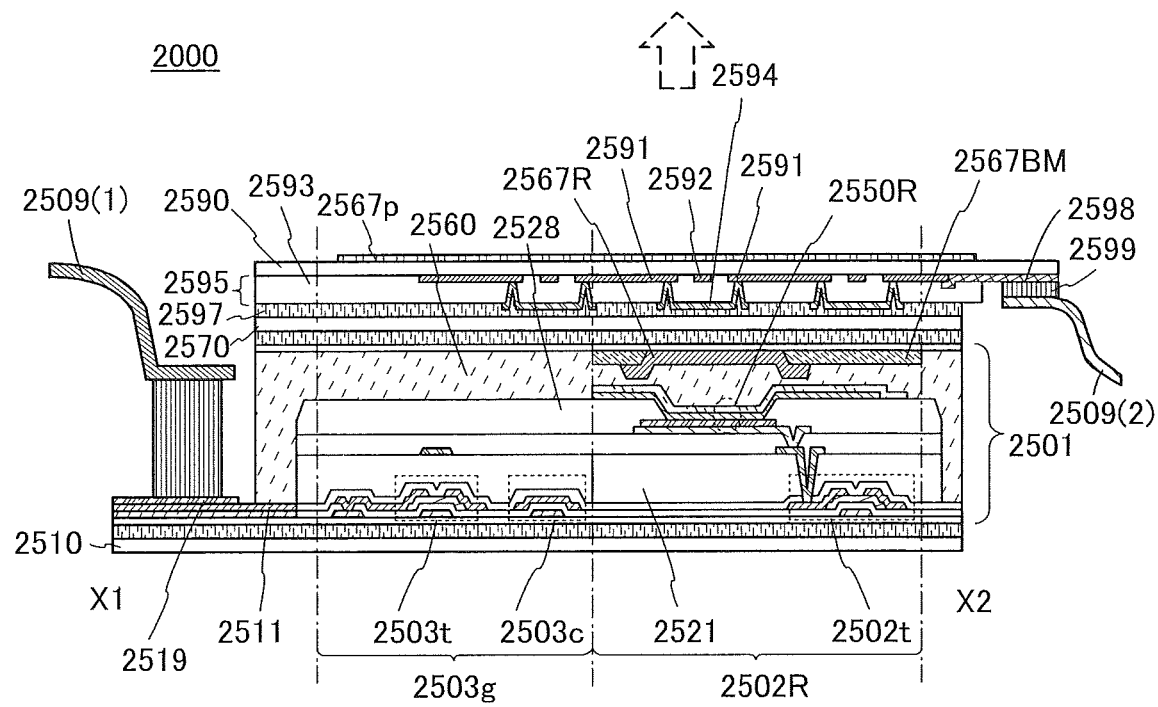
FIGS. 14A and 14B illustrate an example of a touch panel.
Figure 14B:
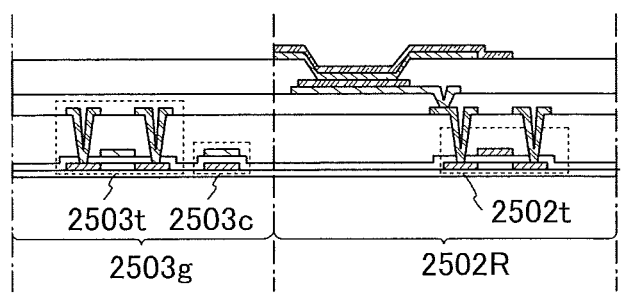

Next, the touch panel 2000 is described in detail with reference to FIGS. 14A and 14B. FIGS. 14A and 14B are cross-sectional views taken along the dashed-dotted line X1-X2 in FIG. 13A.

The touch panel 2000 includes the touch sensor 2595 and the display panel 2501.

The touch sensor 2595 includes the electrodes 2591 and 2592 that are provided in a staggered arrangement and in contact with the substrate 2590, an insulating layer 2593 covering the electrodes 2591 and 2592, and the wiring 2594 that electrically connects the adjacent electrodes 2591 to each other. Between the adjacent electrodes 2591, the electrode 2592 is provided.

The electrodes 2591 and 2592 can be formed using a light-transmitting conductive material. As a light-transmitting conductive material, a conductive oxide such as indium oxide, indium tin oxide, indium zinc oxide, zinc oxide, or zinc oxide to which gallium is added can be used. A graphene compound may be used as well. When a graphene compound is used, it can be formed, for example, by reducing a graphene oxide film. As a reducing method, a method with application of heat, a method with laser irradiation, or the like can be employed.

For example, the electrodes 2591 and 2592 can be formed by depositing a light-transmitting conductive material on the substrate 2590 by a sputtering method and then removing an unneeded portion by any of various patterning techniques such as photolithography.

Examples of a material for the insulating layer 2593 are a resin such as acrylic or epoxy resin, a resin having a siloxane bond, and an inorganic insulating material such as silicon oxide, silicon oxynitride, or aluminum oxide.

The adjacent electrodes 2591 are electrically connected to each other with the wiring 2594 formed in part of the insulating layer 2593. Note that a material for the wiring 2594 preferably has higher conductivity than materials for the electrodes 2591 and 2592 to reduce electrical resistance.

One wiring 2598 is electrically connected to any of the electrodes 2591 and 2592. Part of the wiring 2598 serves as a terminal. For the wiring 2598, a metal material such as aluminum, gold, platinum, silver, nickel, titanium, tungsten, chromium, molybdenum, iron, cobalt, copper, or palladium or an alloy material containing any of these metal materials can be used.

Through the terminal 2599, the wiring 2598 and the FPC 2509(2) are electrically connected to each other. The terminal 2599 can be formed using any of various kinds of anisotropic conductive films (ACF), anisotropic conductive pastes (ACP), and the like.

An adhesive layer 2597 is provided in contact with the wiring 2594. That is, the touch sensor 2595 is attached to the display panel 2501 so that they overlap with each other with the adhesive layer 2597 provided therebetween. Note that the substrate 2570 as illustrated in FIG. 14A may be provided over the surface of the display panel 2501 that is in contact with the adhesive layer 2597; however, the substrate 2570 is not always needed.

The adhesive layer 2597 has a light-transmitting property. For example, a thermosetting resin or an ultraviolet curable resin can be used; specifically, a resin such as an acrylic-based resin, a urethane-based resin, an epoxy-based resin, or a siloxane-based resin can be used.

The display panel 2501 in FIG. 14A includes, between the substrate 2510 and the substrate 2570, a plurality of pixels arranged in a matrix and a driver circuit. Each pixel includes a light-emitting element and a pixel circuit driving the light-emitting element.

In FIG. 14A, a pixel 2502R is shown as an example of the pixel of the display panel 2501, and a scan line driver circuit 2503g is shown as an example of the driver circuit.

The pixel 2502R includes a light-emitting element 2550R and a transistor 2502t that can supply electric power to the light-emitting element 2550R.

The transistor 2502t is covered with an insulating layer 2521. The insulating layer 2521 covers unevenness caused by the transistor and the like that have been already formed to provide a flat surface. The insulating layer 2521 may serve also as a layer for preventing diffusion of impurities. That is preferable because a reduction in the reliability of the transistor or the like due to diffusion of impurities can be prevented.

The light-emitting element 2550R is electrically connected to the transistor 2502t through a wiring. It is one electrode of the light-emitting element 2550R that is directly connected to the wiring. An end portion of the one electrode of the light-emitting element 2550R is covered with an insulator 2528.

The light-emitting element 2550R includes an EL layer between a pair of electrodes. A coloring layer 2567R is provided to overlap with the light-emitting element 2550R, and part of light emitted from the light-emitting element 2550R is transmitted through the coloring layer 2567R and extracted in the direction indicated by an arrow in the drawing. A light-blocking layer 2567BM is provided at an end portion of the coloring layer, and a sealing layer 2560 is provided between the light-emitting element 2550R and the coloring layer 2567R.

Note that when the sealing layer 2560 is provided on the side from which light from the light-emitting element 2550R is extracted, the sealing layer 2560 preferably has a light-transmitting property. The sealing layer 2560 preferably has a higher refractive index than the air.

The scan line driver circuit 2503g includes a transistor 2503t and a capacitor 2503c. Note that the driver circuit and the pixel circuits can be formed in the same process over the same substrate. Thus, in a manner similar to that of the transistor 2502t in the pixel circuit, the transistor 2503t in the driver circuit (scan line driver circuit 2503g) is also covered with the insulating layer 2521.

The wirings 2511 through which a signal can be supplied to the transistor 2503t are provided. The terminal 2519 is provided in contact with the wiring 2511. The terminal 2519 is electrically connected to the FPC 2509(1), and the FPC 2509(1) has a function of supplying signals such as an image signal and a synchronization signal. Note that a printed wiring board (PWB) may be attached to the FPC 2509(1).

Although the case where the display panel 2501 illustrated in FIG. 14A includes a bottom-gate transistor is described, the structure of the transistor is not limited thereto, and any of transistors with various structures can be used. In each of the transistors 2502t and 2503t illustrated in FIG. 14A, a semiconductor layer containing an oxide semiconductor can be used for a channel region. Alternatively, a semiconductor layer containing amorphous silicon or a semiconductor layer containing polycrystalline silicon that is obtained by crystallization process such as laser annealing can be used for a channel region.

FIG. 14B illustrates the structure of the display panel 2501 that includes a top-gate transistor instead of the bottom-gate transistor illustrated in FIG. 14A. The kind of the semiconductor layer that can be used for the channel region does not depend on the structure of the transistor.

In the touch panel 2000 illustrated in FIG. 14A, an anti-reflection layer 2567p overlapping with at least the pixel is preferably provided on a surface of the touch panel on the side from which light from the pixel is extracted, as illustrated in FIG. 14A. As the anti-reflection layer 2567p, a circular polarizing plate or the like can be used.

For the substrates 2510, 2570, and 2590 in FIG. 14A, for example, a flexible material having a vapor permeability of $1 \times 10^{-5}$ g/(m$^2$·day) or lower, preferably $1 \times 10^{-6}$ g/(m$^2$·day) or lower, can be favorably used. Alternatively, it is preferable to use the materials that make these substrates have substantially the same coefficient of thermal expansion. For example, the coefficients of linear expansion of the materials are $1\times10^{-3}$/K or lower, preferably $5\times10^{-5}$/K or lower and further preferably $1\times10^{-5}$/K or lower.

Next, a touch panel 2000 having a structure different from that of the touch panel 2000 illustrated in FIGS. 14A and 14B is described with reference to FIGS. 15A and 15B. It can be used as a touch panel as well as the touch panel 2000.

Figure 15A:
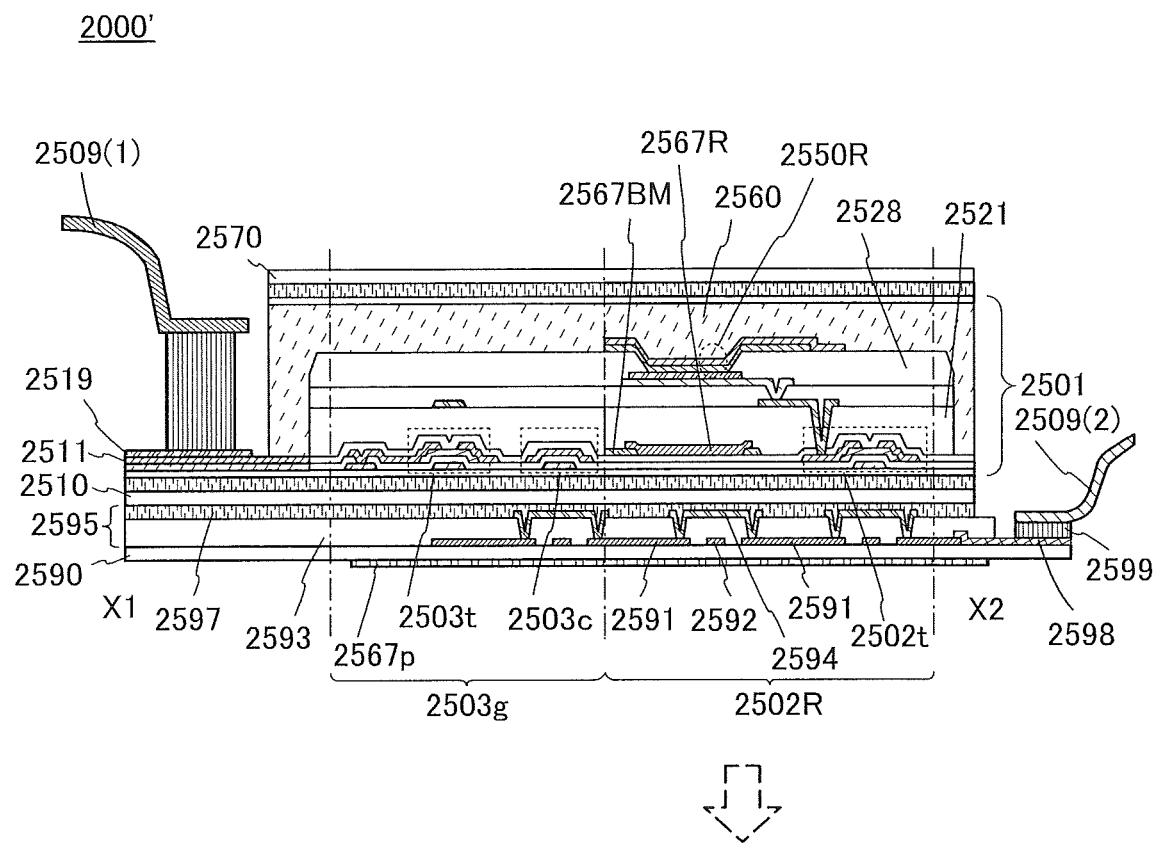
FIGS. 15A and 15B illustrate an example of a touch panel.
Figure 15B:
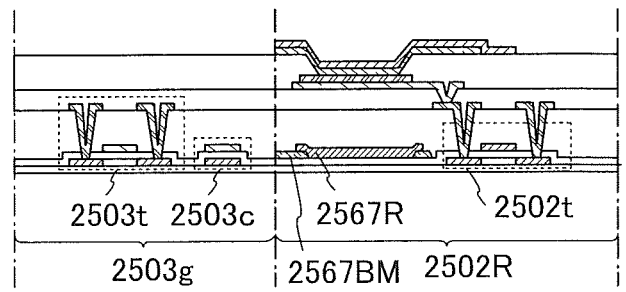

FIGS. 15A and 15B are cross-sectional views of the touch panel 2000. In the touch panel 2000' illustrated in FIGS. 15A and 15B, the position of the touch sensor 2595 relative to the display panel 2501 is different from that in the touch panel 2000 illustrated in FIGS. 14A and 14B. Only different structures are described below, and the above description of the touch panel 2000 can be referred to for the other similar structures.

The coloring layer 2567R overlaps with the light-emitting element 2550R. Light from the light-emitting element 2550R illustrated in FIG. 15A is emitted to the side where the transistor 2502t is provided. That is, (part of) light emitted from the light-emitting element 2550R passes through the coloring layer 2567R and is extracted in the direction indicated by an arrow in FIG. 15A. Note that the light-blocking layer 2567BM is provided at an end portion of the coloring layer 2567R.

The touch sensor 2595 is provided on the transistor 2502t side (the far side from the light-emitting element 2550R) of the display panel 2501 (see FIG. 15A).

The adhesive layer 2597 is in contact with the substrate 2510 of the display panel 2501 and attaches the display panel 2501 and the touch sensor 2595 to each other in the structure illustrated in FIG. 15A. The substrate 2510 is not necessarily provided between the display panel 2501 and the touch sensor 2595 that are attached to each other by the adhesive layer 2597.

As in the touch panel 2000, transistors with a variety of structures can be used for the display panel 2501 in the touch panel 2000'. Although a bottom-gate transistor is used in FIG. 15A, a top-gate transistor may be used as illustrated in FIG. 15B.

An example of a driving method of the touch panel is described with reference to FIGS. 16A and 16B.

Figure 16A:
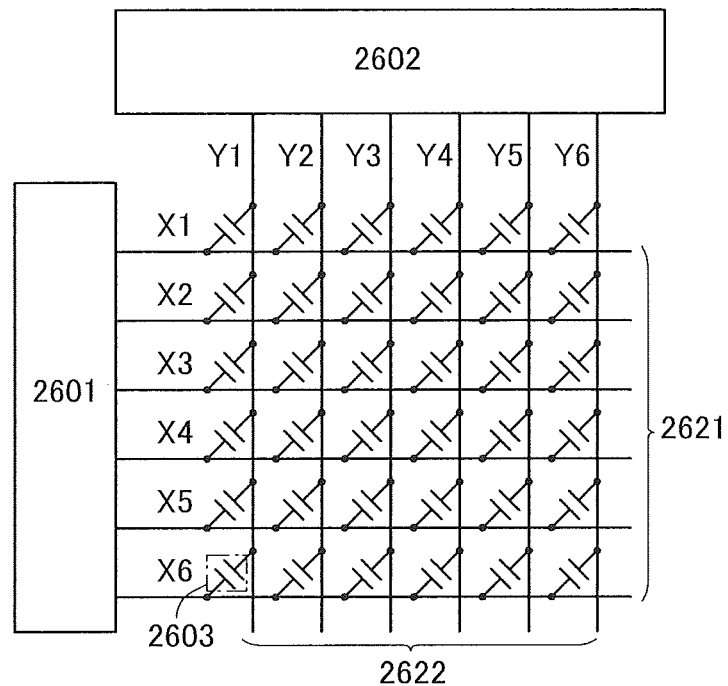
FIGS. 16A and 16B are a block diagram and a timing chart of a touch sensor.

FIG. 16A is a block diagram illustrating the structure of a mutual capacitive touch sensor. FIG. 16A illustrates a pulse voltage output circuit 2601 and a current sensing circuit 2602. Note that in the example of FIG. 16A, six wirings X1-X6 represent electrodes 2621 to which a pulse voltage is supplied, and six wirings Y1-Y6 represent electrodes 2622 that sense a change in current. FIG. 16A also illustrates a capacitor 2603 which is formed in a region where the electrodes 2621 and 2622 overlap with each other. Note that functional replacement between the electrodes 2621 and 2622 is possible.

The pulse voltage output circuit 2601 is a circuit for sequentially applying a pulse voltage to the wirings X1 to X6. By application of a pulse voltage to the wirings X1 to X6, an electric field is generated between the electrodes 2621 and 2622 of the capacitor 2603. When the electric field between the electrodes is shielded, for example, a change occurs in the capacitor 2603 (mutual capacitance). The approach or contact of a sensing target can be sensed by utilizing this change.

The current sensing circuit 2602 is a circuit for sensing changes in current flowing through the wirings Y1 to Y6 that are caused by the change in mutual capacitance in the capacitor 2603. No change in current value is sensed in the wirings Y1 to Y6 when there is no approach or contact of a sensing target, whereas a decrease in current value is sensed when mutual capacitance is decreased owing to the approach or contact of a sensing target. Note that an integrator circuit or the like is used for sensing of current.

Figure 16B:
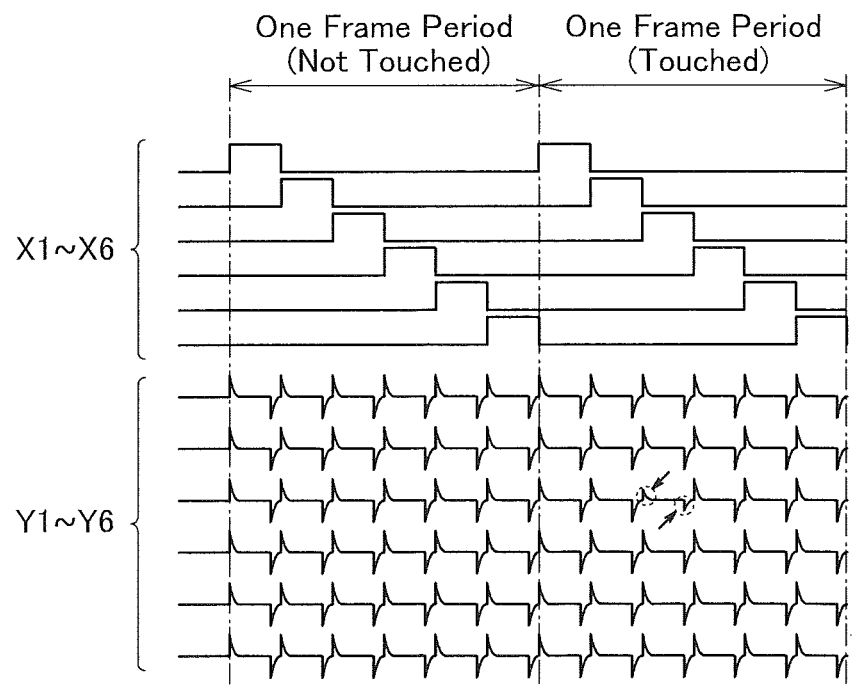

FIG. 16B is a timing chart showing input and output waveforms in the mutual capacitive touch sensor illustrated in FIG. 16A. In FIG. 16B, sensing of a sensing target is performed in all the rows and columns in one frame period. FIG. 16B shows a period when a sensing target is not sensed (not touched) and a period when a sensing target is sensed (touched). Sensed current values of the wirings Y1 to Y6 are shown as the waveforms of voltage values.

A pulse voltage is sequentially applied to the wirings X1 to X6, and the waveforms of the wirings Y1 to Y6 change in accordance with the pulse voltage. When there is no approach or contact of a sensing target, the waveforms of the wirings Y1 to Y6 change uniformly in accordance with changes in the voltages of the wirings X1 to X6. The current value is decreased at the point of approach or contact of a sensing target and accordingly the waveform of the voltage value changes. By sensing a change in mutual capacitance in this manner, the approach or contact of a sensing target can be sensed.

Figure 17:
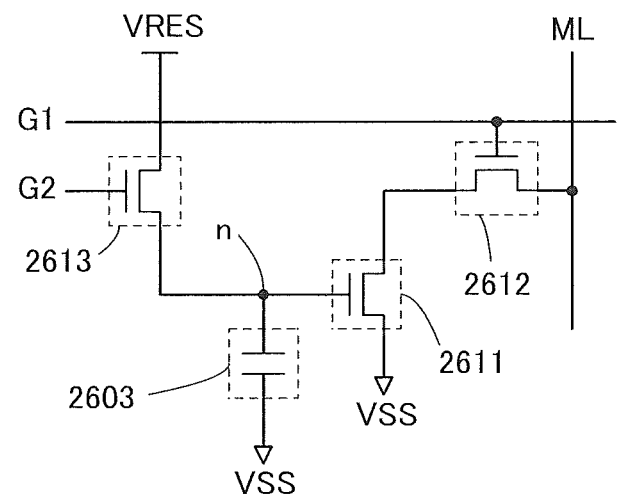
FIG. 17 is a circuit diagram of a touch sensor.

Although FIG. 16A illustrates a passive touch sensor in which only the capacitor 2603 is provided at the intersection of wirings as a touch sensor, an active touch sensor including a transistor and a capacitor may be used. FIG. 17 is a sensor circuit included in an active touch sensor.

The sensor circuit illustrated in FIG. 17 includes the capacitor 2603 and transistors 2611, 2612, and 2613.

A signal G2 is input to a gate of the transistor 2613. A voltage VRES is applied to one of a source and a drain of the transistor 2613, and one electrode of the capacitor 2603 and a gate of the transistor 2611 are electrically connected to the other of the source and the drain of the transistor 2613. One of a source and a drain of the transistor 2611 is electrically connected to one of a source and a drain of the transistor 2612, and a voltage VSS is applied to the other of the source and the drain of the transistor 2611. A signal G1 is input to a gate of the transistor 2612, and a wiring ML is electrically connected to the other of the source and the drain of the transistor 2612. The voltage VSS is applied to the other electrode of the capacitor 2603.

Next, the operation of the sensor circuit illustrated in FIG. 17 is described. First, a potential for turning on the transistor 2613 is supplied as the signal G2, and a potential with respect to the voltage VRES is thus applied to a node n connected to the gate of the transistor 2611. Then, a potential for turning off the transistor 2613 is applied as the signal G2, whereby the potential of the node n is maintained. Then, mutual capacitance of the capacitor 2603 changes owing to the approach or contact of a sensing target such as a finger; accordingly, the potential of the node n is changed from VRES.

In reading operation, a potential for turning on the transistor 2612 is supplied as the signal G1. A current flowing through the transistor 2611, that is, a current flowing through the wiring ML is changed in accordance with the potential of the node n. By sensing this current, the approach or contact of a sensing target can be sensed.

In each of the transistors 2611, 2612, and 2613, an oxide semiconductor layer is preferably used as a semiconductor layer in which a channel region is formed. In particular, such a transistor is preferably used as the transistor 2613, so that the potential of the node n can be held for a long time and the frequency of operation of resupplying VRES to the node n (refresh operation) can be reduced.

At least part of this embodiment can be implemented in combination with any of the embodiments described in this specification as appropriate.

Embodiment 10

In this embodiment, as a display device including a light-emitting element, a display device which includes a reflective liquid crystal element and a light-emitting element and is capable of performing display both in a transmissive mode and a reflective mode is described with reference to FIGS. 36A, 36B1, and 36B2, FIG. 37, and FIG. 38.

The display device described in this embodiment can be driven with extremely low power consumption for display using the reflective mode in a bright place such as outdoors. Meanwhile, in a dark place such as indoors at night, image can be displayed at an optimal luminance with the use of the transmissive mode. Thus, by combination of these modes, the display device can display an image with lower power consumption and a higher contrast compared to a conventional display panel.

As an example of the display device of this embodiment, description is made on a display device in which a liquid crystal element provided with a reflective electrode and a light-emitting element are stacked and an opening of the reflective electrode is provided in a position overlapping with the light-emitting element. Visible light is reflected by the reflective electrode in the reflective mode and light emitted from the light-emitting element is emitted through the opening of the reflective electrode in the transmissive mode. Note that transistors used for driving these elements (the liquid crystal element and the light-emitting element) are preferably formed on the same plane. It is preferable that the liquid crystal element and the light-emitting element be stacked through an insulating layer.

FIG. 36A is a block diagram illustrating a display device described in this embodiment. A display device 600 includes a circuit (G) 601, a circuit (S) 602, and a display portion 603. In the display portion 603, a plurality of pixels 604 are arranged in an R direction and a C direction in a matrix. A plurality of wirings G1, wirings G2, wirings ANO, and wirings CSCOM are electrically connected to the circuit (G) 601. These wirings are also electrically connected to the plurality of pixels 604 arranged in the R direction. A plurality of wirings S1 and wirings S2 are electrically connected to the circuit (S) 602, and these wirings are also electrically connected to the plurality of pixels 604 arranged in the C direction.

Each of the plurality of pixels 604 includes a liquid crystal element and a light-emitting element. The liquid crystal element and the light-emitting element include portions overlapping with each other.

FIG. 36B1 shows the shape of a conductive film 605 serving as a reflective electrode of the liquid crystal element included in the pixel 604. Note that an opening 607 is provided in a position 606 which is part of the conductive film 605 and which overlaps with the light-emitting element. That is, light emitted from the light-emitting element is emitted through the opening 607.

The pixels 604 in FIG. 36B1 are arranged such that adjacent pixels 604 in the R direction exhibit different colors. Furthermore, the openings 607 are provided so as not to be arranged in a line in the R direction. Such arrangement has an effect of suppressing crosstalk between the light emitting elements of adjacent pixels 604.

The opening 607 can have a polygonal shape, a quadrangular shape, an elliptical shape, a circular shape, a cross shape, a stripe shape, or a slit-like shape, for example.

FIG. 36B2 illustrates another example of the arrangement of the conductive films 605.

The ratio of the opening 607 to the total area of the conductive film 605 (excluding the opening 607) affects the display of the display device. That is, a problem is caused in that as the area of the opening 607 is larger, the display using the liquid crystal element becomes darker; in contrast, as the area of the opening 607 is smaller, the display using the light-emitting element becomes darker. Furthermore, in addition to the problem of the ratio of the opening, a small area of the opening 607 itself also causes a problem in that extraction efficiency of light emitted from the light-emitting element is decreased. The ratio of opening 607 to the total area of the conductive film 605 (other than the opening 607) is preferably 5% or more and 60% or less for maintaining display quality at the time of combination of the liquid crystal element and the light-emitting element.

Figure 37:
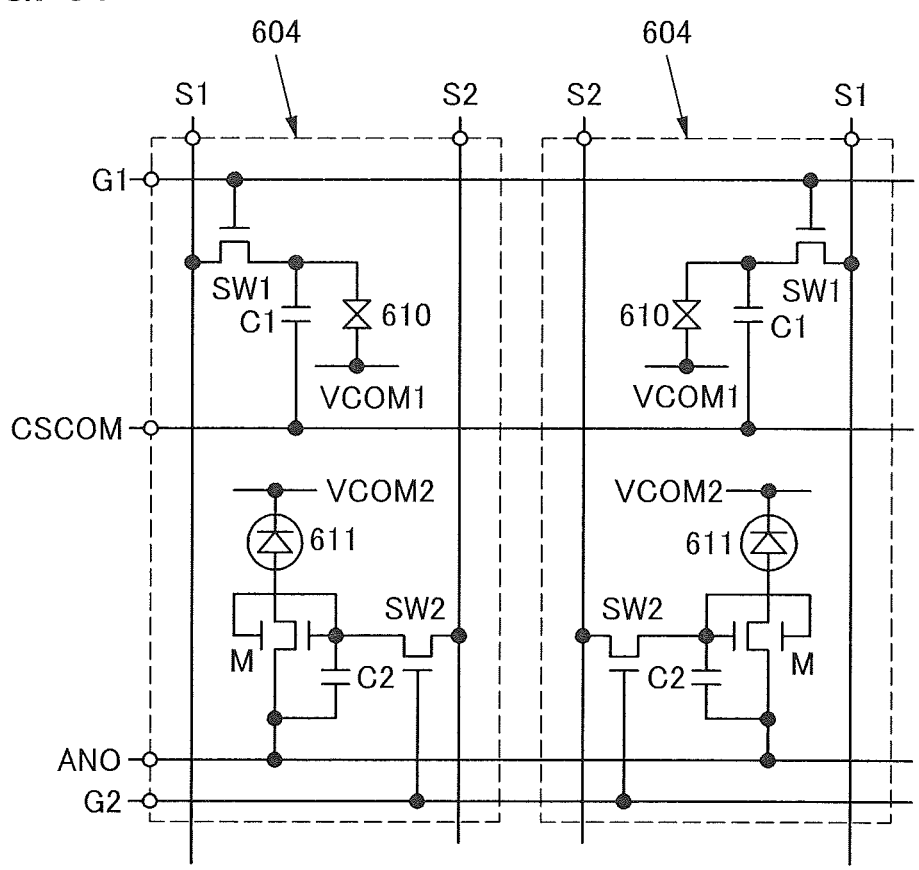
FIG. 37 shows a circuit structure of a display device.

Next, an example of a circuit configuration of the pixel 604 is described with reference to FIG. 37. FIG. 37 shows two adjacent pixels 604.

The pixel 604 includes a transistor SW1, a capacitor C1, a liquid crystal element 610, a transistor SW2, a transistor M, a capacitor C2, a light-emitting element 611, and the like. Note that these components are electrically connected to any of the wiring G1, the wiring G2, the wiring ANO, the wiring CSCOM, the wiring S1, and the wiring S2 in the pixel 604. The liquid crystal element 610 and the light-emitting element 611 are electrically connected to a wiring VCOM1 and a wiring VCOM2, respectively.

A gate of the transistor SW1 is connected to the wiring G1. One of a source and a drain of the transistor SW1 is connected to the wiring S1, and the other of the source and the drain is connected to one electrode of the capacitor C1 and one electrode of the liquid crystal element 610. The other electrode of the capacitor C1 is electrically connected to the wiring CSCOM. The other electrode of the liquid crystal element 610 is connected to the wiring VCOM1.

A gate of the transistor SW2 is connected to the wiring G2. One of a source and a drain of the transistor SW2 is connected to the wiring S2, and the other of the source and the drain is connected to one electrode of the capacitor C2 and a gate of the transistor M. The other electrode of the capacitor C2 is connected to one of a source and a drain of the transistor M and the wiring ANO. The other of the source and the drain of the transistor M is connected to one electrode of the light-emitting element 611. Furthermore, the other electrode of the light-emitting element 611 is connected to the wiring VCOM2.

Note that the transistor M includes two gates between which a semiconductor is provided and which are electrically connected to each other. With such a structure, the amount of current flowing through the transistor M can be increased.

The on/off state of the transistor SW1 is controlled by a signal from the wiring G1. A predetermined potential is supplied from the wiring VCOM1. Furthermore, orientation of liquid crystals of the liquid crystal element 610 can be controlled by a signal from the wiring S1. A predetermined potential is supplied from the wiring CSCOM.

The on/off state of the transistor SW2 is controlled by a signal from the wiring G2. By the difference between the potentials applied from the wiring VCOM2 and the wiring ANO, the light-emitting element 611 can emit light. Furthermore, the on/off state of the transistor M is controlled by a signal from the wiring S2.

Accordingly, in the structure of this embodiment, in the case of the reflective mode, the liquid crystal element 610 is controlled by the signals supplied from the wiring G1 and the wiring S1 and optical modulation is utilized, whereby display can be performed. In the case of the transmissive mode, the light-emitting element 611 can emit light when the signals are supplied from the wiring G2 and the wiring S2. In the case where both modes are performed at the same time, desired driving can be performed based on the signals from the wiring G1, the wiring G2, the wiring S1, and the wiring S2.

Figure 38:
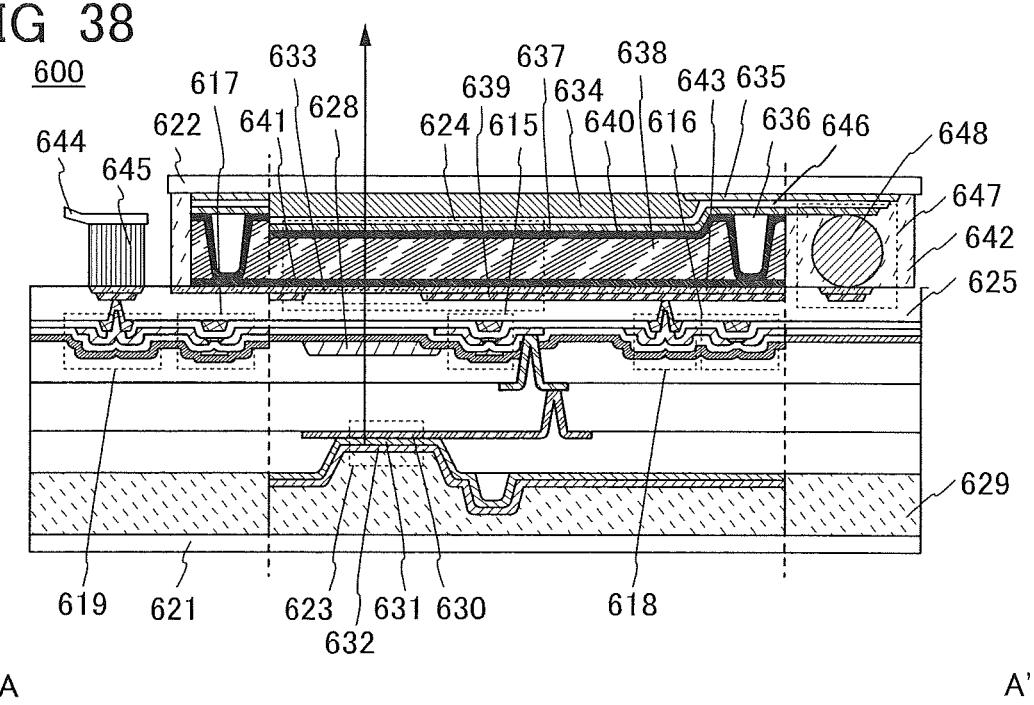
FIG. 38 is a cross-sectional structure of a display device.

Next, specific description will be given with reference to FIG. 38, a schematic cross-sectional view of the display device 600 described in this embodiment.

The display device 600 includes a light-emitting element 623 and a liquid crystal element 624 between substrates 621 and 622. Note that the light-emitting element 623 and the liquid crystal element 624 are formed with an insulating layer 625 positioned therebetween. That is, the light-emitting element 623 is positioned between the substrate 621 and the insulating layer 625, and the liquid crystal element 624 is positioned between the substrate 622 and the insulating layer 625.

A transistor 615, a transistor 616, a transistor 617, a coloring layer 628, and the like are provided between the insulating layer 625 and the light-emitting element 623.

A bonding layer 629 is provided between the substrate 621 and the light-emitting element 623. The light-emitting element 623 includes a conductive layer 630 serving as one electrode, an EL layer 631, and a conductive layer 632 serving as the other electrode which are stacked in this order over the insulating layer 625. In the light-emitting element 623 that is a bottom emission light-emitting element, the conductive layer 632 and the conductive layer 630 contain a material that reflects visible light and a material that transmits visible light, respectively. Light emitted from the light-emitting element 623 is transmitted through the coloring layer 628 and the insulating layer 625 and then transmitted through the liquid crystal element 624 via an opening 633, thereby being emitted to the outside of the substrate 622.

In addition to the liquid crystal element 624, a coloring layer 634, a light-blocking layer 635, an insulating layer 646, a structure 636, and the like are provided between the insulating layer 625 and the substrate 622. The liquid crystal element 624 includes a conductive layer 637 serving as one electrode, a liquid crystal 638, a conductive layer 639 serving as the other electrode, alignment films 640 and 641, and the like. Note that the liquid crystal element 624 is a reflective liquid crystal element and the conductive layer 639 serves as a reflective electrode; thus, the liquid crystal element 624 and the conductive layer 639 are formed using a material with high reflectivity. Furthermore, the conductive layer 637 serves as a transparent electrode, and thus is formed using a material that transmits visible light. Alignment films 640 and 641 may be provided on the conductive layers 637 and 638 and in contact with the liquid crystal layer 638. The insulating layer 646 is provided so as to cover the coloring layer 634 and the light-blocking 635 and serves as an overcoat layer. Note that the alignment films 640 and 641 are not necessarily provided.

The opening 633 is provided in part of the conductive layer 639. A conductive layer 643 is provided in contact with the conductive layer 639 and has a light-transmitting property because of being formed using a material transmitting visible light.

The structure 636 serves as a spacer that prevents the substrate 622 from coming closer to the insulating layer 625 than required. The structure 636 is not necessarily provided.

One of a source and a drain of the transistor 615 is electrically connected to the conductive layer 630 in the light-emitting element 623. For example, the transistor 615 corresponds to the transistor M in FIG. 37.

One of a source and a drain of the transistor 616 is electrically connected to the conductive layer 639 and the conductive layer 643 in the liquid crystal element 624 through a terminal portion 618. That is, the terminal portion 618 electrically connects the conductive layers provided on both surfaces of the insulating layer 625. The transistor 616 corresponds to the switch SW1 in FIG. 37.

A terminal portion 619 is provided in a region where the substrates 621 and 622 do not overlap with each other. Similarly to the terminal portion 618, the terminal portion 619 electrically connects the conductive layers provided on both surfaces of the insulating layer 625. The terminal portion 619 is electrically connected to a conductive layer obtained by processing the same conductive film as the conductive layer 643. Thus, the terminal portion 619 and the FPC 644 can be electrically connected to each other through a connection layer 645.

A connection portion 647 is provided in part of a region where a bonding layer 642 is provided. In the connection portion 647, the conductive layer obtained by processing the same conductive film as the conductive layer 643 and part of the conductive layer 637 are electrically connected with a connector 648. Accordingly, a signal or a potential input from the FPC 644 can be supplied to the conductive layer 637 through the connection portion 647.

The structure 636 is provided between the conductive layer 637 and the conductive layer 643. The structure 636 maintains a cell gap of the liquid crystal element 624.

As the conductive layer 643, a metal oxide, a metal nitride, or an oxide such as an oxide semiconductor whose resistance is reduced is preferably used. In the case of using an oxide semiconductor, a material in which at least one of the concentrations of hydrogen, boron, phosphorus, nitrogen, and other impurities and the number of oxygen vacancies is made to be higher than those in a semiconductor layer of a transistor is used for the conductive layer 643.

Note that the structure described in this embodiment can be combined as appropriate with any of the structures described in the other embodiments.

Embodiment 11

In this embodiment, a light-emitting element is described. The light-emitting element described in this embodiment has a structure different from that described in Embodiment 2. An element structure and a manufacturing method of the light-emitting element is described with reference to FIGS. 39A and 39B. For the portions similar to those in Embodiments 2, the description of Embodiments 2 can be referred to and description is omitted.

The light-emitting element described in this embodiment has a structure in which an EL layer 3202 including a light-emitting layer 3213 is sandwiched between a pair of electrodes (a cathode 3201 and an anode 3203) formed over a substrate 3200. The EL layer 3202 can be formed by stacking a light-emitting layer, a hole-injection layer, a hole-transport layer, an electron-injection layer, an electron-transport layer, and the like as in the EL layer described in Embodiment 2.

Figure 39A:
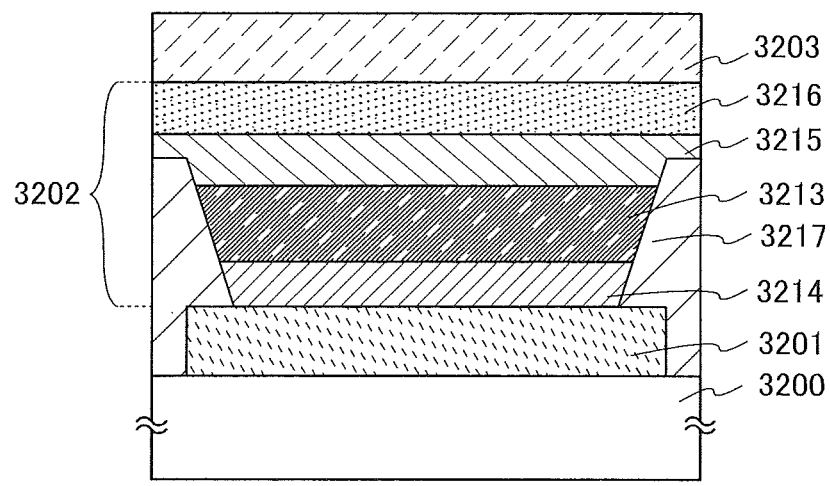
FIGS. 39A and 39B illustrate a light-emitting element.

In this embodiment, as shown in FIG. 39A, description is made on the light-emitting element having a structure in which the EL layer 3202 including an electron-injection layer 3214, the light-emitting layer 3213, a hole-transport layer 3215, and a hole-injection layer 3216 are formed over the cathode 3201 in this order over the substrate 3200 and the anode 3203 is formed over the hole-injection layer 3216. Here, though an electron-transport layer is not provided, the electron-injection layer 3214 can serve as the electron-transport layer with a material having a high electron-transport property.

In the above-described light-emitting element, current flows due to a potential difference applied between the cathode 3201 and the anode 3203, and holes and electrons recombine in the EL layer 3202, whereby light is emitted. Then, this light emission is extracted to the outside through one or both of the cathode 3201 and the anode 3203. Therefore, one or both of the cathode 3201 and the anode 3203 are electrodes having light-transmitting properties; light can be extracted through the electrode having a light-transmitting property.

Figure 39B:
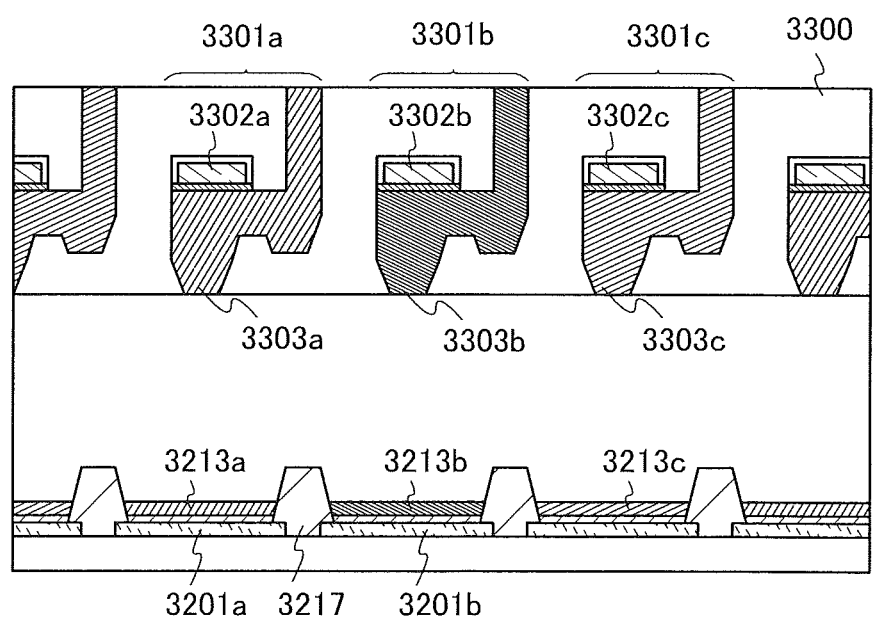

In the light-emitting element described in this embodiment, end portions of the cathode 3201 are covered with insulators 3217 as shown in FIG. 39. Note that the insulators 3217 are formed so as to fill a space between adjacent cathodes 3201 (e.g., 3201a and 3201b) as shown in FIG. 39B.

As the insulator 3217, an inorganic compound or an organic compound having an insulating property can be used. As the organic compound, a photosensitive resin such as a resist material, e.g., an acrylic resin, a polyimide resin, a fluorine-based resin, or the like can be used. As the inorganic material, silicon oxide, silicon oxynitride, silicon nitride, or the like can be used, for example. Note that the insulator 3217 preferably has a water-repellent surface. As its treatment method, plasma treatment, chemical treatment (using an alkaline solution or an organic solvent), or the like can be employed.

In this embodiment, the electron-injection layer 3214 formed over the cathode 3201 is formed using a high molecular compound. It is preferable to use a high molecular compound which does not dissolve in the nonaqueous solvent and which has a high electron-transport property. Specifically, the electron-injection layer 3214 is formed using an appropriate combination of any of the materials (including not only a high molecular compound but also an alkali metal, an alkaline earth metal, or a compound thereof) which can be used for the electron-injection layer 115 and electron-transport layer 114 in Embodiment 2. The materials are dissolved in a polar solvent, and the layer is formed by a coating method.

Here, examples of the polar solvent include methanol, ethanol, propanol, isopropanol, butyl alcohol, ethylene glycol, and glycerin.

The light-emitting layer 3213 is formed over the electron-injection layer 3214. The light-emitting layer 3213 is formed by depositing (or applying) ink in which any of the materials (a light-emitting substance) which can be used for the light-emitting layer 3213 in Embodiment 2 are combined as appropriate and dissolved (dispersed) in a polar solvent, by a wet method (an ink-jet method or a printing method). Although the electron-injection layer 3214 is used in common in light-emitting elements of different emission colors, a material corresponding to an emission color is selected for the light-emitting layer 3213. As the polar solvent, an aromatic-based solvent such as toluene or xylene, or a heteroaromatic-based solvent such as pyridine can be used. Alternatively, a solvent such as hexane, 2-methylhexane cyclohexane, or chloroform can be used.

As shown in FIG. 39B, the ink for forming the light-emitting layer 3213 is applied from a head portion 3300 of an apparatus for applying a solution (hereinafter referred to as solution application apparatus). Note that the head portion 3300 includes a plurality of spraying portions 3301a to 3301c for spraying ink, and piezoelectric elements 3302a to 3302c are provided for the spraying portions 3301a to 3301c. Furthermore, the spraying portions 3301a to 3301c are filled with respective ink 3303a to ink 3303c containing emission substances exhibiting different emission colors.

The ink 3303a to ink 3303c are sprayed from the respective spraying portions 3301a to 3301c, whereby light-emitting layers 3213a to 3213c emitting different colors are formed.

The hole-transport layer 3215 is formed over the light-emitting layer 3213. The hole-transport layer 3215 can be formed by a combination of any of the materials which can be used for the hole-transport layer 3215 in Embodiment 2. The hole-transport layer 3215 can be formed by a vacuum evaporation method or a coating method. In the case of employing a coating method, the material which is dissolved in a solvent is applied to the light-emitting layer 3213 and the insulator 3217. As a coating method, an ink-jet method, a spin coating method, a printing method, or the like can be used.

The hole-injection layer 3216 is formed over the hole-transport layer 3215. The anode 3203 is formed over the hole-injection layer 3216. They are formed using an appropriate combination of the materials described in Embodiment 2 by a vacuum evaporation method.

The light-emitting element can be formed through the above steps. Note that in the case of using an organometallic complex in the light-emitting layer, phosphorescence due to the organometallic complex is obtained. Thus, the light-emitting element can have higher efficiency than a light-emitting element formed using only fluorescent compounds.

Note that the structure described in this embodiment can be used in combination with any of the structures described in the other embodiments, as appropriate.

Embodiment 12

In this embodiment, an example of a lighting system to which a light-emitting element is applied, is described with reference to FIG. 40.

Figure 40:
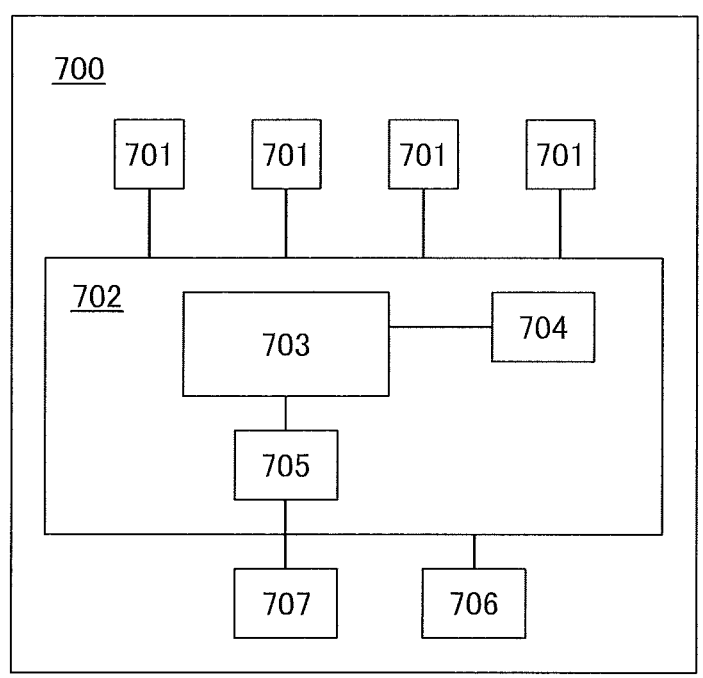
FIG. 40 illustrates a structure of a lighting system.

As shown in FIG. 40, a lighting system 700 includes a plurality of light emitting elements 701 and a control unit 702. The control unit 702 is electrically connected to a power source 706. The control unit 702 is electrically connected to each of the plurality of light-emitting elements 701 and controls lighting and extinction of each of the light-emitting elements 701 and control the luminance at the time of lighting. That is, the lighting system of this embodiment is configured to control emission of the light-emitting elements which are light sources of the lighting in accordance with external information. Here, the external information includes brightness information, lighting time information, and temperature information for example. To sense the external information, various parameters indicating such information can be used as signals.

Any of the light-emitting elements described in the other embodiments can be used for the light-emitting elements

701. An anode and a cathode of the light-emitting element are electrically connected to the control unit 702, and a potential of one of the electrodes or potentials of both of the electrodes are controlled by a control signal from the control unit 702, whereby lighting and extinction of the light-emitting elements 701 and the luminance at the time of lighting are controlled.

The control unit 702 includes a central processing unit (CPU) 703, a memory 704, and a communication unit 705. Note that the communication unit 705 is electrically connected to a sensor 707 and receives lighting time information of the light-emitting elements 701 and external brightness information which are sensed by the sensor 707.

As the sensor 707, a photodiode, a light-receiving element such as a CdS photoconductive element, a charge coupled device (CCD), a sensor including a CMOS sensor, or the like which can sense the above-described information (e.g., lighting time information of the light-emitting element 701 and external brightness information) as a data signal, can be used.

In the memory 704, a program for controlling lighting time of the light-emitting elements 701 is stored. The CPU 703 reads out from the memory 704 a signal (a lighting signal or an extinction signal) for lighting or extinguishing the plurality of light-emitting elements 701 in accordance with lighting time information of the light-emitting elements 701 input from the communication unit 705, and executes driving of the light-emitting elements 701. As an example of the program for controlling lighting time of the light-emitting elements 701, a program with which consecutive lighting is completed in a certain period in order to prevent unnecessary lighting for a long time, is given.

Note that a program for controlling the luminance of the light-emitting elements may be stored in the memory 704. In that case, the CPU 703 reads out signals (luminance control signals) for controlling the luminance of the plurality of light-emitting elements 701 in accordance with external brightness information input from the communication unit 705, and executes driving of the light-emitting elements 701. An example of the program for controlling the luminance of the light-emitting elements includes a program with which luminance can be strengthened or weakened on the basis of whether the external brightness information sensed by the sensor 707 reaches reference brightness set in advance. Furthermore, the signals for controlling the luminance of the plurality of light-emitting elements 701 may be different for each of the plurality of the light-emitting elements 701 or may be the same.

Specifically, in the case where the CPU 703 executes driving of the light-emitting element 701, the signal read out from the memory 704 is converted by the CPU 703, and the potential of one electrode of the light-emitting element is controlled.

Note that the plurality of the light-emitting elements 701 used in the lighting system of this embodiment may have the same structure or different structures. Furthermore, emission colors of the plurality of the light-emitting elements 701 may be the same or different from each other. The structure of the light-emitting element described in any of the other embodiments can be applied to the structure of the light-emitting element in this embodiment.

Note that the structure described in this embodiment can be used in combination with any of the structures described in the other embodiments, as appropriate.

Example 1

Figure 18:
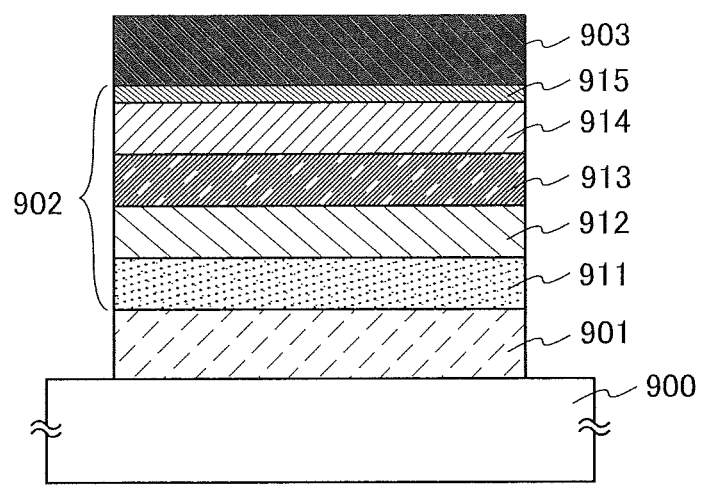
FIG. 18 illustrates a light-emitting element.

In this example, light-emitting elements were fabricated and characteristic thereof were shown. Specifically, Light-emitting element 1 in which only 1,5-bis[4-(9H-carbazole-9-yl)phenyl]anthracene (abbreviation: 1,5CzP2A) (Structural Formula: 100) was used in a light-emitting layer, Light-emitting element 2 in which 1,5CzP2A and 1,6mMemFLPAPrn that was a dopant (a light-emitting substance) were used in a light-emitting layer, Light-emitting element 3 in which only 1,8-bis[4-(9H-carbazol-9-yl)phenyl]anthracene (abbreviation: 1,8CzP2A) (Structural Formula 110) was used in a light-emitting layer, and Light-emitting element 4 in which 1,8CzP2A and 1,6mMemFLPAPrn that was a dopant (a light-emitting substance) were used in a light-emitting layer, were fabricated. Note that fabrication of Light-emitting elements 1 to 4 is described with reference to FIG. 18. Chemical formulae of the materials used in this example are shown below.

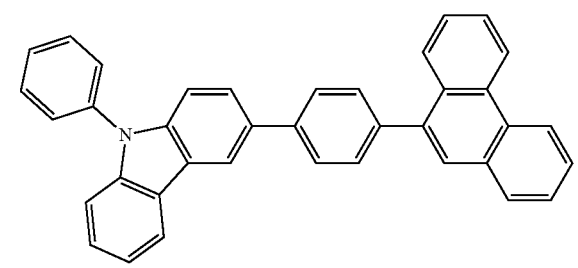

PCPPn

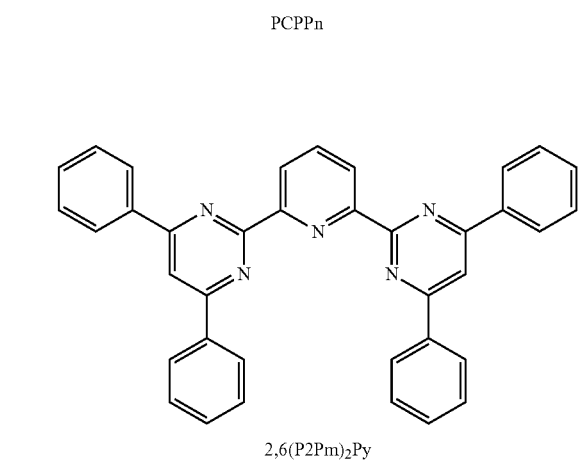

2,6(P2Pm)₂Py

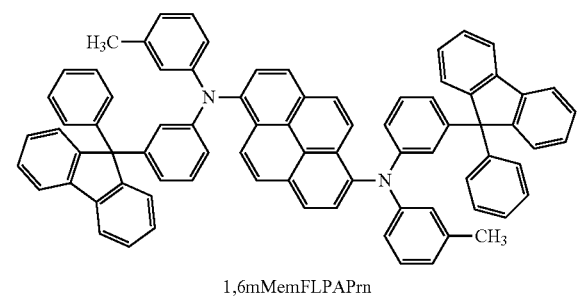

1,6mMemFLPAPrn

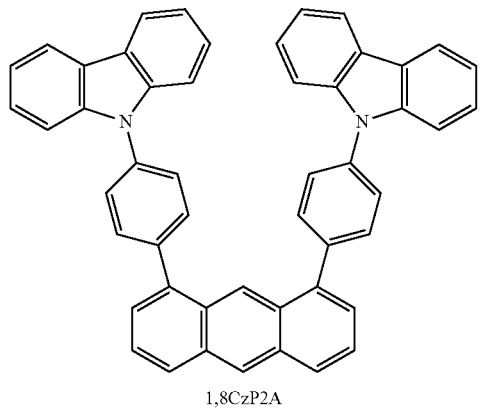

1,8CzP2A

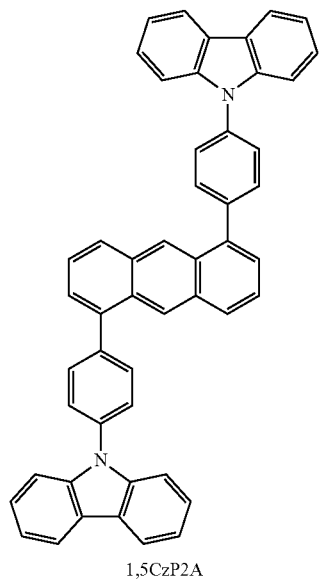

1,5CzP2A

<<Fabrication of Light-Emitting Elements 1 to 4>>

First, indium tin oxide (ITO) containing silicon oxide was deposited over a glass substrate 900 by a sputtering method, whereby a first electrode 901 functioning as an anode was formed. The thickness of the first electrode 901 was set to 70 nm and the area of the electrode was set to 2 mm×2 mm.

Next, as pretreatment for fabricating the light-emitting element 1 over the substrate 900, UV ozone treatment was performed for 370 seconds after washing of a surface of the substrate with water and baking that was performed at 200° C. for 1 hour.

After that, the substrate 900 was transferred into a vacuum evaporation apparatus where the pressure had been reduced to approximately $1\times10^{-4}$ Pa, and was subjected to vacuum baking at 170° C. for 30 minutes in a heating chamber of the vacuum evaporation apparatus. Then, the substrate 900 was cooled down for approximately 30 minutes.

Next, the substrate 900 over which the first electrode 901 was formed was fixed to a holder provided inside a vacuum evaporation apparatus so that the surface over which the first electrode was formed faced downward. In this example, a case will be described in which a hole-injection layer 911, a hole-transport layer 912, a light-emitting layer 913, an electron-transport layer 914, and an electron-injection layer 915 which are included in an EL layer 902 are sequentially formed by a vacuum evaporation method.

The pressure in the vacuum evaporation apparatus was reduced to $1\times10^{-4}$ Pa Pa. Then, 3-[4-(9-Phenanthryl)-phenyl]-9-phenyl-9H-carbazole (abbreviation: PCPPn) and molybdenum oxide were deposited by co-evaporation with a mass ratio of PCPPn to molybdenum oxide being 4:2, thereby forming the first hole-injection layer 911 on the first electrode 901. A thickness thereof was set to be 10 nm. Note that a co-evaporation method is an evaporation method in which a plurality of different substances is concurrently vaporized from respective different evaporation sources.

Next, PCPPn was deposited to a thickness of 20 nm by evaporation, thereby forming the hole-transport layer 912.

Next, the light-emitting layer 913 was formed on the hole-transport layer 912.

In the case of Light-emitting element 1, the light-emitting layer 913 was formed to a thickness of 25 nm by evaporation of 1,5CzP2A.

In the case of Light-emitting element 2, 1,5CzP2A and 1,6mMemFLPAPrn that was a dopant (a light-emitting substance) were deposited by co-evaporation so that the mass ratio of 1,5CzP2A and 1,6mMemFLPAPrn was 1:0.03, whereby the light-emitting layer 913 was formed to a thickness of 25 nm.

In the case of Light-emitting element 3, the light-emitting layer 913 was formed to a thickness of 25 nm by evaporation of 1,8CzP2A.

In the case of Light-emitting element 4, 1,8CzP2A and 1,6mMemFLPAPrn that was a dopant (a light-emitting substance) were deposited by co-evaporation so that the mass ratio of 1,8CzP2A and 1,6mMemFLPAPrn was 1:0.03, whereby the light-emitting layer 913 was formed to a thickness of 25 nm.

Next, over the light-emitting layer 913, 2,2'-(pyridine-2, 6-diyl)bis(4,6-diphenylpyrimidine) (abbreviation: 2,6 (P2Pm)2Py) was deposited to a thickness of 25 nm as the electron-transport layer 914.

Furthermore, lithium fluoride was deposited by evaporation to a thickness of 1 nm over the electron-transport layer 914, whereby the electron-injection layer 915 was formed.

Lastly, aluminum was deposited to a thickness of 200 nm over the electron-injection layer 915, whereby a second electrode 903 serving as a cathode was formed. Thus, Light-emitting elements 2 and 4 were fabricated. It is to be noted that an evaporation method using resistive heating was employed for all the evaporation steps.

Table 1 shows element structures of Light-emitting elements 1 to 4 obtained by the above steps.

TABLE 1

| | First electrode | Hole-injection layer | Hole-transport layer | Light-emitting layer | Electron-transport layer | Electron-injection layer | Second electrode |
|---|---|---|---|---|---|---|---|
| Light-emitting element 1 | ITO (70 nm) | PCPPn:MoOx (4:2 10 nm) | PCPPn (20 nm) | 1,5CzPA | 2,6(P2Pm) 2Py (25 nm) | LiF (1 nm) | Al (200 nm) |

TABLE 1-continued

| | First electrode | Hole-injection layer | Hole-transport layer | Light-emitting layer | Electron-transport layer | Electron-injection layer | Second electrode |
|---|---|---|---|---|---|---|---|
| Light-emitting element 2 | | | | * | | | |
| Light-emitting element 3 | | | | 1,8CzPA | | | |
| Light-emitting element 4 | | | | ** | | | |

* 1,5CzPA: 1,6mMemFLPAPrn (1:0.03 25 nm)
** 1,8CzPA: 1,6mMemFLPAPrn (1:0.03 25 nm)

The fabricated Light-emitting elements 1 to 4 were sealed in a glove box under a nitrogen atmosphere so as not to be exposed to the air (a sealant was applied to surround the elements, and at the time of sealing, UV treatment was performed and heat treatment was performed at 80° C. for 1 hour).

<Delayed Fluorescence Measurement of Light-Emitting Element>

Delayed fluorescence measurement was performed on Light-emitting elements 1 to 4. A picosecond fluorescence lifetime measurement system (manufactured by Hamamatsu Photonics K.K.) was used for the measurement. To measure the lifetimes of fluorescence obtained from the light-emitting layers of Light-emitting elements 1 to 4, the light-emitting elements were made to emit light by applying a square wave pulse voltage, and time-resolved measurements of light, which was attenuated from the falling of the voltage, were performed using a streak camera. The pulse voltage was applied at a frequency of 10 Hz. By integrating data obtained by repeated measurements, data with a high S/N ratio was obtained. The measurement was performed at room temperature (in an atmosphere kept at 23° C.) under the conditions of a pulse voltage of approximately 3 V, a pulse time width of 100 μsec, a negative bias voltage of −5 V, and a measurement time of 50 μsec.

Figure 19:
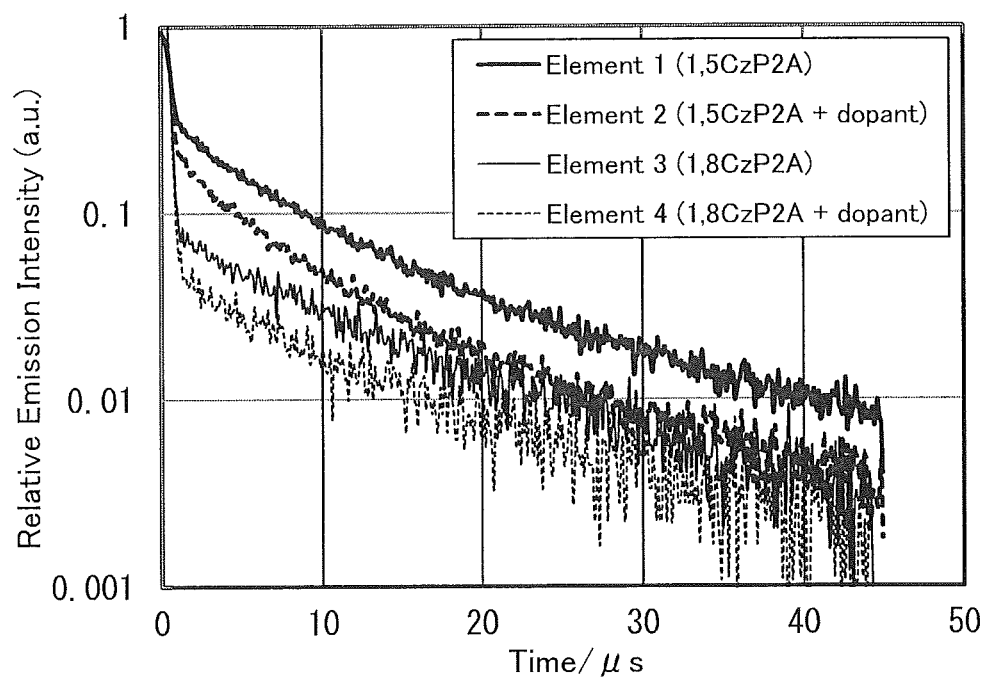
FIG. 19 shows attenuation curves.

The attenuation curves obtained by the measurement are shown in FIG. 19. In FIG. 19, the horizontal axis indicates the emission time (μs) elapsed after the falling of the pulse voltage and the vertical axis indicates the relative emission intensity (arbitrary unit). Fitting of the attenuation curves shown in FIG. 19 was performed using Formula (5).

$$L = \sum_{n=1} A_n \exp\left(-\frac{t}{a_n}\right) \quad (5)$$

In Formula (5), L and t represent normalized emission intensity and elapsed time, respectively.

As the results of the fitting of attenuation curves in FIG. 19, the fitting was able to be performed when n was 1 and 2 in Formula (5). The fitting of the attenuation curves was performed and the proportion of the delayed fluorescence component in the total emission obtained from each of Light-emitting elements 1 to 4 was calculated by extrapolation of the fitting curves to t=0. As a result, the proportions of the delayed fluorescence component in the total emission obtained from Light-emitting element 1, Light-emitting element 2, Light-emitting element 3, and Light-emitting element 4 were calculated to be 33%, 22%, 10%, and 6%, respectively. In other words, 5% or more of the delayed fluorescence component was observed in each of the Light-emitting elements 1 to 4.

Light-emitting element 1 and Light-emitting element 2 included 1,5CzP2A in the respective light-emitting layers, and Light-emitting element 3 and Light-emitting element 4 included 1,8CzP2A in the respective light-emitting layers. That is, it was found that the proportion of the delayed fluorescence component in each of Light-emitting element 1 and Light-emitting element 2 including 1,5CzP2A in its light-emitting layer was higher than that of the delayed fluorescence component in each of Light-emitting element 3 and Light-emitting element 4 including 1,8 CzP2A in its light-emitting layer.

Note that a high proportion (specifically, 15% or more) of delayed fluorescence components in Light-emitting element 1 and Light-emitting element 3 indicates that in 1,5CzP2A and 1,8CzP2A which are the organic compounds, energy transfer from triplet excitons to singlet excitons occurs at a relatively high probability and that probability of TTA is increased. Specifically, by using 1,5CzP2A having a particularly high proportion of delayed fluorescence components in the light-emitting layer, the light-emitting element with high probability of TTA was obtained. Note that this result agrees with the result in Embodiment 1 in which 1,5CzP2A having a larger oscillator strength (f) than that in 1,8CzP2A when comparison is performed using the oscillator strength (f), has a higher probability of TTA.

<<Operation Characteristics of Light-Emitting Elements 1 to 4>>

Operation characteristics of Light-emitting element 1 and Light-emitting element 3 in which dopant (a light-emitting substance) was not included in the respective light-emitting layers, and Light-emitting element 2 and Light-emitting element 4 in which dopant (a light-emitting substance) was included in the respective light-emitting layers were measured. It is to be noted that the measurements were performed at room temperature (in an atmosphere kept at 25° C.).

Figure 20:
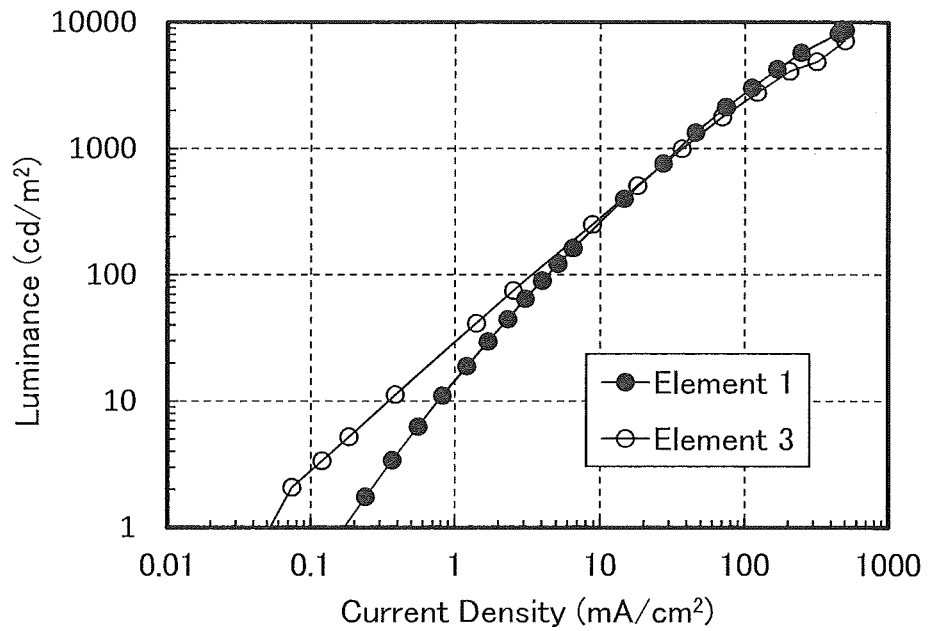
FIG. 20 is a graph showing the current density vs. luminance characteristics of Light-emitting element 1 and Light-emitting element 3.
Figure 21:
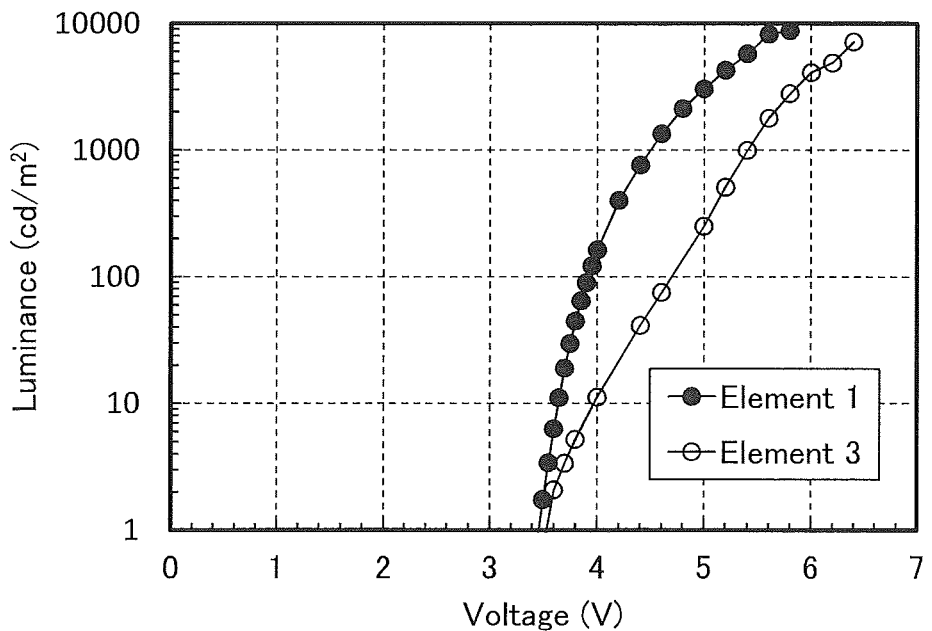
FIG. 21 is a graph showing the voltage vs. luminance characteristics of Light-emitting element 1 and Light-emitting element 3.
Figure 22:
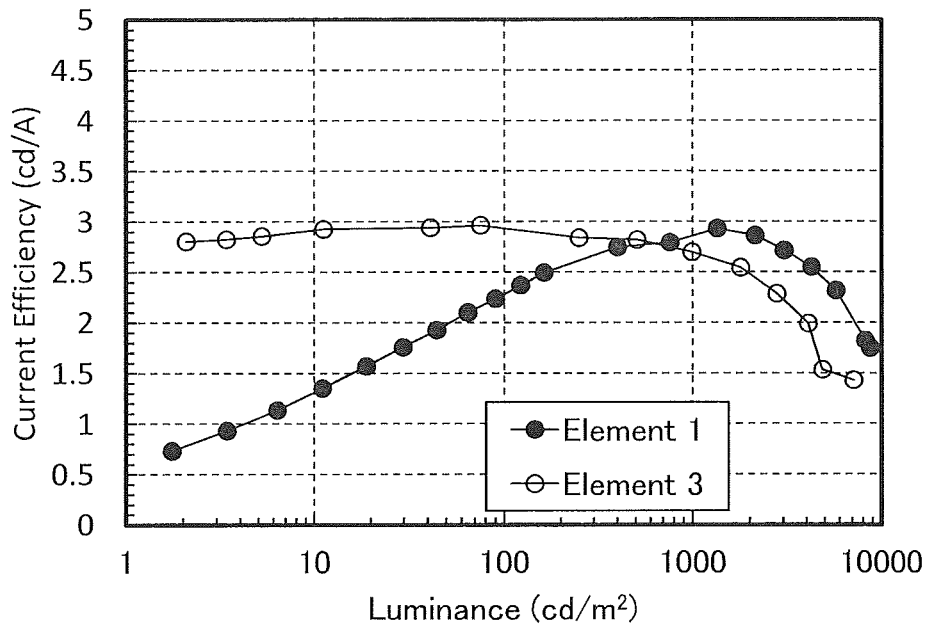
FIG. 22 is a graph showing the luminance vs. current efficiency characteristics of Light-emitting element 1 and Light-emitting element 3.
Figure 23:
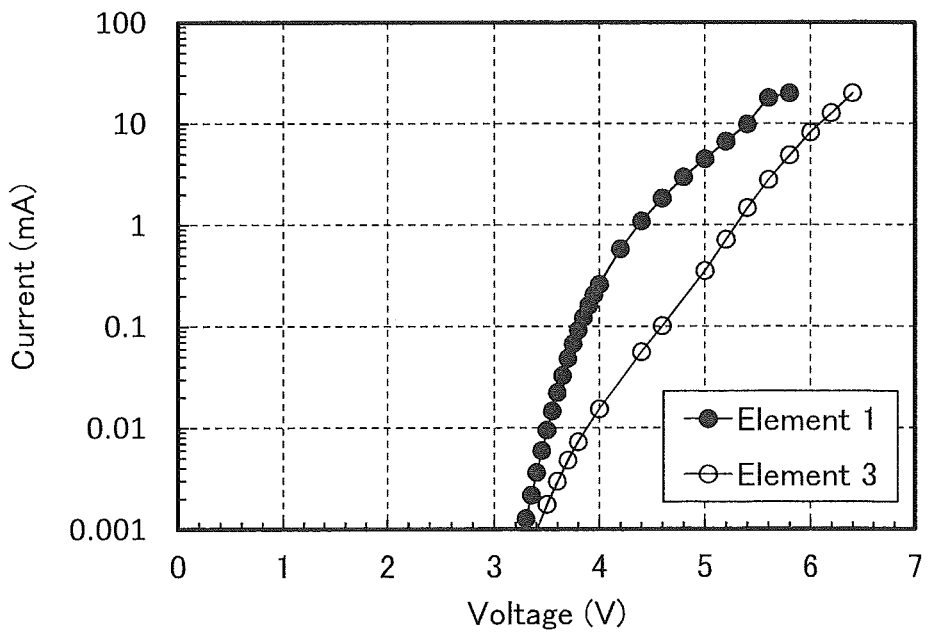
FIG. 23 is a graph showing voltage-current characteristics of Light-emitting element 1 and Light-emitting element 3.

FIG. 20 shows current density-luminance characteristics of Light-emitting element 1 and Light-emitting element 3 in which dopant (a light-emitting substance) was not included in the respective light-emitting layers. FIG. 21 shows voltage-luminance characteristics thereof. FIG. 22 shows luminance-current efficiency characteristics thereof. FIG. 23 shows voltage-current characteristics thereof.

Table 2 shows initial values of main characteristics of Light-emitting element 1 and Light-emitting element 3 at a luminance of about 1000 cd/m².

TABLE 2

|  | Voltage (V) | Current (mA) | Current density (mA/cm$^2$) | Chromaticity (x, y) | Luminance (cd/m$^2$) | Current density (cd/A) | Power efficiency (lm/W) | External quantum efficiency (%) |
| --- | --- | --- | --- | --- | --- | --- | --- | --- |
| Light-emitting elemet 1 | 4.4 | 1.1 | 27 | (0.15, 0.13) | 760 | 2.8 | 2.0 | 2.6 |
| Light-emitting element 3 | 5.4 | 1.5 | 37 | (0.15, 0.11) | 1000 | 2.7 | 1.6 | 2.8 |

Figure 24:
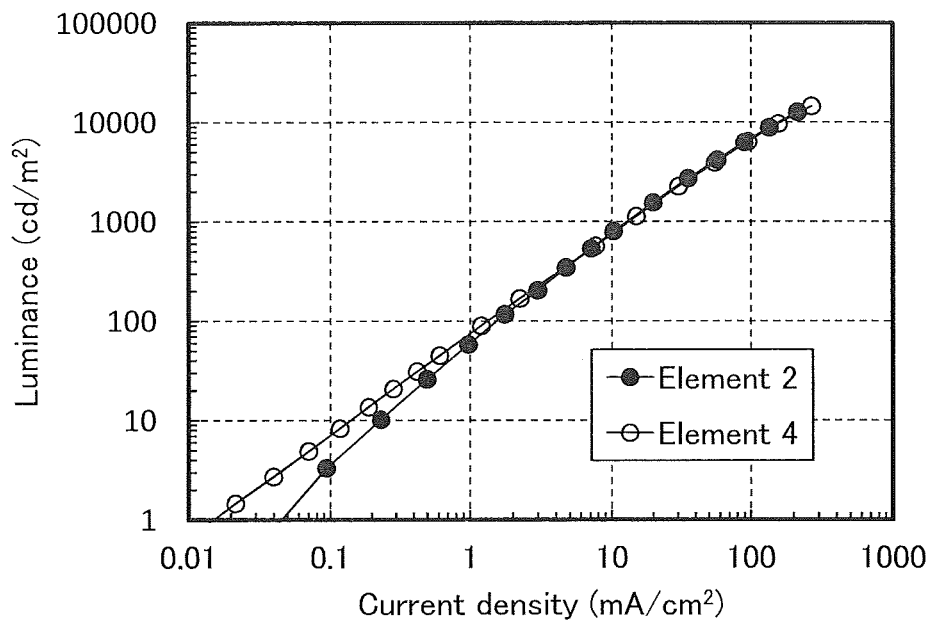
FIG. 24 is a graph the current density vs. luminance characteristics of Light-emitting element 2 and Light-emitting element 4.
Figure 25:
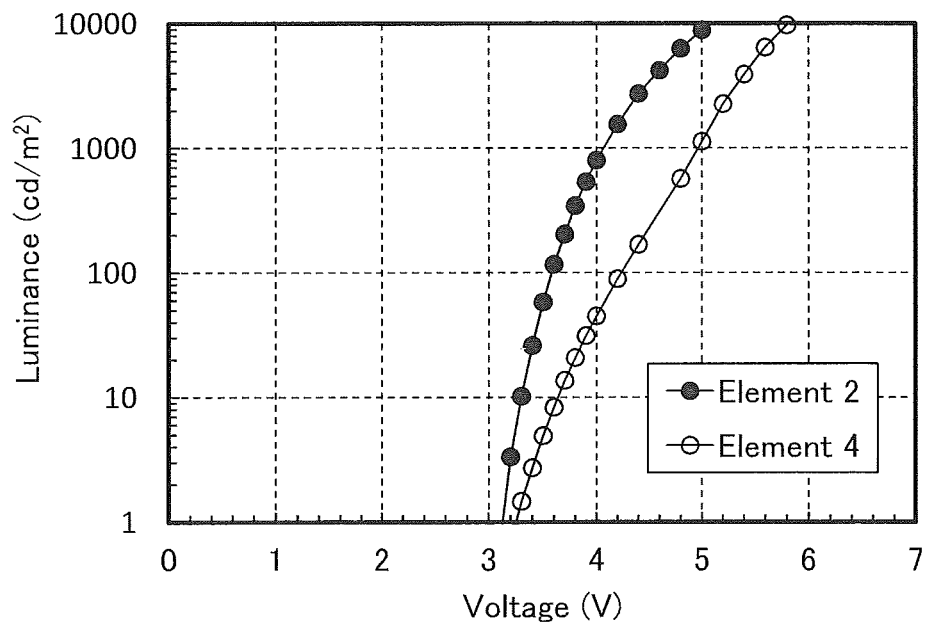
FIG. 25 is a graph showing the voltage vs. luminance characteristics of Light-emitting element 2 and the Light-emitting element 4.
Figure 26:
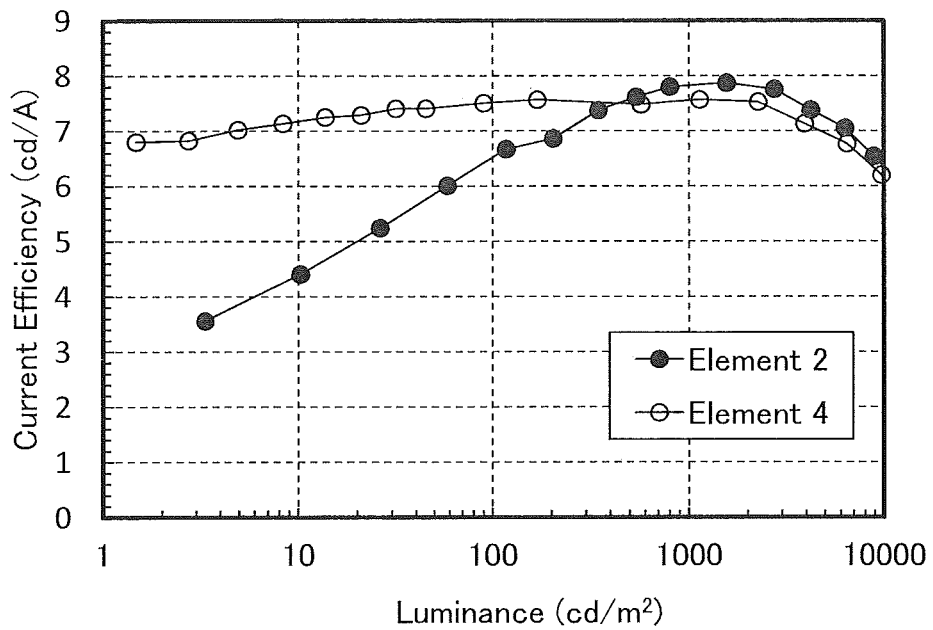
FIG. 26 is a graph showing the luminance vs. current efficiency characteristics of Light-emitting element 2 and Light-emitting element 4.
Figure 27:
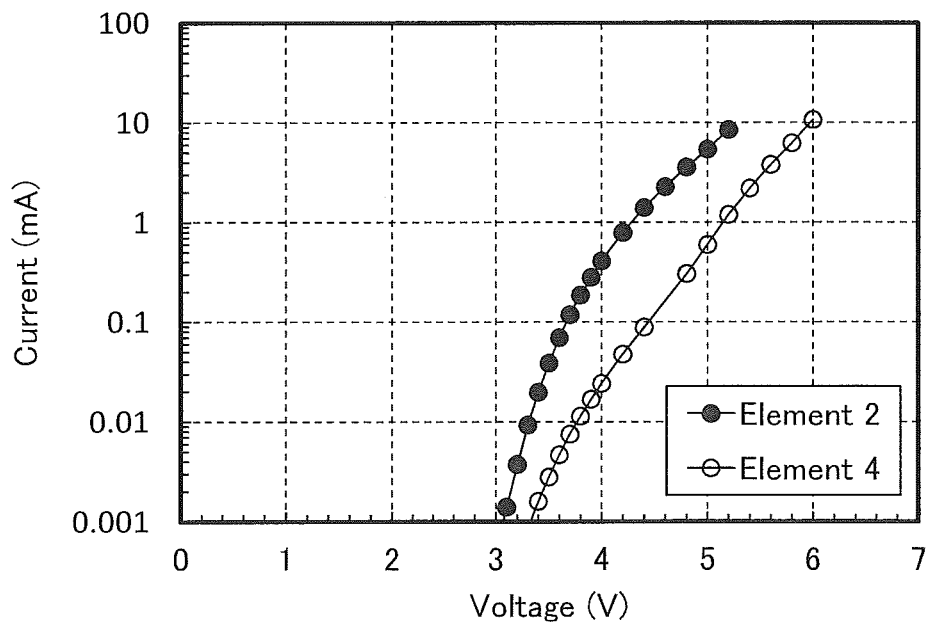
FIG. 27 is a graph showing voltage-current characteristics of Light-emitting element 2 and Light-emitting element 4.

FIG. 24 shows current density-luminance characteristics of Light-emitting elements 2 and 4, FIG. 25 shows voltage-luminance characteristics thereof, FIG. 26 shows luminance-current efficiency characteristics thereof, and FIG. 27 shows voltage-current characteristics thereof.

Table 4 shows initial values of main characteristics of Light-emitting elements 2 and 3 at a luminance of approximately 1000 cd/m$^2$.

TABLE 3

|  | Voltage (V) | Current (mA) | Current density (mA/cm$^2$) | Chromaticity (x, y) | Luminance (cd/m$^2$) | Current density (cd/A) | Power efficiency (lm/W) | External quantum efficiency (%) |
| --- | --- | --- | --- | --- | --- | --- | --- | --- |
| Light-emitting elemet 2 | 4.0 | 0.41 | 10 | (0.14, 0.15) | 800 | 7.8 | 6.1 | 7.0 |
| Light-emitting element 4 | 5.0 | 0.60 | 15 | (0.14, 0.16) | 1100 | 7.6 | 4.8 | 6.5 |

When the external quantum efficiencies of Light-emitting elements 2 and 4 containing dopant (here, 1,6mMemFLPA-Prn) are compared with each other, Light-emitting element 2 in which 1,5CzP2A was used as a host material used in the light-emitting layer of the light-emitting element had a higher external quantum efficiency than that of Light-emitting element 4. This indicated that the use of the material (1,5CzP2A) having a larger oscillator strength (f) was one factor allowing easy occurrence of TTA.

Figure 28:
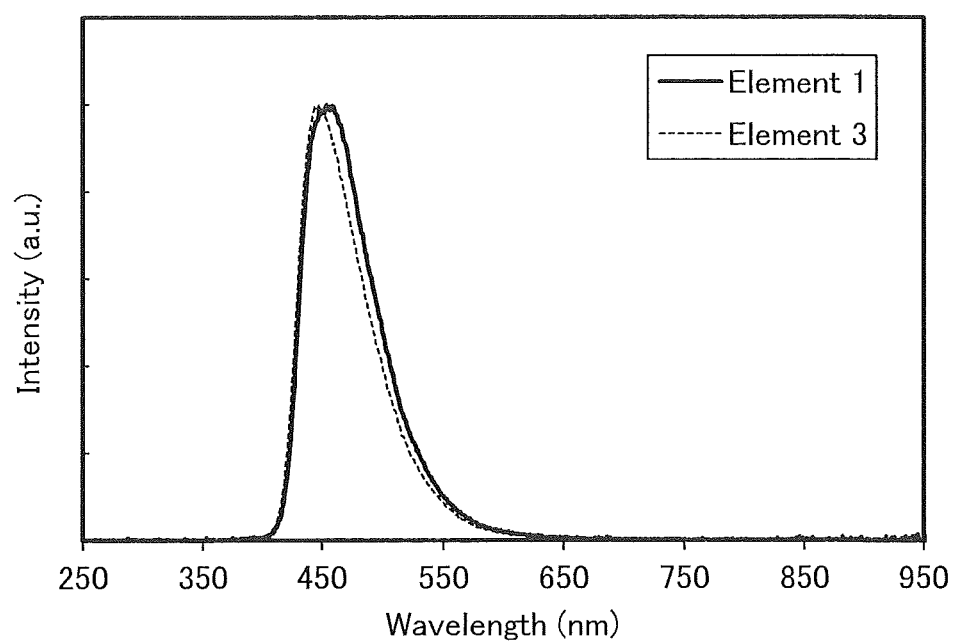
FIG. 28 shows emission spectra of Light-emitting element 1 and Light-emitting element 3.
Figure 29:
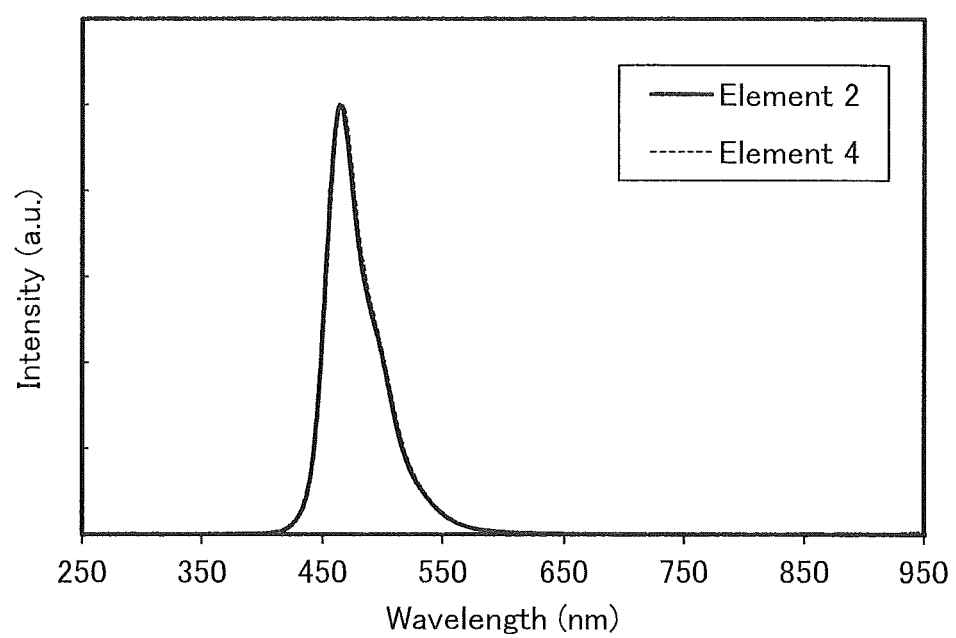
FIG. 29 shows emission spectra of Light-emitting element 2 and Light-emitting element 4.

FIG. 28 shows emission spectra of Light-emitting elements 1 and 3 to which current was applied at a current density of 25 mA/cm$^2$. FIG. 29 shows an emission spectrum of Light-emitting elements 2 and 4, to which current was applied at a current density of 25 mA/cm$^2$.

Example 2

Synthesis Example 1

In this example, a synthesis example of an organic compound, 1,5-bis[4-(9H-carbazole-9-yl)phenyl]anthracene (abbreviation: 1,5CzP2A) (Structural Formula:100) is described. Note that chemical formula of 1,5CzP2A is shown below.

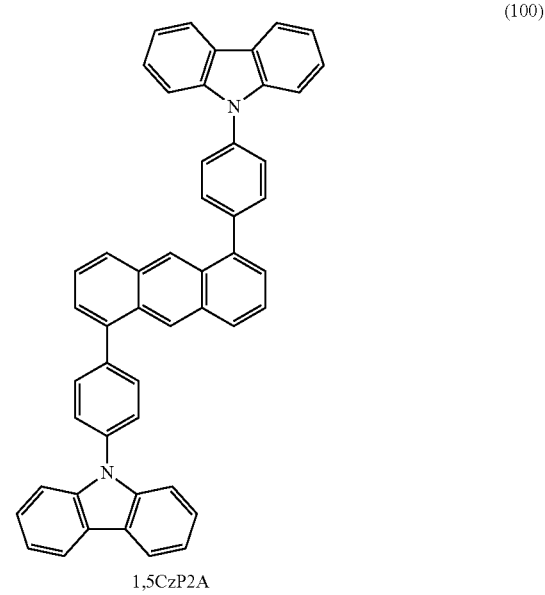 [SMILES: c1cc(-c2ccc(-n3c4ccccc4c4ccccc43)cc2)c2cc3cccc(-c4ccc(-n5c6ccccc6c6ccccc65)cc4)c3cc2c1]

(100)

1,5CzP2A

<Synthesis of 1,5CzP2A>

A mixture of 1.2 g (3.6 mmol) of dibromoanthracene, 2.3 g (7.9 mmol) of 4-(9H-carbazol-9-yl)phenylboronic acid, 2.2 g (16 mmol) of potassium carbonate, 30 mL of toluene, and 10 mL of ethanol, 8 mL of water, and 83 mg (71 µmol of tetrakis(triphenylphosphine)palladium(0) was stirred under a nitrogen stream at 90° C. for 14 hours.

After the stirring, the mixture was filtered, the obtained solid was washed with water and ethanol and then collected. This solid was purified by silica gel column chromatography (developing solvent: toluene). The purified solid was recrystallized, so that 2.0 g of a pale yellow solid was obtained in a yield of 86%.

The 2.0 g of obtained solid was purified by a train sublimation method under a pressure of 2.7 Pa in an argon stream at 343° C. After the purification, 1.8 g of a pale yellow solid was obtained at a collection rate of 90%. Synthesis scheme (a) of the above synthesis method is shown below.

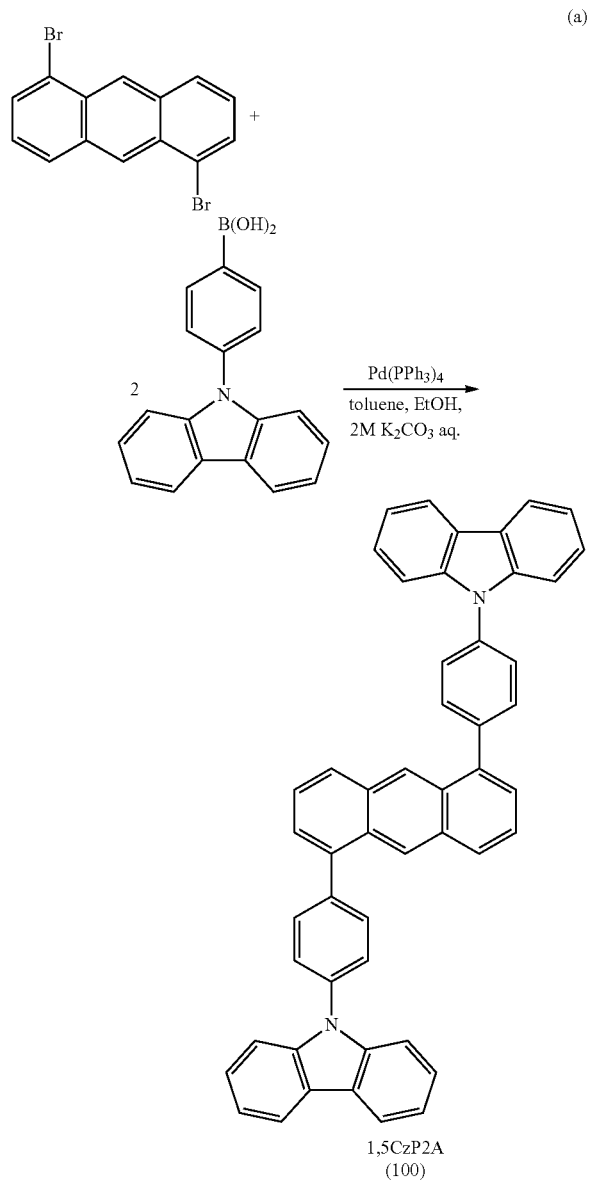

(a)

Figure 30A:
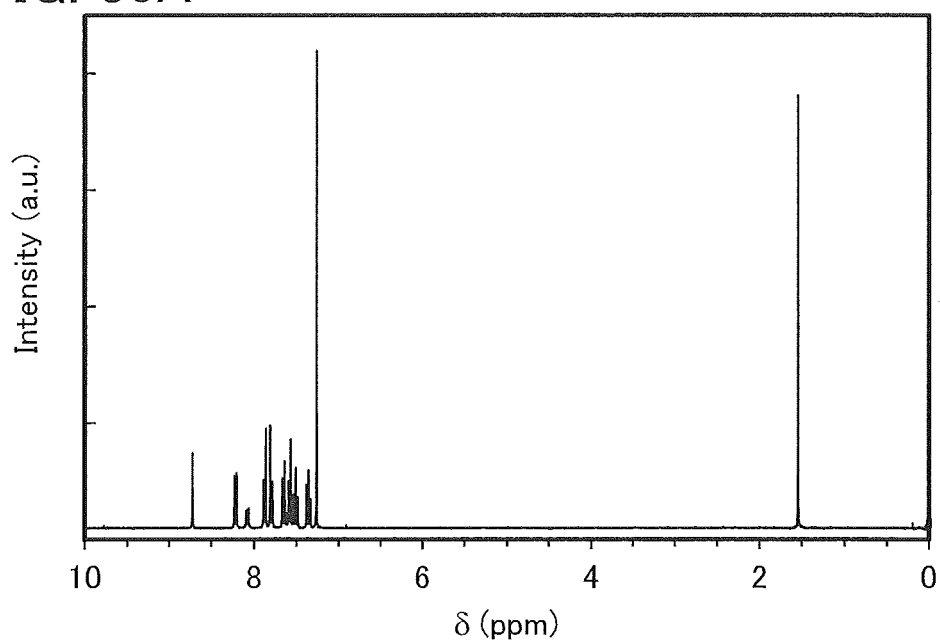
FIGS. 30A and 30B are $^1$H NMR charts of an organic compound represented by Structural Formula (100)
Figure 30B:
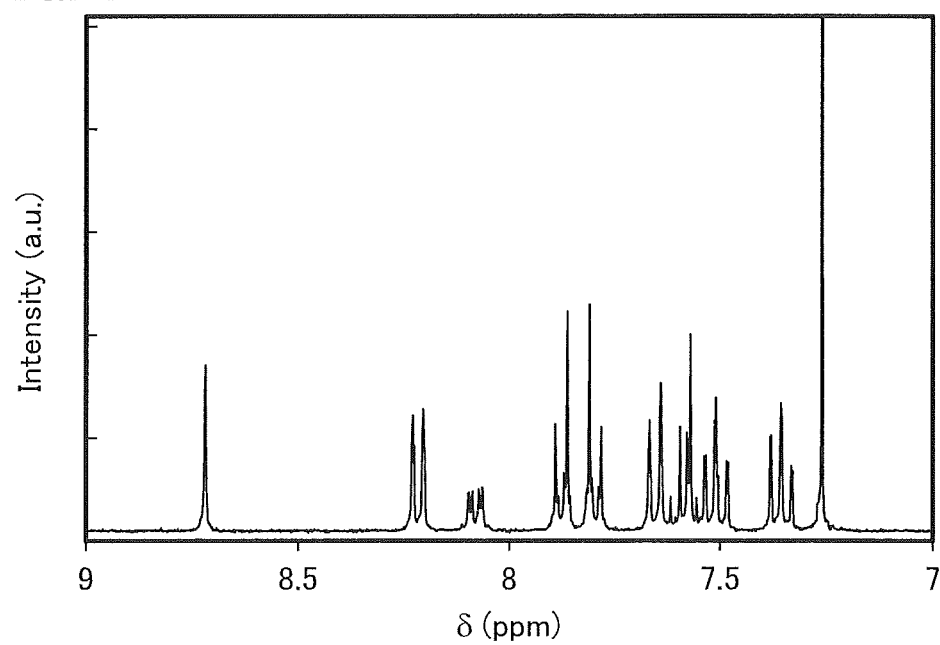

The following shows analysis results by nuclear magnetic resonance ($^1$H-NMR) spectroscopy of the pale yellow solid obtained by the above-described synthesis method. A $^1$H-NMR chart is shown in FIGS. 30A and 30B. The $^1$H NMR charts revealed that 1,5CzP2A, the organic compound of one embodiment of the present invention represented by Structural Formula (100), was obtained in Synthesis Example 1.

$^1$H-NMR (CDCl$_3$, 300 MHz): δ=7.36 (t, $J_1$=7.8 Hz, 4H), 7.51 (t, $J_1$=8.4 Hz, 4H), 7.57 (s, 2H), 7.58 (dd, $J_1$=6.9 Hz, $J_2$=11.7 Hz, 2H), 7.65 (d, $J_1$=7.8 Hz, 4H), 7.80 (d, $J_1$=8.4 Hz, 4H), 7.88 (d, $J_1$=8.7 Hz, 4H), 8.07 (dd, $J_1$=2.4 Hz, $J_2$=6.6 Hz, 2H), 8.22 (dd, $J_1$=7.5H, 4H), 8.72 (s=2H).

Figure 31A:
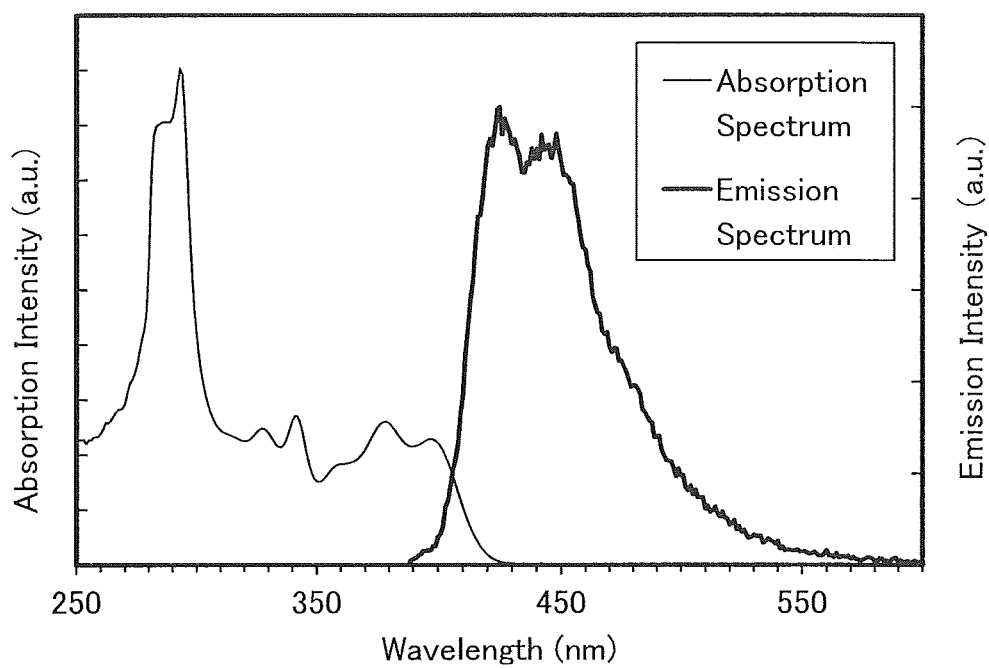
FIGS. 31A and 31B shows an ultraviolet-visible absorption spectrum and an emission spectrum of the organic compound represented by Structural Formula (100)
Figure 31B:
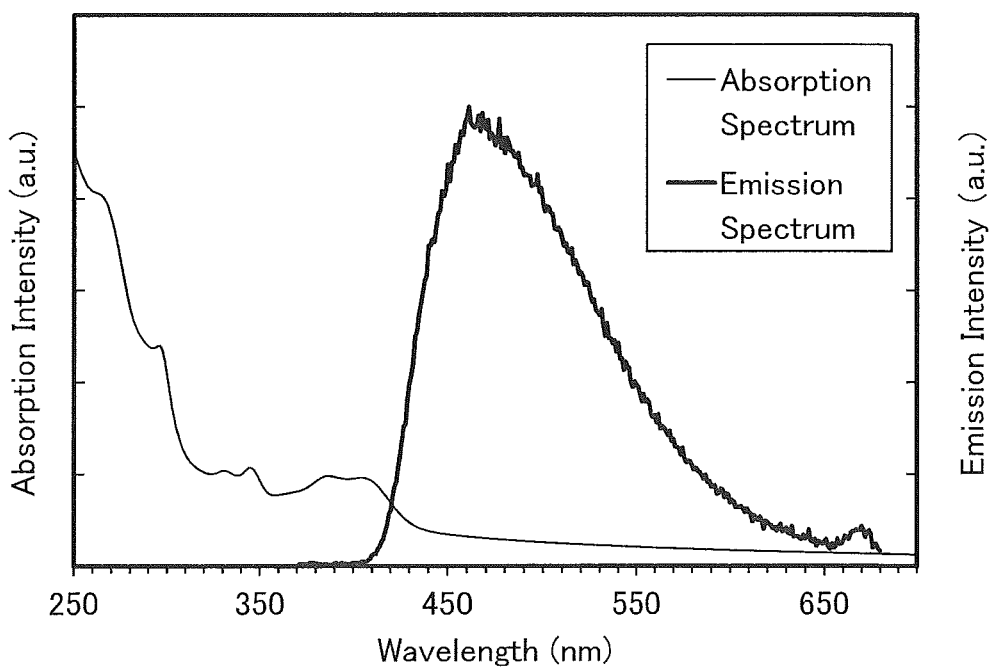

Next, ultraviolet-visible absorption spectra (hereinafter simply referred to as "absorption spectra") and emission spectra of 1,5CzP2A in a toluene solution and 1,5CzP2A in a solid thin film were measured. The solid thin film was formed over a quartz substrate by a vacuum evaporation method. The absorption spectra were measured using an ultraviolet-visible light spectrophotometer (V-550 type manufactured by JASCO Corporation). The emission spectra were measured using a fluorescence spectrophotometer (FS920 manufactured by Hamamatsu Photonics K.K.). FIG. 31A shows the obtained absorption and emission spectra of 1,5CzP2A in the toluene solution. The horizontal axis represents wavelength, and the vertical axis represents absorption intensity. FIG. 31B shows the obtained absorption and emission spectra of 1,5CzP2A in the solid thin film. The horizontal axis represents wavelength, and the vertical axis represents absorption intensity. The absorption spectrum shown in FIG. 31A is a result obtained by subtraction of an absorption spectrum of toluene only put in a quartz cell from the measured absorption spectrum of the toluene solution in a quartz cell. The absorption spectrum of the thin film in FIG. 31B was obtained by subtraction of an absorption spectrum of the quartz substrate from an absorption spectrum of the quartz on which 1,5CzP2A was deposited.

FIG. 31A shows that 1,5CzP2A in the toluene solution has absorption peaks at around 287 nm, 293 nm, 327 nm, 341 nm, 359 nm, 378 nm, and 397 nm, and emission wavelength peaks at around 425 nm and 448 nm. (The excitation wavelength: 379 nm). FIG. 31B shows that 1,5CzP2A in the solid thin film has absorption peaks at around 265 nm, 286 nm, 296 nm, 314 nm, 331 nm, 345 nm, 369 nm, 387 nm, and 404 nm, and an emission wavelength peak at around 462 nm. (The excitation wavelength: 345 nm).

Figure 32:
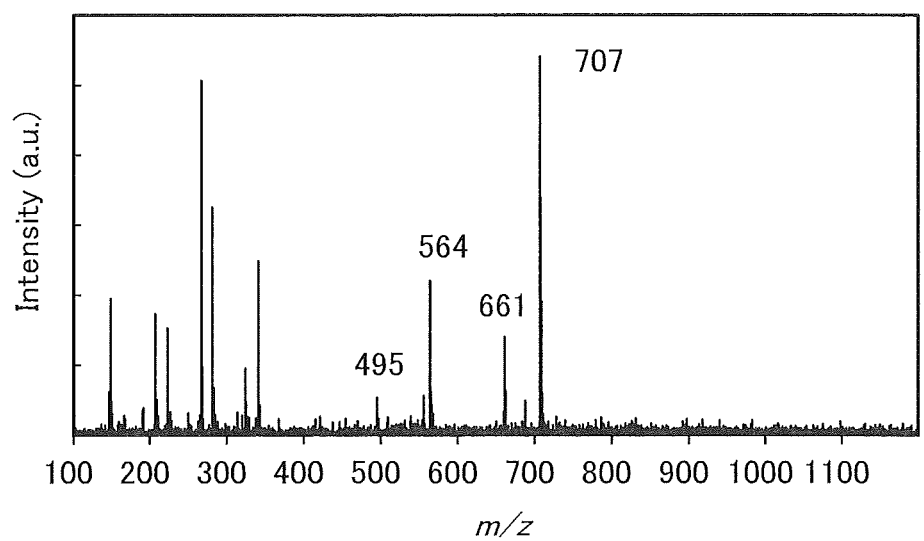
FIG. 32 shows results of LC/MS analysis of the organic compound represented by Structural Formula (100)

Next, LC/MS analysis was performed. FIG. 32 shows the measurement results.

In the LC/MS analysis, liquid chromatography (LC) separation was carried out with ACQUITY UPLC® (manufactured by Waters Corporation) and mass spectrometry (MS) analysis was carried out with Xevo G2 Tof MS (manufactured by Waters Corporation).

For the LC separation, Acquity UPLC BEH C8 (2.1×100 mm, 1.7 μm) was used as a column, and a mixed solution of acetonitrile and a 0.1% formic acid aqueous solution was used for a mobile phase.

In the MS analysis, ionization was carried out by an electrospray ionization (ESI) method, and the analysis was performed in a positive mode. A component that underwent the ionization was collided with an argon gas in a collision cell to dissociate into product ions. Energy (collision energy) for the collision with argon was 50 eV. The mass range for the measurement was m/z=100 to 1200.

The result shows that precursor ions of 1,5CzP2A were detected around m/z=661, and product ions of 1,5CzP2A were detected around m/z=495 and m/z=707. These results are characteristically derived from 1,5CzP2A and thus can be regarded as important data in identification of 1,5CzP2A contained in the mixture.

Note that the product ion around m/z=495 is presumed to be a hydrogen ion adduct of a radical expressed as $C_{38}H_{25}N.^+$ in the state where one carbazole is dissociated, and the product ion around m/z=707 is presumed to be acetonitrile and a hydrogen ion adduct. These indicate that a terminal of 1,5CzP2A has a carbazole skeleton and that acetonitrile is easily added. Note that acetonitrile was used for sample adjustment at the time of the analysis and for the mobile phase. Note that there is a possibility that the above m/z values±1 are detected as protonation or deprotonation products of the product ions.

Note that the synthesis method of 1,5CzP2A which is the organic compound of one embodiment of the present invention described in this example is a preferable example; however, the present invention is not limited to this example and another synthesis method can be employed.

The above-described organic compound, 1,5CzP2A can be used not only as a host material of the light-emitting layer but also as a light-emitting substance.

Example 3

Synthesis Example 2

In this example, a synthesis method of an organic compound, 1,8-bis[4-(9H-carbazole-9-yl)phenyl]anthracene (abbreviation: 1,8CzP2A) is described. Note that chemical formula of 1,8CzP2A is shown below.

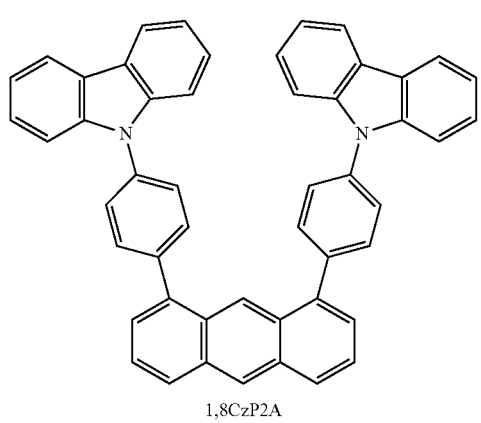

1,8CzP2A
(110)

<Synthesis of 1,8CzP2A>

In a 200 mL three-neck flask, a mixture of 1.2 g (3.7 mmol) of dibromoanthracene, 2.3 g (8.1 mmol) of 4-(9H-carbazol-9-yl)phenylboronic acid, 2.2 g (16 mmol) of potassium carbonate, 30 mL of toluene, and 10 mL of ethanol, 8 mL of water, and 85 mg (74 µmol) of tetrakis(triphenylphosphine)palladium(0) was stirred under a nitrogen stream at 90° C. for 14 hours.

After the stifling, the mixture was filtered, the obtained solid was washed with water and ethanol and then collected. This solid was purified by silica gel column chromatography (developing solvent: toluene). The purified solid was recrystallized by toluene, so that 2.3 g of a pale yellow solid was obtained in a yield of 93%. 2.0 g of the obtained solid was purified by a train sublimation method under a pressure of 2.7 Pa in an argon stream at 295° C. After the purification, 1.9 g of a pale yellow solid was obtained at a collection rate of 83%. Synthesis scheme (b) of the above synthesis method is shown below.

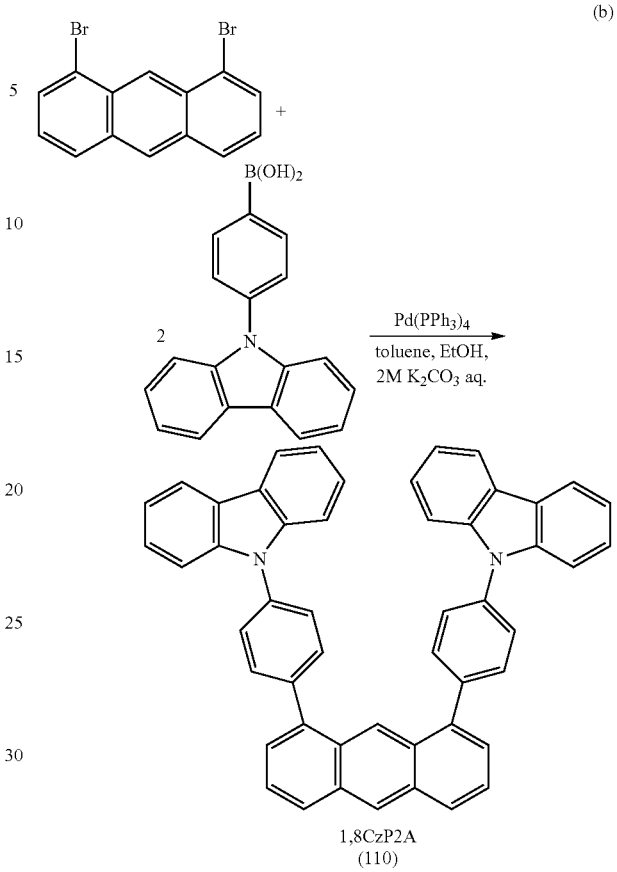

(b)

1,8CzP2A
(110)

Figure 33A:
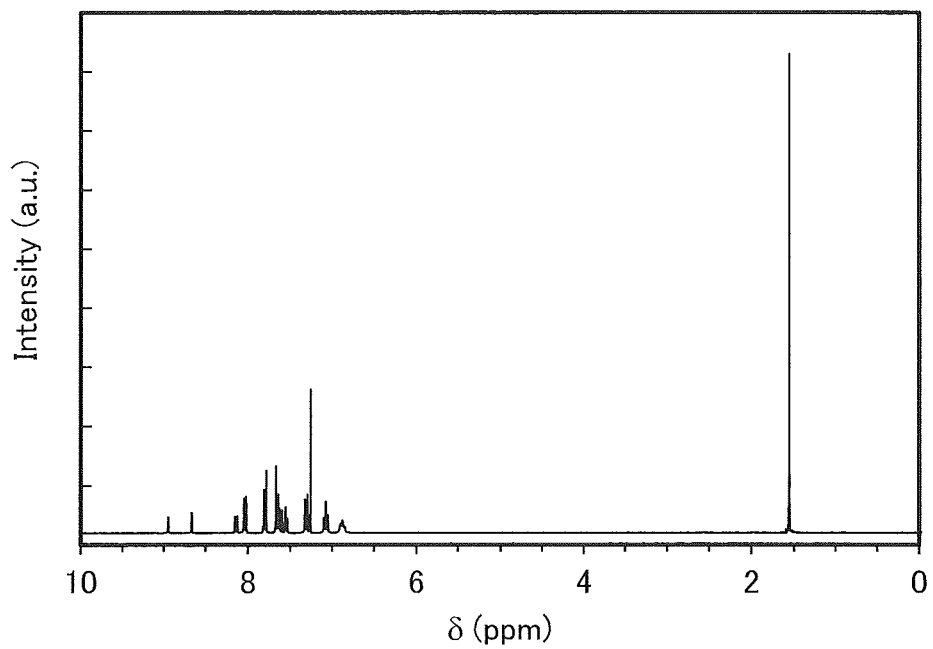
FIGS. 33A and 33B are $^1$H NMR charts of an organic compound represented by Structural Formula (110)
Figure 33B:
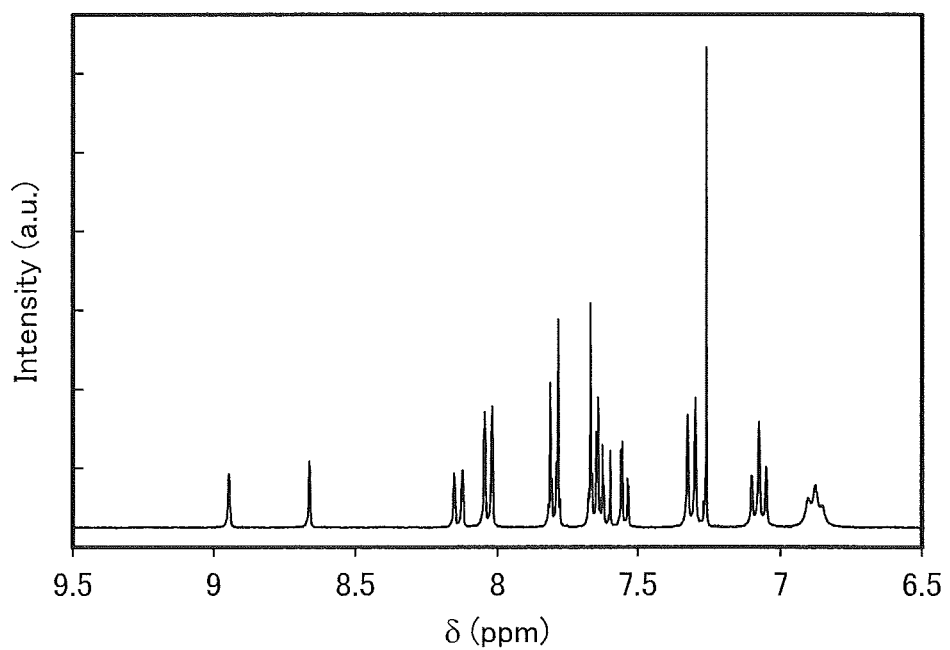

The following shows analysis results by nuclear magnetic resonance ($^1$H-NMR) spectroscopy of the pale yellow solid obtained by the above-described synthesis method. A $^1$H-NMR chart is shown in FIGS. 33A and 33B. The $^1$H-NMR charts revealed that 1,8CzP2A, the organic compound of one embodiment of the present invention represented by Structural Formula (110), was obtained in Synthesis Example 2.

$^1$H NMR (CDCl$_3$, 300 MHz): δ=6.88 (t, $J_1$=7.2 Hz, 4H), 7.08 (t, $J_1$=7.8 Hz, 4H), 7.31 (d, $J_1$=8.1 Hz, 4H), 7.55 (dd, $J_1$=1.5 Hz, $J_2$=6.9 Hz, 2H), 7.60-7.68 (m, 6H), 7.80 (d, $J_1$=8.1 Hz, 4H), 8.03 (d, $J_1$=7.8 Hz, 4H), 8.14 (d, $J_1$=7.8 Hz, 2H), 8.66 (s, 1H), 8.95 (s, 1H).

Figure 34A:
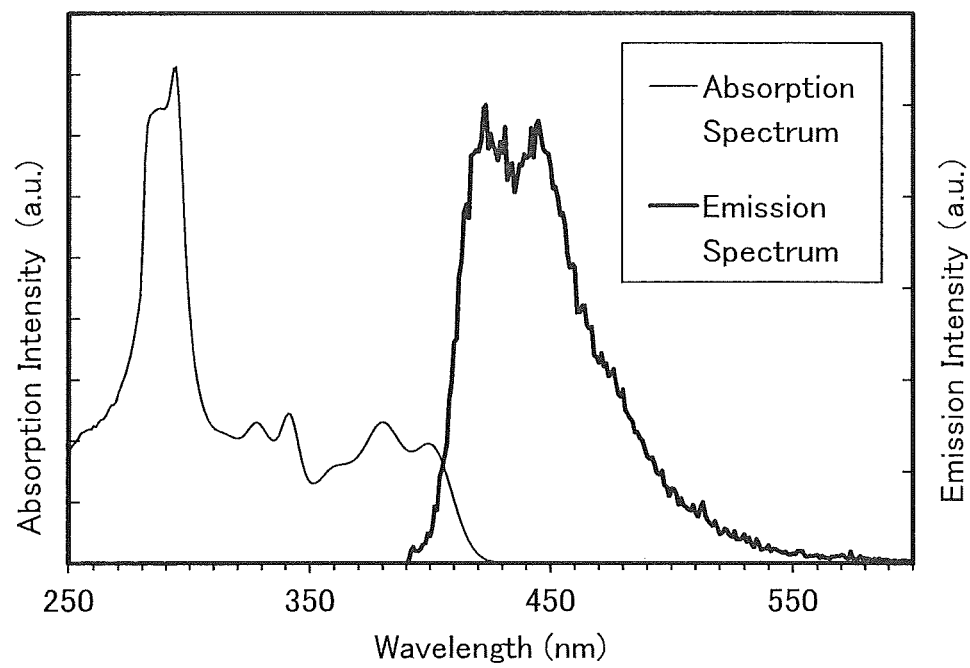
FIGS. 34A and 34B show ultraviolet-visible absorption spectra and emission spectra of the organic compound represented by Structural Formula (110)
Figure 34B:
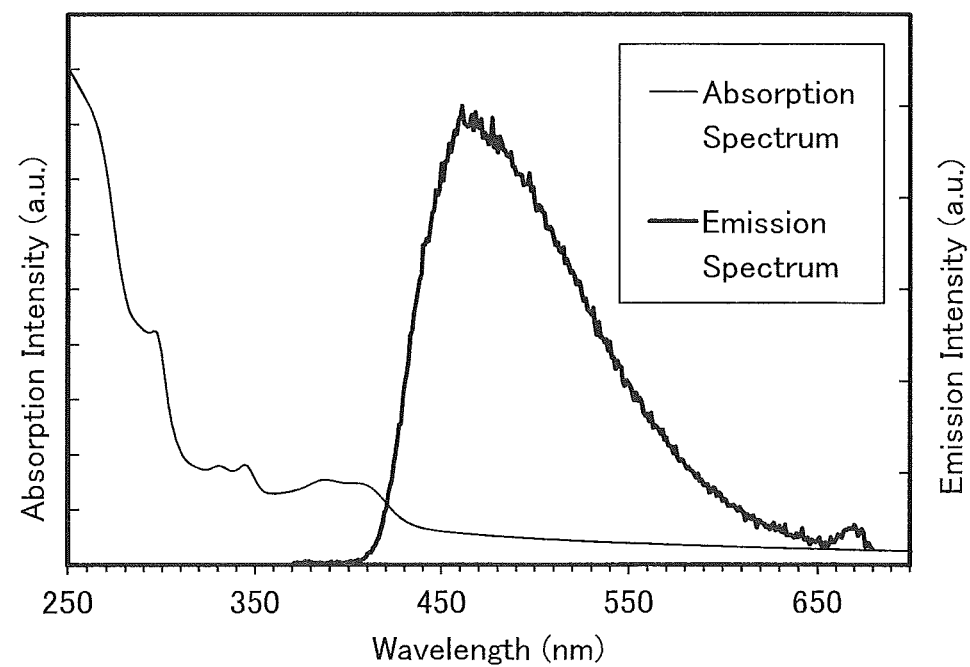

Next, ultraviolet-visible absorption spectra (hereinafter simply referred to as "absorption spectra") and emission spectra of 1,8CzP2A in a toluene solution and 1,8CzP2A in a solid thin film were measured. The toluene solution and the solid thin film were each measured in a manner similar to that in Example 2. FIG. 34A shows the obtained absorption and emission spectra of 1,8CzP2A in the toluene solution. The horizontal axis represents wavelength, and the vertical axis represents absorption intensity. FIG. 34B shows the obtained absorption and emission spectra of the solid thin film. The horizontal axis represents wavelength, and the vertical axis represents absorption intensity.

FIG. 34A shows that 1,8CzP2A in the toluene solution has absorption peaks at around 287 nm, 294 nm, 328 nm, 341 nm, 361 nm, 380 nm, and 399 nm, and emission wavelength peaks at around 423 nm and 445 nm. (The excitation wavelength: 381 nm). FIG. 34B shows that 1,8CzP2A in the solid thin film has absorption peaks at around 265 nm, 286 nm, 296 nm, 315 nm, 331 nm, 344 nm, 370 nm, 388 nm, and 404 nm, and an emission wavelength peak at around 468 nm. (The excitation wavelength: 345 nm).

Figure 35:
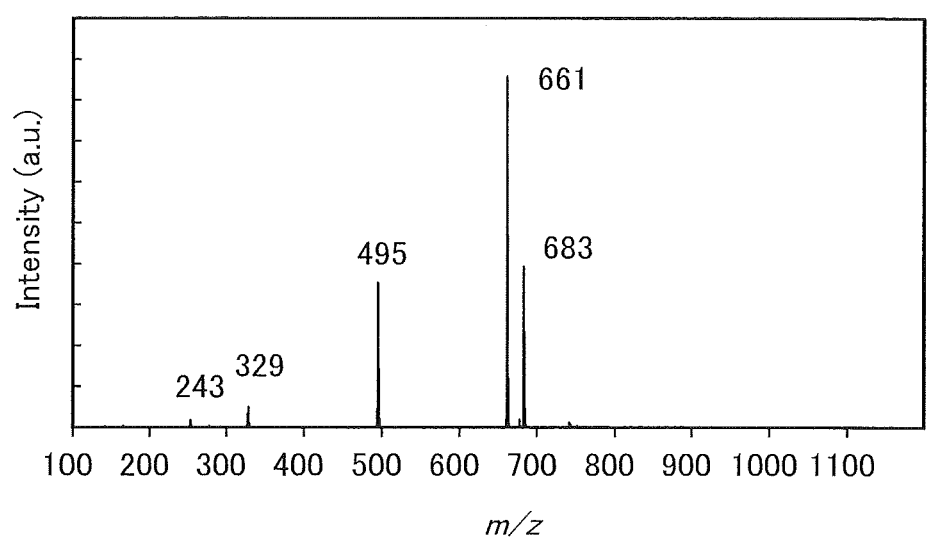
FIG. 35 shows results of LC/MS analysis of the organic compound represented by Structural Formula (110)

Next, LC/MS analysis was performed. The measurement method was similar to that used in Example 2. FIG. 35 shows the measurement results.

The result shows that precursor ions of 1,8CzP2A were detected around m/z=661, and product ions of 1,8CzP2A were detected around m/z=243, m/z=329, and m/z=495. The results are characteristically derived from 1,8CzP2A and thus can be regarded as important data in identification of 1,8CzP2A contained in a mixture.

Note that the product ion around m/z=243 is presumed to be a proton adduct of a radical of phenylcarbazole expressed as $C_{18}H_{13}N.^+$; the product ion around m/z=329 is presumed to be a hydrogen ion adduct of a biradical expressed as $C_{26}H_{172}.^+$ in the state where two carbazoles are dissociated; and the product ion around m/z=495 is presumed to be a hydrogen ion adduct of a radical expressed as $C_{38}H_{25}.^+$ in the state where one carbazole is dissociated. These indicate that a terminal of 1,8CzP2A includes two carbazole skeletons and a phenylcarbazole skeleton. Note that there is a possibility that the above m/z values±1 are detected as protonation or deprotonation products of the product ions.

Note that the synthesis method of 1,8CzP2A which is the organic compound of one embodiment of the present invention described in this example is a preferable example; however, the present invention is not limited to this example and another synthesis method can be employed.

The above-described organic compound, 1,8CzP2A can be used as not only as a host material of the light-emitting layer but also as a light-emitting substance.

This application is based on Japanese Patent Application serial no. 2015-146604 filed with Japan Patent Office on Jul. 24, 2015 and Japanese Patent Application serial no. 2016-006140 filed with Japan Patent Office on Jan. 15, 2016, the entire contents of which are hereby incorporated by reference.

What is claimed is:

1. A light-emitting element comprising:
an EL layer between an anode and a cathode,
wherein the EL layer includes a light-emitting layer,
wherein the light-emitting layer includes a first organic compound,
wherein a difference between a $T_1$ level of the first organic compound and one or more of $T_n$ levels of the first organic compound is less than the sum of the $T_1$ level and 0.6 eV,
wherein the first organic compound has a structure represented by General Formula (G1)

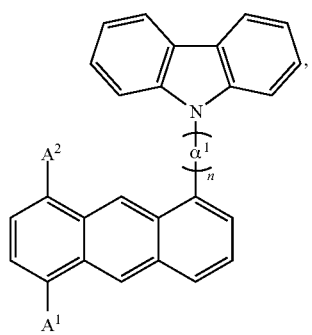

(G1)

wherein $\alpha^1$ represents a substituted or unsubstituted phenylene group, wherein n represents 1 or 2, wherein one of $A^1$ and $A^2$ is a first substituent represented by General Formula (G1-1)

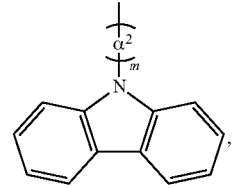

(G1-1)

wherein $\alpha^2$ represents a substituted or unsubstituted phenylene group, wherein m represents 1 or 2, and wherein the other of $A^1$ and $A^2$ is hydrogen or a second substituent different from the first substituent.

2. The light-emitting element according to claim 1, wherein an energy difference between the one or more of $T_n$ levels of the first organic compound and any one of an $S_1$ level and $S_n$ levels of the first organic compound is 1 eV or less.

3. The light-emitting element according to claim 1, wherein an oscillator strength for excitation from the $T_1$ level of the first organic compound to the one or more of $T_n$ levels of the first organic compound is 0.0015 or more.

4. The light-emitting element according to claim 1, wherein the first organic compound has Structural Formula (100) or Structural Formula (110).

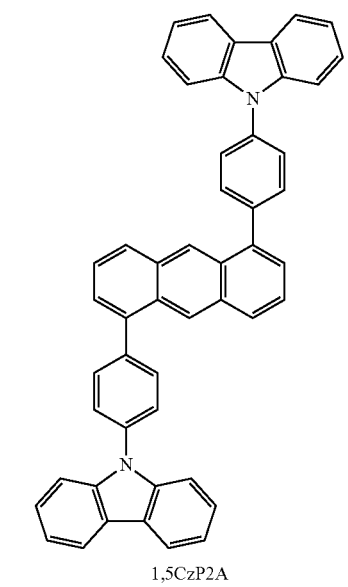

(100)

1,5CzP2A

-continued

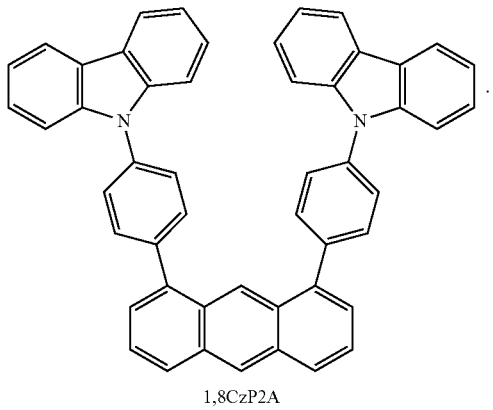

1,8CzP2A (110)

5. The light-emitting element according to claim 1,
wherein light emission from the light-emitting element includes a delayed fluorescence component, and
wherein an emission intensity of the delayed fluorescence component is 5% or more to that of a total amount of the light emission.

6. The light-emitting element according to claim 5,
wherein the light-emitting layer further includes a second organic compound,
wherein an $S_1$ level of the first organic compound is higher an $S_1$ level of the second organic compound, and
wherein the light emission from the light-emitting element is derived from the second organic compound.

7. The light-emitting element according to claim 6, wherein the second organic compound includes a pyrene skeleton.

8. The light-emitting element according to claim 6, wherein a $T_1$ level of the second organic compound is higher than the $T_1$ level of the first organic compound.

9. The light-emitting element according to claim 6,
wherein the EL layer further includes a hole-transport layer including a third organic compound,
wherein the hole-transport layer is located between the anode and the light-emitting layer and in contact with the light-emitting layer, and
wherein a $T_1$ level of the third organic compound included in the hole-transport layer is higher than the $T_1$ level of the first organic compound.

10. The light-emitting element according to claim 9,
wherein the EL layer further includes an electron-transport layer including a fourth organic compound,
wherein the electron-transport layer is located between the cathode and the light-emitting layer and in contact with the light-emitting layer, and
wherein a $T_1$ level of the fourth organic compound included in the electron-transport layer is higher than the $T_1$ level of the first organic compound.

11. A light-emitting device comprising:
the light-emitting element according to claim 1, and
one of a transistor and a substrate.

12. An electronic device comprising:
the light-emitting device according to claim 11, and
any one of microphone, a camera, an operation button, an external connection portion, and a speaker.

13. An electronic device comprising:
the light-emitting device according to claim 11, and
one of a housing and a touch sensor.

14. A lighting device comprising:
the light-emitting device according to claim 11, and
any one of a housing, a cover, and a support.

15. A lighting system comprising:
a sensor;
a control unit electrically connected to the sensor; and
a light-emitting element electrically connected to the control unit,
wherein information acquired by the sensor is input to the control unit,
wherein the control unit is configured to drive the light-emitting element based on the information,
wherein the light-emitting element includes an EL layer between an anode and a cathode,
wherein the EL layer includes a light-emitting layer,
wherein the light-emitting layer includes a first organic compound,
wherein a difference between a $T_1$ level of the first organic compound and one or more of $T_n$ levels of the first organic compound is less than the sum of the $T_1$ level and 0.6 eV,
wherein the first organic compound has a structure represented by General Formula (G1)

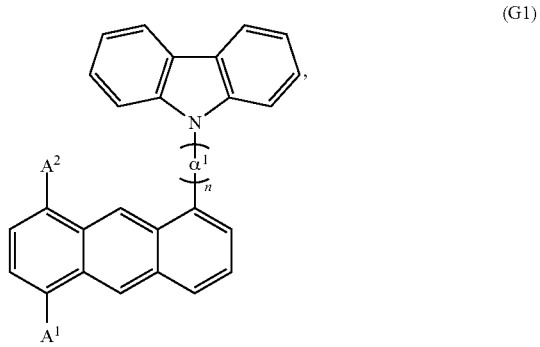

(G1)

wherein $\alpha^1$ represents a substituted or unsubstituted phenylene group,
wherein n represents 1 or 2,
wherein one of $A^1$ and $A^2$ is a first substituent represented by General Formula (G1-1)

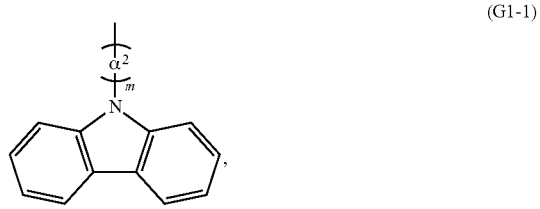

(G1-1)

wherein $\alpha^2$ represents a substituted or unsubstituted phenylene group,
wherein m represents 1 or 2, and
wherein the other of $A^1$ and $A^2$ is hydrogen or a second substituent different from the first substituent.

16. The lighting system according to claim 15, wherein an energy difference between the one or more of $T_n$ levels of the first organic compound and any one of an $S_1$ level and $S_n$ levels of the first organic compound is 1 eV or less.

17. A lighting system comprising:
a sensor;
a control unit; and
a light-emitting element,
wherein the control unit includes a communication unit, a CPU, and a memory,
wherein the memory includes a program for driving the light-emitting element based on exterior information,
wherein the communication unit is configured to send the exterior information acquired by the sensor to the CPU,
wherein the CPU is configured to drive the light-emitting element by reading out the program from the memory and executing the program,
wherein the light-emitting element includes an EL layer between an anode and a cathode,
wherein the EL layer includes a light-emitting layer,
wherein the light-emitting layer includes a first organic compound,
wherein a difference between a $T_1$ level of the first organic compound and one or more of $T_n$ levels of the first organic compound is less than the sum of the $T_1$ level and 0.6 eV,
wherein the first organic compound has a structure represented by General Formula (G1)

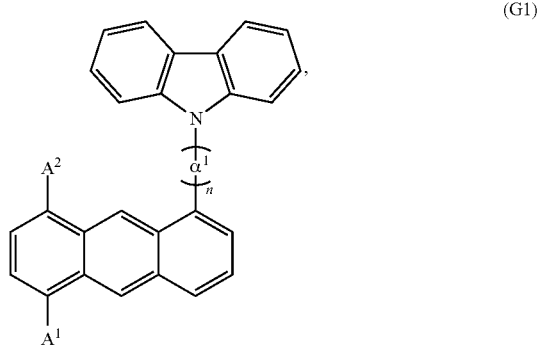

(G1)

wherein $\alpha^1$ represents a substituted or unsubstituted phenylene group,
wherein n represents 1 or 2,
wherein one of $A^1$ and $A^2$ is a first substituent represented by General Formula (G1-1)

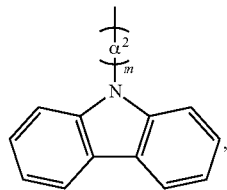

(G1-1)

wherein $\alpha^2$ represents a substituted or unsubstituted phenylene group,
wherein m represents 1 or 2, and
wherein the other of $A^1$ and $A^2$ is hydrogen or a second substituent different from the first substituent.

18. The lighting system according to claim 17, wherein an energy difference between the one or more of $T_n$ levels of the first organic compound and any one of an $S_1$ level and $S_n$ levels of the first organic compound is 1 eV or less.

19. The light-emitting element according to claim 1, wherein the second substituent includes at least one of an alkyl group having 1 to 6 carbon atoms, a cycloalkyl group having 1 to 6 carbon atoms, an alkylphenyl group, and a phenyl group.

20. The light-emitting element according to claim 1, wherein, in General Formula (G1), $A^1$ is the first substituent represented by General Formula (G1-1) and $A^2$ is hydrogen or the second substituent.

21. The lighting system according to claim 15, wherein the second substituent includes at least one of an alkyl group having 1 to 6 carbon atoms, a cycloalkyl group having 1 to 6 carbon atoms, an alkylphenyl group, and a phenyl group.

22. The lighting system according to claim 15, wherein, in General Formula (G1), $A^1$ is the first substituent represented by General Formula (G1-1) and $A^2$ is hydrogen or the second substituent.

23. The lighting system according to claim 17, wherein the second substituent includes at least one of an alkyl group having 1 to 6 carbon atoms, a cycloalkyl group having 1 to 6 carbon atoms, an alkylphenyl group, and a phenyl group.

24. The lighting system according to claim 17, wherein, in General Formula (G1), $A^1$ is the first substituent represented by General Formula (G1-1) and $A^2$ is hydrogen or the second substituent.

* * * * *